US005912140A

United States Patent [19]
Whoriskey et al.

[11] Patent Number: 5,912,140
[45] Date of Patent: Jun. 15, 1999

[54] RECOMBINANT PNEUMOCYSTIS CARINII AMINOACYL TRNA SYNTHETASE GENES, TESTER STRAINS AND ASSAYS

[75] Inventors: Susan K. Whoriskey, Belmont; Cheryl L. Quinn; Niajun Tao, both of Malden; Karen I. Politis-Virk, Watertown; Paul R. Schimmel, Cambridge, all of Mass.

[73] Assignee: Cubist Pharmaceuticals, Inc., Cambridge, Mass.

[21] Appl. No.: 08/415,593

[22] Filed: Apr. 3, 1995

[51] Int. Cl.$^6$ .......................... C12N 15/00; C12N 15/63; C07K 14/195; C07H 21/04

[52] U.S. Cl. .................... 435/69.1; 435/69.7; 435/252.3; 435/254.2; 435/320.1; 530/350; 536/23.2; 536/23.4; 536/24.32

[58] Field of Search .............................. 435/6, 69.1, 71.1, 435/69.7, 71.2, 172.1, 172.3, 183, 243, 252.3, 252.33, 254.1, 254.11, 254.2, 254.21, 320.1; 514/44; 530/350; 536/23.1, 23.2, 23.4, 24.3, 24.32

[56] References Cited

U.S. PATENT DOCUMENTS

| | | | |
|---|---|---|---|
| 4,713,337 | 12/1987 | Jasin et al. | 435/172.3 |
| 4,788,148 | 11/1988 | Nilsson et al. | 435/252.33 |
| 4,952,501 | 8/1990 | Jasin et al. | 435/69.2 |
| 4,963,487 | 10/1990 | Schimmel et al. | 435/172.3 |
| 5,370,995 | 12/1994 | Hennecke et al. | 435/69.1 |

FOREIGN PATENT DOCUMENTS

WO 95/09927  4/1995  WIPO .

OTHER PUBLICATIONS

Webster, T., et al., "Specific Sequence Homology and Three–Dimensional Structure of an Aminoacyl Transfer RNA Synthetase," *Science*, 226:1315–1317, Dec. 1984.

Edwards, H., et al., "An *E. coli* Aminoacyl–tRNA Synthetase Can Substitute for Yeast Mitochondrial Enzyme Function In Vivo," *Cell*, 51:643–649, Nov. 20, 1987.

Englisch, U., et al., "Structure of the Yeast Isoleucyl–tRNA Synthetase Gene (ILS1)," *Biol. Chem. Hoppe–Seyler*, 368:971–979, Aug. 1987.

Martindale, D.W., et al., "Isolation and complete sequence of the yeast isoleucyl–tRNA synthetase gene (ILS1)," *Current Genetics*, 15:99–106 (1989).

Jenal, U., et al., "Isoleucyl–tRNA Synthetase of *Methanobacterium thermautotrophicum* Marburg," *The Journal of Biological Chemistry*, 266(16):10570–10577, Jun. 5, 1991.

Racher, K.I., et al., "Expression and Characterization of a Recombinant Yeast Isoleucyl–tRNA Synthetase," *The Journal of Biological Chemistry*, 266(26):17158–17164, Sep. 15, 1991.

Csank, C., et al., Isoleucyl–tRNA Synthetase from the Ciliated Protozoan *Tetrahymena thermophila*, *The Journal of Biological Chemistry*, 267(7):4592–4599, Mar. 5, 1992.

Shiba, K., et al., "Human cytoplasmic isoleucyl–tRNA synthetase: Selective divergence of the anticodon–binding domain and acquisition of a new structural unit," *Proc. Natl. Acad. Sci. USA*, 91:7435–7439, Aug. 1994.

von der Haar, F. et al, "Target Directed Drug Synthesis: The Aminoacyl–tRNA Synthetases as Possible Targets," *Angew. Chem. Int. Ed.*, 20(3):217–302 (1981).

Chalker, A.F., et al., "Analysis and Toxic Overexpression in *Escherichia coli* of a Staphylococcal Gene Encoding Isoleucyl–tRNA Synthetase," *Gene*, 141:103–108 (1994).

Hughes, J. and Mellows, G., "Interaction of Pseudomonic Acid A with *Escherichia coli* B Isoleucyl–tRNA Synthetase," *Biochem J.*, 191:209–219 (1980).

Weygand–Đurašević, I., et al., "Yeast Seryl–tRNA Synthetase Expressed in *Escherichia coli* Recognizes Bacterial Serine–Specific tRNAs in vivo," *Eur. J. Biochem.*, 214:869–877 (1993).

Walter, R. D. and Kuhlow, F., "Parasite–Specific Interaction of N–[4–(4' Nitroanilino) –Phenyl]–S–(β–Carboxyethyl) – Dithiocarbamic Acid–Ester with Arginyl–tRNA–Synthetase from *Dirofilaria immitis,*" *Trop. Med. Parasit.*, 36:230–232 (1985).

Shepard, A., et al., "RNA Binding Determinant in Some Class I tRNA Synthetases Identified by Alignment–Guided Mutagenesis," *Proc. Natl. Acad. Sci. USA*, 89:9964–9968 (1992).

Shiba, K. and Shimmel, P., "Functional Assembly of a Randomly Cleaved Protein," *Proc. Natl. Acad. Sci. USA*, 89:1880–1884 (1992).

Iaccarino, M. and Berg, P., "Isoleucine Auxotrophy as a Consequence of a Mutationally Altered Isoleucyl–Transfer Ribonucleic Acid Synthetase," *J. Bacteriol.*, 105:527–537 (1970).

(List continued on next page.)

*Primary Examiner*—Nancy Degen
*Assistant Examiner*—Thomas G. Larson
*Attorney, Agent, or Firm*—Hamilton, Brook, Smith & Reynolds, P.C.

[57] ABSTRACT

Recombinant nucleic acids which encode aminoacyl-tRNA sythetases of pneumocystis origin or portions of such enzymes, have been isolated. These nucleic acids can be used to make expression constructs and transformed host cells for the production of pneumocystis aminoacyl-tRNA synthetases. They can also be used in the further isolation of nucleic acids related by DNA sequence similarities, which also encode pneumocystis aminoacyl-tRNA synthetases, or portions thereof. A further embodiment of the invention is antisense nucleic acid which can hybridize to the nucleic acid which encodes the aminoacyl-tRNA synthetase of pneumocystis. The invention also relates to enzymes, isolated and/or recombinant pneumocystis aminoacyl-tRNA synthetases. Antibodies which bind to these enzymes can be made and can be used in the purification and study of the enzymes. Tester strains, which are cells engineered to rely on the function of the tRNA synthetase encoded by an introduced cloned gene, can be used to test the effectiveness of drug candidates in the inhibition of the essential tRNA synthetase enzyme encoded by an introduced cloned pneumocystis gene.

41 Claims, 12 Drawing Sheets

OTHER PUBLICATIONS

Meinnel, T., et al., "Aminoacyl–tRNA Synthetases: Occurrence, Structure, and Function." In tRNA: *Structure, Biosynthesis, and Function,* Söll, D. and RajBhandary, U., eds. (Washington, DC: American Society for Microbiology), pp. 251–300 (1995).

Jasin, M. and Schimmel, P., "Deletion of an Essential Gene in *Escherichia coli* by Site–Specific Recombination with Linear DNA Fragments," *J. Bacteriol.,* 159(2) :783–786 (1984).

Edwards, H. and Schimmel, P., "A Bacterial Amber Suppressor in *Saccharomyces cerevisiae* Is Selectively Recognized by a Bacterial Aminoacyl–tRNA Synthetase," *Molecular and Cellular Biology,* 10(4) :1633–1642 (1990).

Shiba, K., et al., "Isolation of Higher Eukaryote Aminoacyl–tRNA Synthetase Genes by an Alignment–Guided Cross–Species PCR: Application to Human Isoleucine tRNA Synthetase," [From *Programme and Abstracts,* p. F.46], 15th International tRNA Workshop, Société Francaise de Biochimie et Biologie Moléculaire, Cap d'Agde, France, May 30–Jun. 4 (1993), Abstract No. 364.

Printout of a computer record of parts of a poster presented at Cap d'Agde, France, May 30–Jun. 4, 1993, 15th International tRNA Workshop, Société Francaise de Biochimie et Biologie Moléculaire.

Sequence of Human Isoleucyl–tRNA Synthetase Gene, GenBank Name: HSU04953, Accession: U04953, National Center for Biotechnology Information Seq ID: 450850. Entered by Nichols, R.C., et al. First Available: Jan. 13, 1994; Updated: Jan. 26, 1994.

Hughes, J., et al., "Inhibition of Isoleucyl–Transfer Ribonucleic Acid Synthetase in *Escherichia coli* by Pseudomonic Acid," *Biochem. J.,* 176:305–318 (1978), Great Britain.

Mirande, M. and Waller, J–P., "The Yeast Lysyl–tRNA Synthetase Gene," *The Journal of Biological Chemistry,* 263(34) :18443–18451 (1988).

Chan, V. L., and Bingham, H. L., "Lysyl–tRNA Synthetase Gene of *Campylobacter jejuni,*" *Journal of Bacteriology,* 174(3) :695–701 (1992).

Gatti, D. L., and Tzagoloff, A., "Structure and Evolution of a Group of Related Aminoacyl–tRNA Synthetases," *J. Mol. Biol.,* 218:557–568 (1991).

Lévêque, F., et al., "Homology of lysS and lysU, the Two *Escherichia coli* Genes Encoding Distinct Lysyl–tRNA Synthetase Species," *Nucleic Acids Research,* 18(2) :305–312 (1990).

Kawakami, K., et al., "Chromosomal Location and Structure of the Operon Encoding Peptide–Chain–Release Factor 2 of *Escherichia coli,*" *Proc. Natl. Acad. Sci. USA,* 85:5620–5624 (1988).

Clark, R. L., and Neidhardt, F. C., "Roles of the Two Lysyl–tRNA Synthetases of *Escherichia coli:* Analysis of Nucleotide Sequences and Mutant Behavior," *Journal of Bacteriology,* 172(6) :3237–3243 (1990).

Sequence of *Saccharomyces cerevisiae* Cytoplasmic Alanyl–tRNA Synthetase Gene, Complete cds, GenBank Accession: U18672. Entered by Ripmaster, T. L. First available Jan. 2, 1995.

Herlihy, W. C., et al., "Mass Spectra of Partial Protein Hydrolysates as a Multiple Phase Check for Long Polypeptides Deduced from DNA Sequences: $NH_2$–Terminal Segment of Alanine tRNA Synthetase," *Proc. Natl. Acad. Sci. USA,* 77(11) :6531–6535 (1980).

Chang, P. K. and Dignam, J. D., "Primary Structure of Alanyl–tRNA Synthetase and the Regulation of Its mRNA Levels in *Bombyx mori,*" *The Journal of Biological Chemistry,* 265(34) :20898–20906 (1990).

Selbitschka, W., et al., "Characterization of recA Genes and recA Mutants of *Rhizobium meliloti* and *Rhizobium leguminosarum* Biovar *viciae,*" *Mol. Gen. Genet,* 229:86–95 (1991).

Putney, S.D., et al., "Primary Structure of a Large Aminoacyl–tRNA Synthetase," *Science,* 213:1497–1501 (1981).

Sequence of *Arabidopsis thaliana* Alanyl–tRNA Synthetase Gene. Mireau, H., et al., EMBL Accession No. Z22673. File created May 7, 1993.

Kim, S., et al., "Diversified Sequences of Peptide Epitope for Same–RNA Recognition," *Proc. Natl. Acad. Sci. USA,* 90:10046–10050 (1993).

Archibold, E.R., and Williams, L.S., "Regulation of Methionyl–Transfer Ribonucleic Acid Synthetase Formation in *Escherichia coli* and *Salmonella typhimurium,*" *Journal of Bacteriology,* 114(3) :1007–1013 (1973).

Tzagoloff, A., et al., "Characterization of MSM1, the Structural Gene for Yeast Mitochondrial Methionyl–tRNA Synthetase," *Eur. J. Biochem.,* 179:365–371 (1989).

Dardel, F., et al., "Molecular Cloning and Primary Structure of the *Escherichia coli* Methionyl–tRNA Synthetase Gene," *Journal of Bacteriology,* 160(3) :1115–1122 (1984).

Nureki, O., et al., "Methionyl–tRNA Synthetase Gene From an Extreme Thermophile, *Thermus thermophilus* HB8," *The Journal of Biological Chemistry,* 266(5) :3268–3277 (1991).

Mechulam. Y., et al., "Methionyl–tRNA Synthetase from *Bacillus stearothermophilus:* Structural and Functional Identities with the *Escherichia coli* Enzyme," *Nucleic Acids Research,* 19(13) :3673–3681 (1991).

Walter, P., et al., "Primary Structure of the *Saccharomyces cerevisiae* Gene for Methionyl–tRNA Synthetase," *Proc. Natl. Acad. Sci. USA,* 80:2437–2441 (1983).

Fasiolo, F., et al., "Cytoplasmic Methionyl–tRNA Synthetase from Bakers' Yeast," *The Journal of Biological Chemistry,* 260(29) :15571–15576 (1985).

Jones, M. D., et al., "Natural Variation of Tyrosyl–tRNA Synthetase and Comparison with Engineered Mutants," *Biochemistry,* 25:1887–1891 (1986).

Barker, D. G., et al., "The Tyrosyl–tRNA Synthetase from *Escherichia coli,*" *FEBS Letters,* 150(2) :419–423 (1982).

Chow, C. M., and RajBhandary, U. L., "*Saccharomyces cerevisiae* Cytoplasmic Tyrosyl–tRNA Synthetase Gene," *The Journal of Biological Chemistry,* 268(17) :12855–12863 (1993).

Salazar, O., et al., "*Thiobacillus ferrooxidans* Tyrosyl–tRNA Synthetase Functions In Vivo in *Escherichia coli,*" *Journal of Bacteriology,* 176(14) :4409–4415 (1994).

Sequence of *Mycobacterium leprae* cosmid L247 as in database on Sep. 13, 1994. GenBank Accession No. U00021. Submitted by Robison, K., Nov. 1, 1993 (22 pages).

Henkin, T. M., et al., "Analysis of the *Bacillus subtilis* tyrS Gene: Conservation of a Regulatory Sequence in Multiple tRNA Synthetase Genes," *Journal of Bacteriology,* 174(4) :1299–1306 (1992).

Akins, R. A., and Lambowitz, A. M., "A Protein Required for Splicing Group I Introns in Neurospora Mitochondria Is Mitochondrial Tyrosyl–tRNA Synthetase or a Derivative Thereof," *Cell,* 50:331–345 (1987).

Winter, G., et al., "The Amino Acid Sequence of the Tyrosyl–tRNA Synthetase from *Bacillus stearothermophilus*," *Eur. J. Biochem.*, 132:383–387 (1983).

Schlesinger, S., and Nester, E. W., "Mutants of *Escherichia coli* with an Altered Tyrosyl–Transfer Ribonucleic Acid Synthetase," *Journal of Bacteriology*, 100(1) :167–175 (1969).

Glaser, P., et al., "A Gene Encoding a Tyrosine tRNA Synthetase is Located Near sacS in *Bacillus subtilis*," *DNA Sequence*, 1:251–261 (1991).

Kämper, U., et al., "The Mitochondrial Tyrosyl–tRNA Synthetase of *Podospora anserina* Is A Bifunctional Enzyme Active in Protein Synthesis and RNA Splicing," *Molecular and Cellular Biology*, 12(2) :499–511 (1992).

Dignam, J. D., et al., "Alanyl–tRNA Synthetase from *Escherichia coli, Bombyx mori* and *Ratus ratus,* Existence of Common Structural Features," *Eur. J. Biochem.* 198:201–210 (1991).

Fletcher et al "Isolation and identification of six Pneumocystis carinii genes utilizing codon bias " Gene 129: 167–174 1993.

Sambrook et al. "Molecular Cloning: A Laboratory Manual, Second Edition" Cold Spring Harbor Laboratory Press, pp. 8.51–8.52 1989.

Webster's II New Riverside University Dictionary, Houghton Mifflin Co., New York. p. 1232 1994.

```
                        Nde I
GGTCGACTCTAGAGGATCTACTAGTCATATGGATTATGGAAGTGGAGACGCCGATGATGAATTTTATTCC
----+----+----+----+----+----+----+----+----+----+----+----+----+----+   70
CCAGCTGAGATCTCCTAGATGATCAGTATACCTAATACCTTCACCTCTGCGGCTACTACTTAAAATAAGG

AGGAGGTGCCAGTGCTAAGCCTTTTATCACACACATCATAACGAGCTTGATCTTAATCTTTATTTAAGAGTT
----+----+----+----+----+----+----+----+----+----+----+----+----+----+  140
TCCTCCACGGTCACGATTCGGAAAATAGTGTGTAGTATTGCTCGAACTAGAATTAGAAATAAATTCTCAA

GCACCTGAATTATATTTAAAAAATGTTAGTGATAGGAGGCTTGAATCGGGTTTATGAAATTGGAAAGCAAT
----+----+----+----+----+----+----+----+----+----+----+----+----+----+  210
CGTGGACTTAATATAAATTTTTACAATCACTATCCTCCGAACTTAGCCCAAATACTTTAACCTTTCGTTA
                                                          Bam HI
TTAGGAATGAGAGTATTGATCTTACGCACAACCCCGAATTCACCATGATAATCGGATCCCCGGGTACCGA
----+----+----+----+----+----+----+----+----+----+----+----+----+----+  280
AATCCTTACTCTCATAACTAGAATGCGTGTTGGGGCTTAAGTGGTACTATTAGCCTAGGGGGCCCATGGCT

GCTCGAA
---+--> 287
CGAGCTT
```

FIG. 1

Bam HI
TTCGAGCTCGGTACCCGGGGATCCGATTGCCGAATTCGGGTGGGATTGTCATGGGCTGCCTGTTGAACATG
AAGCTCGAGCCCATGGGCCCCTAGGCTTAAGCCCACCCTAACAGTACCCGACGGACAACTTGTAC       70

AAATAGATAAAAAACTTGGGATTAATGGAAAAGAAGATATAATGGCAATAGGGATTGAGAAGTGACGAGA
TTTATCTATTTTTTGAACCCTAATTACCTTTTCTTCTATATTACCGTTATCCCTAACTCTTCACTGCTCT  140

AATGGTTTATTTATATCTGTTTTACCATATTCTAGATATAACAGTGAATGCCGTGCAATTGTTATGAGGT
TTACCAAATAAATATAGACAAAATGGTATAAGATCTATATTGTCACTTACGGCACGTTAACAATACTCCA  210

ATTCTGAGCAATGGAGGGAGAAAATTGAAAGATTAGGTAGATGGATTGAGTTTGATAATGATTACAAGAC
TAAGACTCGTTACCTCCCTCTTTTAACTTTCTAATCCATCTACCTAACTCAAACTATTACTAATGTTCTG  280

TCTTGATACATTATTTATGCAATCAGTATGGTATATTTTTAAGAAGCTGTATGAAAAGGGTAAAGTATAT
AGAACTATGTAATAAATACGTTAGTCATACCATATAAAAAATTCTTCGACATACTTTTCCCATTTCATATA 350

FIG. 2A

```
                                                                      420
AGAGGGTTTAAGGTTATGCCATATTCTACAGCATGACACCTCTTAGTAACTTTGAAGCTCAGCAGA
|---+----+----+----+----+----+----+----+----+----+----+----+----+--|
TCTCCCAAATTCCAATACGGTATAAGATGTCGTACTGTGGAGAATCATTGAAACTTCGAGTCGTCT

490
ATTATAAAAAGTTAGTGATGATCCATCTGGTAAATTTTTTGAATATATGTTTTATATTCTAAATAGT
|---+----+----+----+----+----+----+----+----+----+----+----+----+--|
TAATATTTTTCAATCACTACTAGGTAGACCATTTAAAAAACTTATATACAAAATATAAGATTTAACTTATCA

560
TGTTATATCTTTTCCTTTATTGGAAGATCCATCTACATCATTACTTGCATGGACCACCACCCCCTGGACC
|---+----+----+----+----+----+----+----+----+----+----+----+----+--|
ACAATATAGAAAAGGAAATAACCTTCTAGGTAGATGTAGTAATGAACGTACCTGGTGGTGGGGGACCTGG

NdeI                                                           628
CTCCCCAATCCATATGACTAGTAGAGATGGTGTAGAGTCGACCTGCAGGCATGCAAGCTTTCCCTATAGTG
|---+----+----+----+----+----+----+----+----+----+----+----+----+--|
GAGGGTTAGGTATACTGATCATCTACCACATCTCAGCTGGACGTCCGTACGTTCGAAAGGGATATCAC
```

FIG. 2B

```
GAATTCTTTTCTGACGGGACGACGAGCACGGTATTAAAGTGGAACATTTATTCATTTTTAGGATGATA     70
         +         +         +         +         +         +         +
CTTAAGAAAGACTGCCCCTGCTCGTGCCATAATTTCACCTTGTAAATAAGTAAAAAATCCTACTAT

CCAATGCCTTATAGGTAGAGAAGGCGGTTTAAAATCAGGTTTAAGTCCTTCATTATTTGTGAGAAAT    140
         +         +         +         +         +         +         +
GGTTACGGAATATCCATCTCTTCCGCCGAAATTTAGTCCAAATTCAGGAAGTAATAAAACACTCTTTA

GTCGGAGCGTTTAAAATATTTGGCTAAATTAGCAAATATTGATCATAAAGATTTTAGTCGTACAACTAAT    210
         +         +         +         +         +         +         +
CAGCCTCGCAAATTTATAAACCGATTTAATCGTTTATAACTAGTATTTCTAAAATCAGCATGTTGATTA

CCTAAACATTGTCAATCTGTCCAATGTTTTTGGAAAGTTTTGAGGGATAAAGGATATATTTATGAAAATA    280
         +         +         +         +         +         +         +
GGATTTGTAACAGTTAGACAGGTTACAAAACCTTTCAAACTCCCTATTTCCTATATAAATACTTTTAT

AACATGAAGGATGGTATGCTGCACGTGCTGATGATGAAACCTTTTACCCATCTAAAGCTGTTAAAAAATACGGAA    350
         +         +         +         +         +         +         +
TTGTACTTCCTACCATACGACGTGCACTACTACTTTGGAAAATGGGTAGATTTCGACAATTTTTTATGCCTT
```

FIG. 3A

```
TTCAGATGGTGCTATGCTGACTGTAAATGTTTTATTATTTTAAGTGTTTTCTTAGTCATAGTAGATT
       |         |         |         |         |         |         |    420
AAGTCTACCACGATACGACTGACATTTACAAAATAATAAAATTCACAAAGAATCAGTATCATCTAA

TCTATTGAGACGGGTGCCAATGTTGAATTTCTGAAAATAATTATCATTTCCGACTATCTAAATTTA
       |         |         |         |         |         |         |    490
AGATAACTCTGCCCACGGTTACAACTTACCTAAAGACTTTTATTAATAGTAAAGGCTGATAGATTTAAAT

AAAATCAGTTATTGGATCATTACAGAAAAAAATCCTTGTTTTTGTTATTCCCAGATCCGAACAAAATAATTT
       |         |         |         |         |         |         |    560
TTTTAGTCAATAACCTAGTAATGTCTTTTTTTAGGAACAATAAGGGTCTAGGCTTGTGTTTTATTAAA

Nde I
          .......
ATATCATATGATCGAGCAAGGATTAAAATGATATTAGTATATCTAGACCAAGCTCTCGCTATTCATGGGGT
       |         |         |         |         |         |         |    630
TATAGTATACTAGCTCGTTCCTAATTTACTATAATCATATAGATCGGTTCGAGAGCGATAAGTACCCCA

ATTCGAGTACCTGATGATGAGTCTCAAACAATATACGTCTGGCACGACGCCACCATCGGCTAT    693
       |         |         |         |         |         |
TAAGCTCATGGACTACTACTCAGAGTTTGTTATATGCAGACCGTGCTGCGGGTGGTAGCCGATA
```

```
EcoRI
GAATTCGGCACGAGAAAAACAAAGGATGGAGGAATCTTCCACCAAGTAACCCGATAAAACAGCTTGGAACCTTTGTTTAGATGAAAGGTCGGGGAA
----+----+----+----+----+----+----+----+----+----+----+----+----+----+----+----+----+----+----+----  100
CTTAAGCCGTGCTCTTTTTGTTTCCTACCTCCTTAGAAGTGGTTCATTGGGCTATTTGTCGAACCAATCTACTTCTTCCAGCCCCTT
      Asn Ser Ala Arg Glu Lys Asn Lys Arg Met Glu Glu Ser Ser Pro Ile Lys Gln Leu Gly Asn Cys Leu Asp Glu Arg Ser Gly Glu

TATGTCTCAAAAACAGAGTTAAAAAAGACGGTTAAAAACTTCAGGAAAAAAGAGAAGCATTAACTACAGTTCACCAAAACCTGTTA
----+----+----+----+----+----+----+----+----+----+----+----+----+----+----+----+----+----+----+----  200
ATACAGAGTTTTTGTCTCAATTTTTCTGCCAATTTTGAAGTCCTTTTTCTTCGATTCGTAATTGATGTCAAGTGGTTTGGACAAT
Tyr Val Ser Lys Thr Glu Leu Lys Arg Arg Leu Lys Leu Gln Glu Lys Lys Arg Glu Lys Ala Lys Ala Leu Thr Thr Val Ser Pro Lys Pro Val

AAAAACATGTTTCAGAATTAATGAAGATTTAACGCCTAATGTTTATTATGAGCTTCGTTCTCGGCATATTAATATGCTTAAAACTTAGA
----+----+----+----+----+----+----+----+----+----+----+----+----+----+----+----+----+----+----+----  300
TTTTTGTACAAAGTCTTAATTACTTCTAAATTGCGGATTACAAATAATACTCGAAGCAAGAGCCGTATAATTATACGAAGATTTTGAATCT
Lys Lys His Val Ser Glu Ile Asn Glu Asp Leu Thr Pro Asn Val Tyr Tyr Glu Leu Arg Ser Arg His Ile Asn Met Leu Arg Ala Ser Lys Asn Leu Asp
                                                                                EcoRI

TCCATATCCGCATAAGTTTTGTGTCAATATTCAGATTGAAGAATTCATTAAAACCTACAGTTTTATGAAGAGGAGAAGTAATAGGACATTATTGTT
----+----+----+----+----+----+----+----+----+----+----+----+----+----+----+----+----+----+----+----  400
AGGTATAGGCGTATTCAAAACACAGTTATAAGTCTAACTTCTTAAGTAATTTGGATGTCAAAATACTTCTCCTCTTCATTATCCTGTAATAACAA
Pro Tyr Pro His Lys Phe Cys Val Asn Ile Gln Ile Glu Glu Phe Ile Lys Thr Tyr Ser Phe Met Lys Arg Gly Glu Val Asn Arg Asp Ile Ile Val

TCTGTTGCAGGAAGAATATTAAATAAGGGGATTCGGGTTCAAAATTGCGTTTTATGATCTTTGTGATGATGGTCAAAATTCAAGTGATGGCCAAG
----+----+----+----+----+----+----+----+----+----+----+----+----+----+----+----+----+----+----+----  500
AGACAACGTCCTTCTTATAATTTATTCGCCCTAAGCCCAAGTTTTAACGCAAAATACTAGAAACACTACCACCAGTTTTAAGTTCACTACCGGTTC
Ser Val Ala Gly Arg Ile Leu Asn Lys Arg Asp Ser Gly Ser Lys Leu Arg Asp Leu Cys Asp Gly Ala Lys Ile Gln Val Met Ala Gln
```

```
ATATAACAGAAGAAATGTTATCAAATGGTTTATGAATTAACCGGTGATTACAAGATTAAATATCATGTTAATGAGCTCGAAGAAGTTACTATTGATTT
----+----+----+----+----+----+----+----+----+----+----+----+----+----+----+----+----+----+----+----  1200
TATATTGTCTTCTTACAATAGTTTATACCAAATGGCCACTAATTAATTGTTCTAATTTATAGTACAATTACTCGAGCTTCTTCAATGATAACTAAA
Asp Ile Thr Glu Glu Met Val Tyr Glu Leu Thr Gly Asp Tyr Lys Ile Lys Tyr His Val Asn Glu Leu Glu Val Thr Ile Asp Phe

CTCAAGGCCATGGAATCGTATAGAAGTTATTCCATTTTTGGAAGAAAAACTCAATGTGTTTTCCCTCGTGATCAATTACAGAAGAAACGACT
----+----+----+----+----+----+----+----+----+----+----+----+----+----+----+----+----+----+----+----  1300
GAGTTCCGGTACCTTAGCATATCTTCAATAAGGTAAAAACCTTCTTTTTGAGTTACACAAAAAGGAGACCACTAGTTAACGTATGTCTTCTTTGCTGA
Ser Arg Pro Trp Asn Arg Ile Glu Val Ile Pro Phe Leu Glu Lys Leu Asn Val Val Phe Pro Pro Gly Asp Gln Leu His Thr Glu Thr Thr

AACTTTCTTATCTCCTTATGTGAAAAACATCATGTTGAATATTTACCACCCATAACAAATTCTAGATTATTTGATAAGCTTATCAGTGAATTTTTGGAAC
----+----+----+----+----+----+----+----+----+----+----+----+----+----+----+----+----+----+----+----  1400
TTGAAAGAATAGAGGAATACACTTTTTGTAGTACAACTTATAAATGGTGGGTATTGTTAAGATCTAATAAACTATTCGAATAGTCACTTAAAAACCTTG
Asn Phe Leu Ile Ser Leu Cys Glu Lys His His Val Glu Tyr Leu Pro Pro Ile Thr Asn Ser Arg Leu Phe Asp Lys Leu Ile Ser Glu Leu Glu

CTCTATGTCTCTTAATCCGACATTTTTGATAGGTCATCCTCAAATTATGTCTCCATTGGCAAAATCATCATAGATCTAATGTAGGATTATGTGAAAGATTTGA
----+----+----+----+----+----+----+----+----+----+----+----+----+----+----+----+----+----+----+----  1500
GAGATACAGAATTAGGCTGTAAAACTATCCAGTAGGAGTTTAATACAGAGGTAACCGTTTGTAGTATCTAGATTACATCCTAATACACTTTCTAAACT
Pro Leu Cys Leu Asn Pro Thr Phe Leu Ile Gly His Pro Gln Ile Met Ser Pro Leu Lys His His Arg Ser Asn Val Gly Leu Cys Glu Arg Phe Glu

ATTATTTGTAGCCTATAAAGAACTTGTTAACGCATACGGAACTAAATGATCCAGTTCAACAACGAATAAGATTTGAGGAACAGATCAAACAAAGGGAT
----+----+----+----+----+----+----+----+----+----+----+----+----+----+----+----+----+----+----+----  1600
TAATAAACATCGGATATTTCTTGAACATTGCGTATGTGCCTTGATTACTAGGTCAAGTTGCTTATTCTAAACTCCTTGTCTAGTTGTTTCCCTA
Leu Phe Val Ala Tyr Lys Glu Leu Val Asn Ala Tyr Thr Glu Leu Asn Asp Pro Val Gln Gln Arg Ile Arg Phe Glu Gln Ile Lys Gln Arg Asp

CAAGGAGAGATGATGAAGTTCAAATTATTGATGAGAATTTTTGTTTAGCTTTGGATTATGGATTACCGCTACTGCAGGATGGGAATGGGAATAGATCGAC
----+----+----+----+----+----+----+----+----+----+----+----+----+----+----+----+----+----+----+----  1700
GTTCCTCTACTACTTCAAGTTTAATAACTACTCTTAAAAACAATCGAAACTAATACCTAATGGCGGATGACGTCCTACCCTTATCTAGCTG
Gln Gly Asp Glu Val Gln Ile Ile Asp Glu Asn Phe Cys Leu Ala Leu Asp Tyr Gly Leu Pro Pro Thr Ala Gly Trp Gly Met Gly Ile Asp Arg
```

RECOMBINANT PNEUMOCYSTIS CARINII AMINOACYL TRNA SYNTHETASE GENES, TESTER STRAINS AND ASSAYS

BACKGROUND OF THE INVENTION

*Pneumocystis carinii* is an opportunistic pathogen which causes pulmonary infections. In particular, *P. carinii* is a common causative agent of pneumonia in immunocompromised individuals, such as patients with AIDS, children with immunodeficiency disorders and those receiving immunosuppressive therapy for malignancy or transplantation. The rapid rise in the incidence of AIDS since the early 1980s has changed the status of *P. carinii* from a rare opportunistic pathogen to a common infection in immunocompromised individuals. It has been reported that greater than 70% of all AIDS patients in the U.S. develop pneumonia complications due to *P. carinii* (W. T. Hughes, *J. Protozool.* 38:243S (1991); J. Mills, *Rev. Infect. Dis.* 8:1001 (1986)) and that 50% of AIDS patients have recurrent infections (L. J. Deloreno, et al. *Chest* 88:79–83 (1985); H. Masur, and J. A. Kovacs, *Infect. Dis. Clin. N. Am.* 2:419–428 (1988)). Reports indicate that *P. carinii* infection is now recognized as a major cause of death (J. F. Murry, et al., *Am. Rev. Respir. Dis.* 135:504–509 (1987)) in AIDS patients in spite of the introduction of prophylaxis for treatment of the pneumonia (W. T. Hughes, *J. Protozool.* 38:2S (1991). Furthermore, there is a high incidence of adverse reactions among AIDS patients to existing anti-*P. carinii* treatments.

The worldwide incidence of *P. carinii* is difficult to determine because surveillance of the organism is not required in most countries (M. T. Cushion et al., *Interntl. Rev. of Cyt.* 131:59–106 (1991)). However, a review of worldwide reports of pneumonia showed that very few countries have not reported *P. carinii* (W. T. Hughes, in *Pneumocystis carinii Pneumonitis* W. T. Hughes, Ed. (CRC Press, Boca Raton, 1987), vol. 1, pp. 14–20, 97–104).

Analysis of *P. carinii* at the molecular level is in the very early stages. The genome is about 7000 kb in size and has at least 13 chromosomes (B. Lundren at al., *Infect. Immun.* 58:1705–1710 (1990); S. T. Hong, et al., *J. Clin. Microbiol.* 28:1785–1795 (1990)). The cloning and characterization of only a few genes has been reported. These data have revealed that the genome is A+T rich (U. Edman et al., *Proc. Natl. Acad. Sci. U.S.A.* 86:6503 (1989); J. C. Edman et al., *Proc. Natl. Acad. Sci. U.S.A.* 86:8625 (1989); L. D. Fletcher et al., *Gene* 129:167–174 (1993)). Little if any information is available on the regulatory sequences involved in transcription and translation. However, the greatest stumbling block to date in studying *P. carinii* has been the inability to reliably propagate sufficient quantities of the organism in the laboratory (E. Sloand, et al., *J. Euk. Microbiol.* 40:188–195 (1993)).

Rat derived and human derived *P. carinii* are very similar organisms, with differences at the DNA sequence level. Currently, a time consuming in vivo method is used whereby an immunocompromised mouse or rat is injected intratracheally with either rat-derived or human-derived *P. carinii* and the pathogen multiplies and develops in the lung tissues (E. Sloand, et. al., *J. Euk. Microbiol.* 40:188–195 (1993), K. K. Sethi, *Experientia* 48:63–67 (1992)).

These difficulties present a need for alternative strategies for study of the organism which can yield new therapeutic agents to prevent or control infection. In this regard, there is a need to identify molecular targets of pneumocystis whose function can be specifically inhibited by antimicrobial agents.

The design of effective antibiotics should exploit the biological differences between the pathogen and host. Designing new antibiotics requires the identification of potential targets in *Pneumocystis carinii*. The search for exploitable differences in the enzymatic pathways of *P. carinii* and humans is hindered by the limited understanding of the organism's biology. The use of in vitro methods to produce and study target enzymes of *P. carinii* and the use of tester strains allows an approach to developing new drugs against *P. carinii* without having to culture the living organism.

Because the amino acid sequences of the tRNA synthetases have diverged over evolutionary time, significant differences exist between the structures of the enzymes from mammals (e.g., human, bovine) and mammalian pathogens. These differences can be exploited by finding inhibitors of aaRS activity which specifically target a tRNA synthetase of a pathogenic organism, and which may further have specific antimicrobial activity. By selectively inactivating one or more of its aminoacyl-tRNA synthetases, *Pneumocystis carinii* infection can be controlled.

SUMMARY OF THE INVENTION

The invention relates to isolated and/or recombinant nucleic acids which encode aminoacyl-tRNA synthetases of pneumocystis origin. The invention also relates to recombinant DNA constructs and vectors containing DNA having a sequence which encodes an aminoacyl-tRNA synthetase of pneumocystis origin, or portions of the enzyme. These nucleic acids and DNA constructs can be used to produce recombinant aminoacyl-tRNA synthetase of pneumocystis origin.

A further embodiment of the invention is antisense nucleic acid which can hybridize to the nucleic acid which encodes the aminoacyl-tRNA synthetase of pneumocystis. In cells, antisense nucleic acid can inhibit the function of an RNA which encodes an aminoacyl-tRNA synthetase of pneumocystis.

The invention also relates to proteins or polypeptides referred to herein as isolated and/or recombinant pneumocystis aminoacyl-tRNA synthetases. These enzymes are useful in biochemical separation of the amino acid which they specifically recognize and in quantitations of the amino acid and ATP. Antibodies which bind to these enzymes can be made and can be used in the purification and study of the enzyme.

The recombinant pneumocystis aminoacyl-tRNA synthetases can be produced in host cells using cells and methods described herein. Tester strains, which are cells engineered to rely on the function of the tRNA synthetase encoded by an introduced cloned gene, are also an embodiment of the invention. Tester strains can be used to test the effectiveness of drug candidates in the inhibition of the essential tRNA synthetase enzyme encoded by the introduced cloned gene. In this way, potential inhibitors of the enzyme can be screened for antimicrobial or antibiotic effects, without requiring the culture of pathogenic strains of pneumocystis, such as *Pneumocystis carinii*.

BRIEF DESCRIPTION OF THE DRAWINGS

FIG. 1 (see also SEQ ID NO:34) is a diagram of the DNA sequence of the cloned PCR fragment of a lysyl-tRNA synthetase from *P. carinii*. Nucleotides 1–35 and 260–287 are sequences of the pT7Blue T-Vector. Nucleotides 36–59 are derived from the polymerase chain reaction (PCR) primer Kiyo-138. Nucleotides 60–236 are *P. carinii* sequence. Nucleotides 237–259 are derived from PCR primer Kiyo-140. The NdeI and BamHI sites within the vector sequences are shown in the figure.

FIGS. 2A–2B (see also SEQ ID NO:35) is a diagram of the DNA sequence of the cloned PCR fragment of an isoleucyl-tRNA synthetase from *P. carinii*. Nucleotides 1–28 and 566–628 are plasmid vector DNA sequences. Nucleotides 29–59 are derived from PCR primer Kiyo-17. Nucleotides 60–539 are a fragment of a *P. carinii* isoleucyl-tRNA synthetase gene. Nucleotides 540–565 are derived from PCR primer Kiyo-036. The two introns within the PCR fragment are at nucleotides 132–175 and nucleotides 448–489. The NdeI and BamHI sites within the vector sequences are shown in the figure.

FIGS. 3A–3B (see also SEQ ID NO:36) is a diagram of the DNA sequence of the cloned PCR fragment of a methionyl-tRNA synthetase from *P. carinii*. Nucleotides 1–22 are derived from PCR primer Kiyo-12. Nucleotides 23–663 are *P. carinii* DNA. Nucleotides 664–693 are derived from PCR primer Kiyo-15. Nucleotides 40–84 and 373–429 are introns.

FIG. 4 (see also SEQ ID NO:37) is a diagram of the DNA nucleotide sequence of the PCR fragment of *P. carinii* tyrosyl-tRNA synthetase. This 590 bp fragment has the PCR primers incorporated at either end (underlined sequences). Nucleotides 1–29 on this figure are from the PCR primer TyrF100, and nucleotides 563–590 are from the PCR primer TyrR281. Because the PCR was done on genomic DNA, this fragment contains three introns (lower case). These introns are at nucleotides 44–87, 141–186, and 206–248. The predicted amino acid translation for open reading frame sequences is presented below the nucleotide sequence.

Figure 5B:
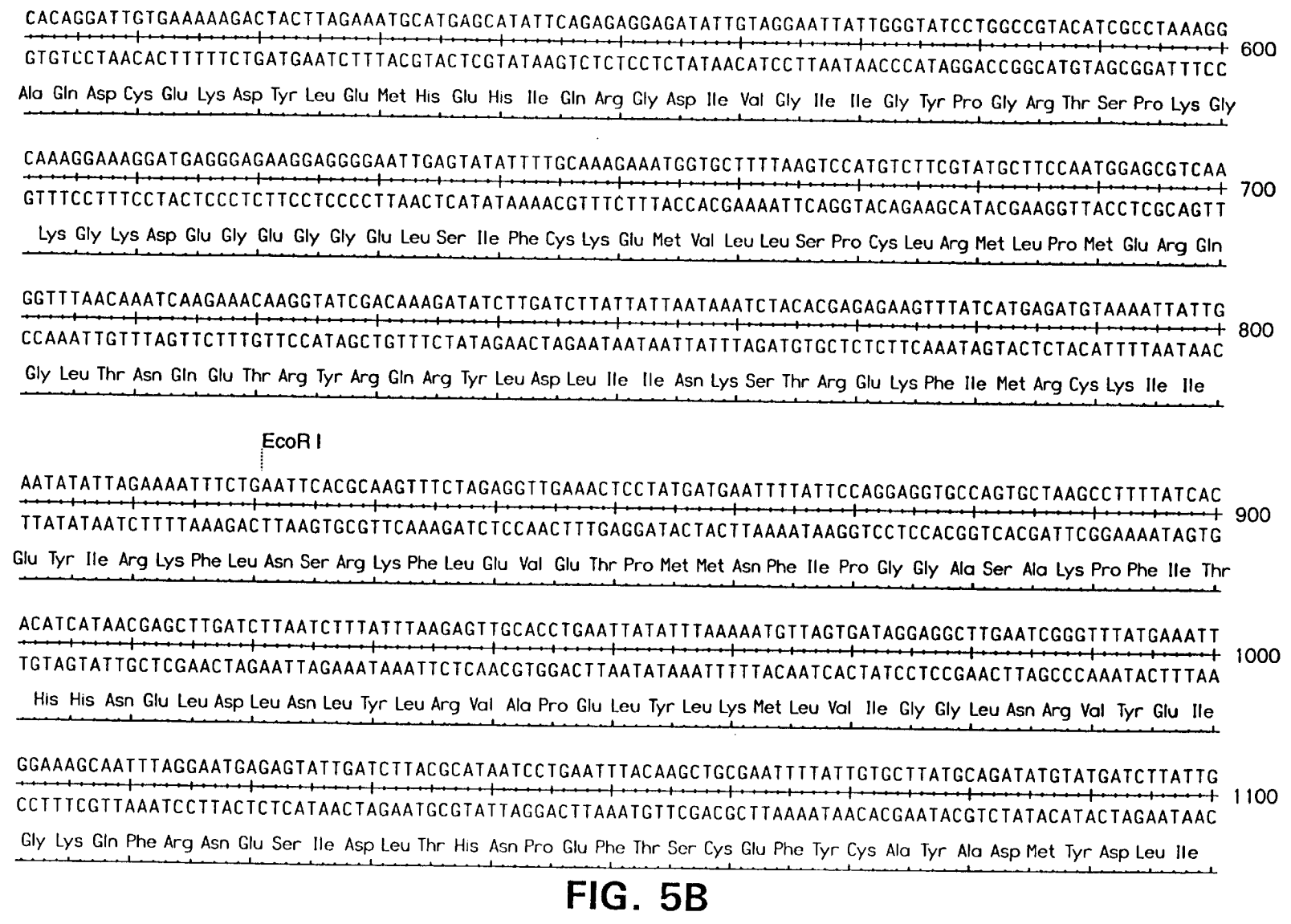
Figure 5D:
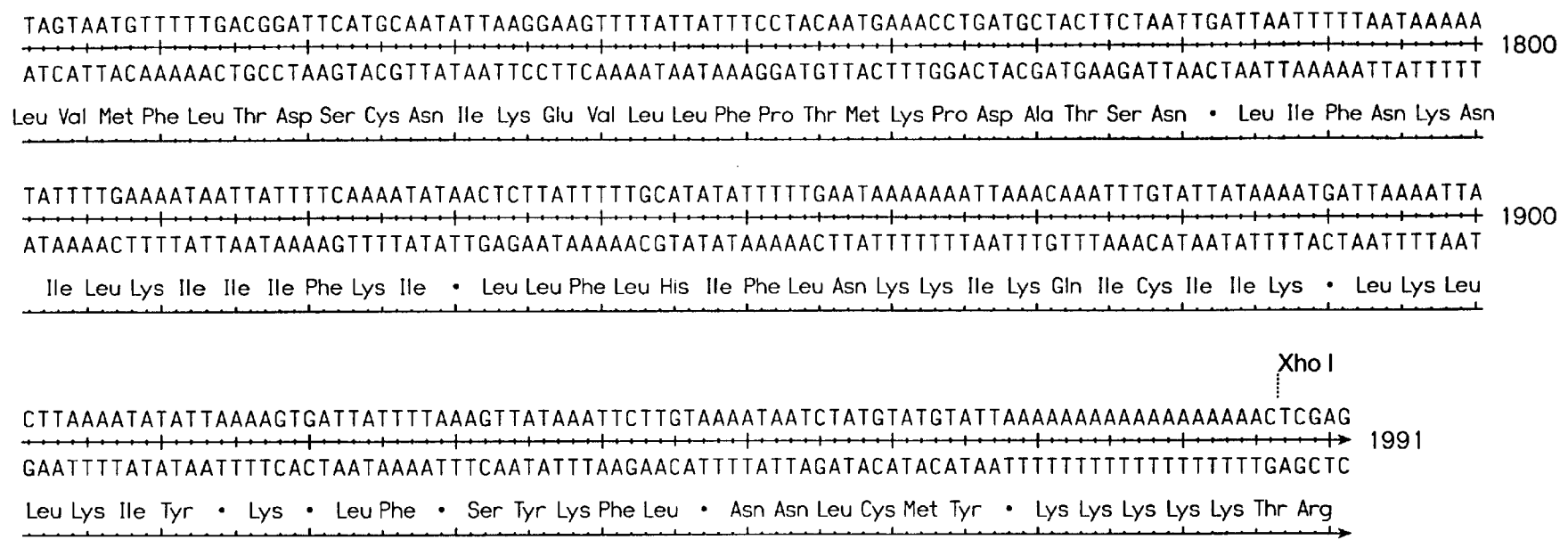

FIGS. 5A–5D (see also SEQ ID NO:40 and SEQ ID NO:41) is a diagram of the DNA sequence and deduced amino acid sequence of the *P. carinii* lysyl-tRNA synthetase cDNA, with the introns removed. The cDNA was cloned into the EcoRI and XhoI sites in the multiple cloning site of the Bluescript SK+ vector. Nucleotides 1–6 are an EcoRI site, nucleotide 7 is the beginning of the 5' untranslated region, nucleotides 29–31 are the initiation codon ATG, and the end of the gene (i.e. the termination codon) TGA is at nucleotides 1781–1783. Nucleotide 1781 is the beginning of the 3' untranslated region. The poly A tail begins at nucleotide 1968. The XhoI site is at nucleotides 1986–1991.

Figure 6:
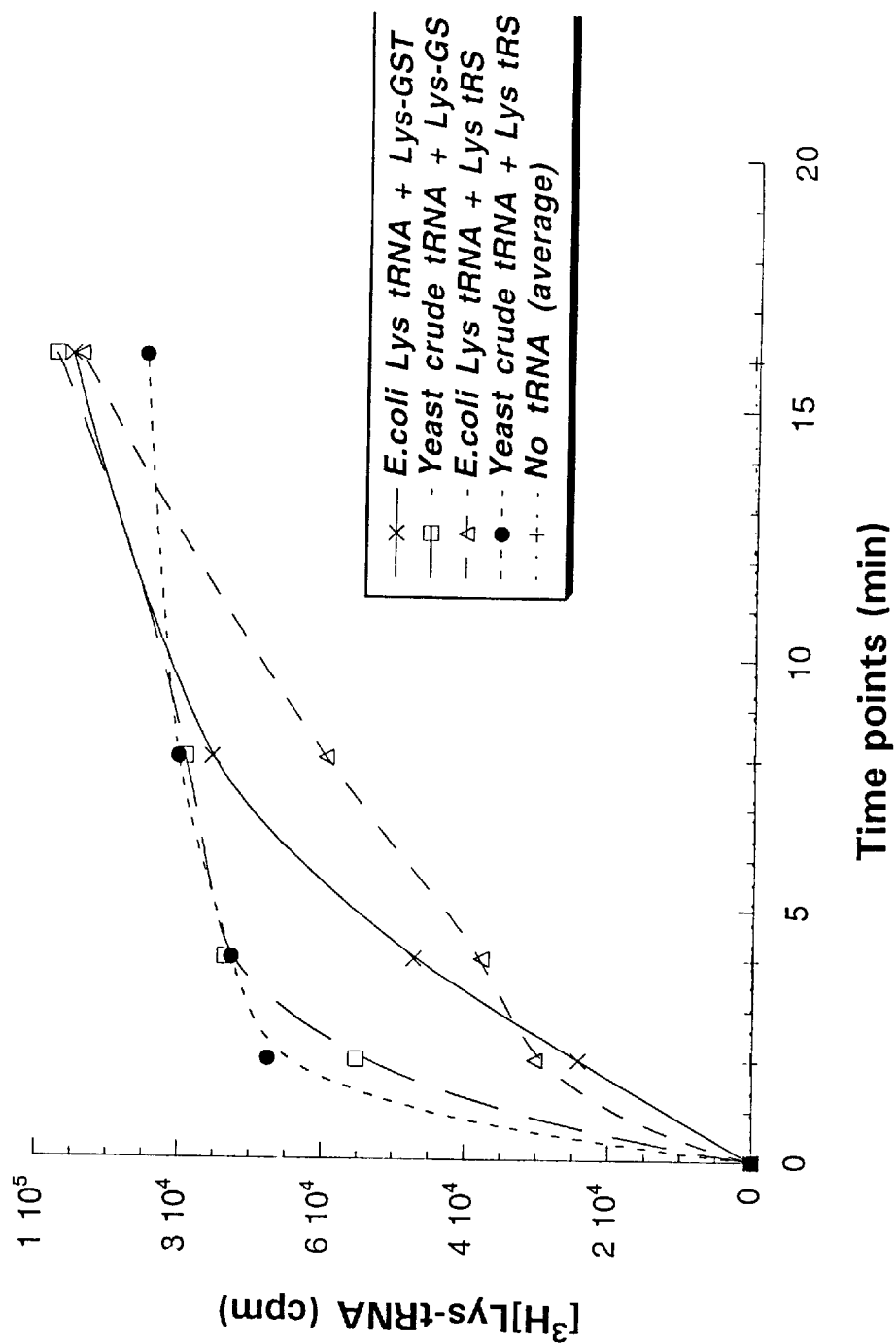

FIG. 6 is a graph showing the extent of aminoacylation of tRNA over time by purified, uncleaved GST-lysyl-tRNA synthetase (Lys-GST) and purified, cleaved GST-lysyl-tRNA synthetase (Lys tRS) in a charging activity assay (see Example 13; GST is glutathione S-transferase of *Schistosoma japonicum*). For X symbols, the enzyme was Lys-GST and the substrate was *E. coli* tRNA$^{Lys}$. For □ symbols, the enzyme was Lys-GST and the substrate was crude tRNA from *Saccharomyces cerevisiae* (yeast). For Δ symbols, the enzyme was Lys tRS and the substrate was *E. coli* tRNA$^{Lys}$. For ● symbols, the enzyme was Lys tRS and the substrate was crude tRNA from *S. cerevisiae*. For + symbols, the enzyme was Lys tRS and no substrate tRNA was added.

Figure 7:
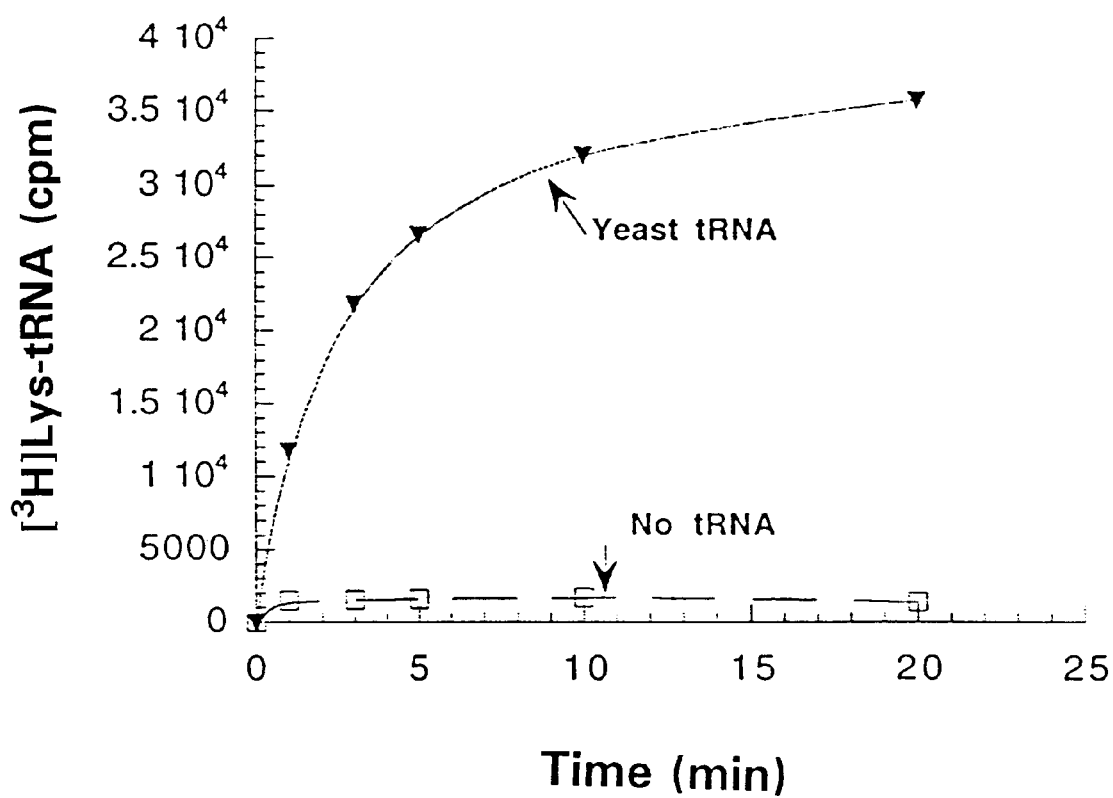

FIG. 7 is a graph showing aminoacylation of yeast tRNA with [$^3$H]-tyrosine by *P. carinii* tyrosyl-tRNA synthetase expressed as a GST fusion protein in *E. coli*. Activity assay conditions are described in Example 14. In this assay, the concentration of the GST-TyrRS fusion protein is approximately 70 nM.

DETAILED DESCRIPTION OF THE INVENTION

The aminoacyl-tRNA synthetases are enzymes with the common general function of catalyzing the following reaction:

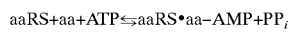

(aaRS=aminoacyl-tRNA synthetase; aa=amino acid; ATP=adenosine 5'-triphospate, AMP=adenosine 5'-monophosphate; PP$_i$=inorganic pyrophosphate) The second (aminoacylation) step is often referred to as "charging" the tRNA.

Generally, in each eucaryotic organism, there are 20 different cytoplasmic aaRSs, one specific for each amino acid. Eucaryotic organisms also generally encode a separate set of mitochondrial aaRss. In the yeast *Saccharomyces cerevisiae*, the cytoplasmic and mitochondrial enzymes are encoded by separate nuclear genes, with the exception of histidyl and valyl-tRNA synthetases (Natsoulis, G., et al. *Cell* 46:235–243 (1986); Chatton, B. et al., *J. Biol. Chem.* 263:52–57 (1988)). Each aminoacyl-tRNA synthetase enzyme recognizes and reacts with a specific amino acid and with one or more tRNAs that recognize the codons specific for that amino acid (cognate tRNAs). The specificity of the aaRS for the amino acid is determined by protein-amino acid interactions, and the specificity of the aaRS for the tRNA is determined by protein-RNA interactions, using different sites on the aaRS.

The tRNA synthetases can be subdivided into two groups of enzymes, class I and class II, based on short regions of sequence homology as well as distinct active site core tertiary structures (Eriani, G., et al., *Nature* 347:203–206 (1990); Moras, D., *Trends Biochem. Sci.* 17:159–164 (1992)). The twenty tRNA synthetases have been divided into two classes of ten enzymes each (see, e.g., Burbauma, J. J. and P. Schimmel, *J. Biol. Chem.* 266(26):16965–16968 (1991)).

Nucleic Acids, Constructs and Vectors

The present invention relates to isolated and/or recombinant (including, e.g., essentially pure) nucleic acids having sequences which encode a pneumocystis aminoacyl-tRNA synthetase, or a portion of a pneumocystis aminoacyl-tRNA synthetase. In one embodiment, the nucleic acid or portion thereof encodes a protein or polypeptide having at least one function characteristic of a pneumocystis aminoacyl-tRNA synthetase specific for a selected amino acid, such as a catalytic activity (e.g., catalysis of aminoacyl-adenylate formation, catalysis of aminoacylation of a tRNA with the amino acid,) and/or binding function (e.g., tRNA-, amino acid- or ATP-binding) and/or oligomerization function. (Oligomerization activity is the ability of a protein subunit or protein fragment to bind together with one or more other protein subunits or protein fragments, thus altering the quaternary structure of the resulting complex. For example, "adhesive" fragments with oligomerization activity can bind to another fragment with no catalytic activity of its own to restore or partially restore enzymatic activity (Jasin, M., et al., U.S. Pat. No. 4,952,501)). The present invention also relates more specifically to isolated and/or recombinant nucleic acids or a portion thereof having sequences which encode an aminoacyl-tRNA synthetase of *Pneumocystis carinii* origin, or a portion thereof.

The invention further relates to isolated and/or recombinant nucleic acids that are characterized by (1) their ability to hybridize to (a) a nucleic acid encoding a pneumocystis aminoacyl-tRNA synthetase specific for a selected amino acid, such as that nucleic acid having the sequence SEQ ID NO:40, SEQ ID NO:44, SEQ ID NO:42, SEQ ID NO:36, or SEQ ID NO:38, to (b) the complement of (a), or (c) to portions of either of the preceding, (2) by their ability to encode a polypeptide having the amino acid sequence of a pneumocystis aminoacyl-tRNA synthetase, such as the amino acid sequence SEQ ID NO:41 or SEQ ID NO:45, or functional equivalents thereof (e.g., a polypeptide which aminoacylates the isoaccepting cognate amino acid tRNAs (such as $tRNA^{Lys}$, $tRNA^{Tyr}$, $tRNA^{Ile}$, $tRNA^{Met}$, or $tRNA^{Ala}$ of P. carinii) with a selected amino acid), or (3) by both characteristics. In one embodiment, the percent amino acid sequence similarity between the polypeptides having the amino acid sequences encoded by SEQ ID NO:40 and 44 and by the P. carinii coding sequences of SEQ ID NO:42, 36 and 38, and the respective functional equivalents of these polypeptides is at least about 80% ($\geq 80\%$). In a preferred embodiment, the respective functional equivalents of the amino acid sequences encoded by SEQ ID NO:40 and 44 and by the P. carinii coding sequences of SEQ ID NO:42, 36 and 38, share at least about 85% sequence similarity with the polypeptides having the amino acid sequences encoded by SEQ ID NO:40 and 44 and by the P. carinii coding sequences of SEQ ID NO:42, 36 and 38. More preferably, the percent amino acid sequence similarity between the polypeptides having the amino acid sequences encoded by SEQ ID NO:40 and 44 and by the P. carinii coding sequences of SEQ ID NO:42, 36 and 38, and the respective functional equivalents of these polypeptides is at least about 90%, and still more preferably, at least about 95%. Isolated and/or recombinant nucleic acids meeting these criteria comprise nucleic acids having sequences identical to sequences of naturally occurring pneumocystis aaRSs and portions thereof, or variants of the naturally occurring sequences. Such variants include mutants differing by the addition, deletion or substitution of one or more residues, modified nucleic acids in which one or more residues are modified (e.g., DNA or RNA analogs), and mutants comprising one or more modified residues.

Such nucleic acids can be detected and isolated under high stringency conditions or moderate stringency conditions, for example. "High stringency conditions" and "moderate stringency conditions" for nucleic acid hybridizations are explained on pages 2.10.1–2.10.16 (see particularly 2.10.8–11) and pages 6.3.1–6 in Current Protocols in Molecular Biology (Ausubel, F. M. et al., eds., Vol. 1, Suppl. 26, 1991), the teachings of which are hereby incorporated by reference. Factors such as probe length, base composition, percent mismatch between the hybridizing sequences, temperature and ionic strength influence the stability of nucleic acid hybrids. Thus, high or moderate stringency conditions can be determined empirically, depending in part upon the characteristics of the known DNA to which other unknown nucleic acids are being compared for sequence similarity.

Isolated and/or recombinant nucleic acids that are characterized by their ability to hybridize to a nucleic acid encoding a pneumocystis aminoacyl-tRNA synthetase (for example, those nucleic acids having the sequence in SEQ ID NO:40, 44, 42, 36 or 38) or to the complement of such nucleic acids (e.g. under high or moderate stringency conditions), may further encode a protein or polypeptide having at least one function characteristic of a pneumocystis aminoacyl-tRNA synthetase specific for a selected amino acid, such as a catalytic activity (e.g., aminoacyl-adenylate formation, aminoacylation of a tRNA with amino acid), binding function (e.g., tRNA-, amino acid-, or ATP-binding), antigenic function (e.g., binding of antibodies that also bind to non-recombinant pneumocystis aaRS) and/or oligomerization function. The catalytic or binding function of a protein or polypeptide encoded by hybridizing nucleic acid may be detected by standard enzymatic assays for activity or binding (e.g., assays which monitor aminoacyl-adenylate formation, aminoacylation of tRNA). Functions characteristic of the aminoacyl-tRNA synthetase may also be assessed by in vivo complementation activity or other suitable methods. Enzymatic assays, complementation tests, or other suitable methods can also be used in procedures for the identification and/or isolation of nucleic acids which encode a polypeptide such as a polypeptide of the amino acid sequence SEQ ID NO:41 or SEQ ID NO:45 or functional equivalents of these polypeptides. The antigenic properties of proteins or polypeptides encoded by hybridizing nucleic acids can be determined by immunological methods employing antibodies that bind to a pneumocystis aminoacyl-tRNA synthetase, such as immunoblot, immuno-precipitation and radioimmunoassay.

Nucleic acids of the present invention can be used in the production of proteins or polypeptides. For example, DNA containing all or part of the coding sequence for a pneumocystis tyrosyl-tRNA synthetase, or DNA which hybridizes to the DNA having the sequence SEQ ID NO:44, can be incorporated into various constructs and vectors created for further manipulation of sequences or for production of the encoded polypeptide in suitable host cells Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also these that result from recombination events that occur through the natural mechanisms of cells, but are selected for after the introduction to the cells of nucleic acids designed to allow and make probable a desired recombination event.

Portions of the isolated nucleic acids which code for polypeptides having a certain function can be identified and isolated by, for example, the method of Jasin, M., et al., U.S. Pat. No. 4,952,501. The aminoacyl-tRNA synthetases are known to have different quaternary structures, including both monomeric and multimeric structures (e.g., homodimers, tetramers and heteromultimeric $\alpha_2\beta_2$ forms). Thus, as used herein, a nucleic acid which encodes a portion of a pneumocystis aminoacyl-tRNA synthetase can also refer to one of two or more distinct subunits of said tRNA synthetase.

A further embodiment of the invention is antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acid can inhibit the expression of the gene encoded by the sense strand. Antisense nucleic acids can be produced by standard techniques.

In a particular embodiment, the antisense nucleic acid is wholly or partially complementary to and can hybridize with a target nucleic acid, wherein the target nucleic acid can hybridize to a nucleic acid having the sequence of the complement of the sequences shown in SEQ ID NO:36, 38, 40, 42 or 44. For example, antisense nucleic acid can be complementary to a target nucleic acid having the sequence shown in SEQ ID NO:36, 38, 40, 42 or 44 or to a portion thereof sufficient to allow hybridization. In another embodiment, the antisense nucleic acid is wholly or partially complementary to and can hybridize with a target nucleic acid which encodes a pneumocystis aminoacyl-tRNA synthetase.

Proteins

The invention also relates to proteins or polypeptides encoded by nucleic acids of the present invention. The proteins and polypeptides of the present invention can be isolated and/or recombinant. Proteins or polypeptides referred to herein as "isolated" are proteins or polypeptides purified to a state beyond that in which they exist in cells. "Isolated" proteins or polypeptides include proteins or polypeptides obtained by methods described herein, similar methods or other suitable methods, including essentially pure proteins or polypeptides, proteins or polypeptides produced by chemical synthesis, or by combinations of biological and chemical methods, and recombinant proteins or polypeptides which are isolated. Proteins or polypeptides referred to herein as "recombinant" are proteins or polypeptides produced by the expression of recombinant nucleic acids.

In a preferred embodiment, the protein or portion thereof has at least one function characteristic of a pneumocystis aminoacyl-tRNA synthetase specific for a selected amino acid for example, antigenic function (e.g., binding of antibodies that also bind to non-recombinant pneumocystis aminoacyl-tRNA synthetase), catalytic activity (e.g., catalysis of aminoacyl-adenylate formation, catalysis of aminoacylation of a tRNA with amino acid) binding function (e.g., tRNA-, amino acid-, or ATP-binding) and/or oligomerization activity.

As such, these proteins are referred to as aminoacyl-tRNA synthetases of pneumocystis origin or pneumocystis aminoacyl-tRNA synthetases, and include, for example, naturally occurring pneumocystis aminoacyl-tRNA synthetases, variants (e.g. mutants) of those proteins and/or portions thereof. Such variants include mutants differing by the addition, deletion or substitution of one or more amino acid residues, or modified polypeptides in which one or more residues are modified, and mutants comprising one or more modified residues.

In a particularly preferred embodiment, like naturally occurring pneumocystis aminoacyl-tRNA synthetases, isolated and/or recombinant pneumocystis aminoacyl-tRNA synthetases of the present invention aminoacylate the isoaccepting cognate tRNAs of the pneumocystis organism with the amino acid in a two-step reaction. For example, in the case of $P.$ carinii, an isolated, recombinant lysyl-tRNA synthetase is able to aminoacylate each of the isoaccepting species of cognate tRNA$^{Lys}$ of $P.$ carinii with lysine. In the first step, the lysyl-tRNA synthetase catalyzes the covalent linkage of lysine to ATP to form an adenylate complex (lysyl-adenylate) with the release of pyrophosphate, and, in a second step, catalyzes the covalent linkage of lysine to a specific tRNA recognized by the enzyme, releasing AMP.

The invention further relates to fusion proteins, comprising a pneumocystis aminoacyl-tRNA synthetase (as described above) as a first moiety, linked to second moiety not occurring in the enzyme as found in nature. Thus, the second moiety can be an amino acid or polypeptide. The first moiety can be in an N-terminal location, C-terminal location or internal to the fusion protein. In one embodiment, the fusion protein comprises a $P.$ carinii aminoacyl-tRNA synthetase as the first moiety, and a second moiety comprising a linker sequence, and affinity ligand.

Fusion proteins can be produced by a variety of methods. For example, a fusion protein can be produced by the insertion of an aaRS gene or portion thereof into a suitable expression vector, such as Bluescript SK+/− (Stratagene), pGEX-4T-2 (Pharmacia) and pET-15b (Novagen). The resulting construct is then introduced into a suitable host cell for expression. Upon expression, fusion protein can be purified from a cell lysate by means of a suitable affinity matrix (see e.g., *Current Protocols in Molecular Biology* (Ausubel, F. M. et al., eds., Vol. 2, Suppl. 26, pp. 16.4.1–16.7.8 (1991)).

The invention also relates to isolated and/or recombinant portions of an aminoacyl-tRNA synthetase of pneumocystis origin. For example, a portion of an aminoacyl-tRNA synthetase can also refer to one of two or more distinct subunits of said tRNA synthetase. Portions of the enzyme can be made which have full or partial function on their own, or which when mixed together (though fully, partially, or nonfunctional alone), spontaneously assemble with one or more other polypeptides to reconstitute a functional protein having at least one function characteristic of an aminoacyl-tRNA synthetase. (see, e.g., Shiba, K. and Schimmel, P., *J. Biol. Chem.* 267:22703–22706 (1992) for an example of three inactive peptides from *E. coli* IleRS spontaneously assembling in vivo to reconstitute active enzyme; see also, Burbaum, J. and Schimmel, P., *Biochemistry* 30(2): 319–324 (1991), describing non-overlapping segments of *E. coil* MetRS that can fold together to reconstitute an active enzyme capable of recognizing and charging tRNA in vitro and in vivo; see also Jasin, M. et al. (U.S. Pat. No. 4,952, 501) describing deletion studies of *E. coli* alanyl-tRNA synthetase which showed that large portions of the protein were unnecessary for specific aminoacylation activity.) Based on this type of analysis, portions of a pneumocystis aaRS can be made which have at least one function characteristic of a pneumocystis aminoacyl-tRNA synthetase, such as catalytic, binding function, antigenic function and/or oligomerization function. Studies on the structure and function of the aaRSs provide the basis for being able to divide the pneumocystis aaRS enzymes into functional domains (Schimmel, P., *Current Biology* 1:811–816 (1991)).

The sequences and structures of the catalytic domain of tRNA synthetases already purified and studied are the basis for dividing them into two distinct classes of ten enzymes each, class I and class II (Schimmel, P., *Ann. Rev. Biochem.* 56:125–158 (1987); Webster, T. A., et al., *Science* 226:1315–1317 (1984); Eriani, G. et al, *Nature* 347:203–206 (1990) and Cusack, S., et al., *Nature* 347:249–255 (1990)).

Class I enzymes have a well-conserved H-terminal nucleotide binding fold repsonsible for amino acid binding, aminoacyl-adenylate formation, and tRNA acceptor helix docking. The N-terminal nucleotide binding fold is comprised of alternating β-strands and α-helices and a C-terminal domain that is rich in α-helices and that contains residues needed for interactions with the parts of the tRNA distal to the amino acid attachment site (Shepard, A., et al., *Proc. Natl. Acad. Soc. U.S.A.* 89:9964–9968 (1992); Hou, Y.-M., et al., *Proc. Natl. Acad. Sci. U.S.A.* 88:976–980 (1991)). Five enzymes—cysteinyl-, isoleucyl-, leucyl-, methionyl-, and valyl-tRNA synthetases—have been grouped together because they are more closely related in sequence and arrangement of their domains to each other than to the other five members of class I (Hou, Y.-M., et al., *Proc. Natl. Acad. Sci. U.S.A.* 88:976–980 (1991), Eriani, G., et al., *Nucleic Acids Res.* 19:265–269 (1991)). Furthermore, the C-terminal domains of isoleucyl-, leucyl-, methionyl-, cysteinyl- and valyl-tRNA synthetases appear to have a common origin, which is distinct from the C-terminal domain found in other class I enzymes (Shiba, K., et al., *Proc. Natl. Acad. Sci. U.S.A.* 89:1880–1884 (1992); Shepard, A., et al., *Proc. Natl. Acad. Sci. U.S.A.* 89:9964–9968 (1992)). In *E. coli*, these five enzymes of class I vary in size from 461 to 951 amino acids and are active as monomers. The size variation is in large part explained by the variability in the lengths of the two insertions designated connective polypeptide 1 (CP1) which is inserted between the second α-helix and third β-strand of the nucleotide binding fold, and CP2, which is placed between the third α-helix and fourth β-strand (Starzyk, R. M., et al., *Science* 237:1614–1618 (1987)). In all of these enzymes, CP1 is the larger of the two insertions and varies in *E. coli* from 61 in cysteinyl-tRNA synthetase to 300 amino acids in isoleucyl-tRNA synthetase (Hou, Y.-M., et al., *Proc. Natl. Acad. Sci. U.S.A.* 88:976–980 (1991)). While a portion of CP1 may be deleted from isoleucyl-tRNA synthetase without loss of function (Starzyk, R. K., et al., *Science* 237:1614–1618 (1987)), this insertion is known to facilitate acceptor helix interactions in the related glutaminyl-tRNA synthetase whose three dimensional structure in complex with tRNA$^{Gln}$ has been determined by x-ray crystallography (Rould, M. A et al., *Science* 246:1135–1142 (1989)). In some tRNA synthetases, this second domain interacts directly with the anticodon (Rould, M. A. et al., *Science* 246:1135–1142 (1989) and Cavarelli, J., et al., *Nature* 362:181–184 (1993)), while in other enzymes there is no contact made between the second domain and the anticodon (Biou, V., et al., *Science* 263:1404–1410 (1994)). To a first approximation, the two domains in class I tRNA synthetases interact with the two distinct domains of the L-shaped tRNA structure. Thus, the recognition elements of the tRNA synthetase and of the tRNA which are needed for the operational RNA code are segregated into discrete protein and RNA domains.

The primary sequence of the class II enzymes can be characterized by three motifs. These motifs are designated in the order they occur in the sequence as motif 1, motif 2, and motif 3. Although the motifs have a conserved core, they vary in length and are marked by as little as a single invariant amino acid residue. The motif sequences are defined as follows:

Motif 1: gΦxxΦxPΦΦ

Motif 2: (F/Y/H)Rx(E/D)(4–12x)(R/H)xxxFxxx(D/E)

Motif 3: λxΦgΦgΦeRΦΦΦΦΦ

The abbreviations are: x, variant; Φ, hydrophobic; and λ, small amino acids. Lower case letters indicate that the amino acid is partially conserved. None of these motifs are found in the class I family. With the exception of *E. coli* Gly- and Phe-tRNA synthetases which only contain a discernible motif 3, class II enzymes characacterized to date incorporate all three motifs (Ribas de Pouplanae, L. et al., *Protein Science* 2:2259–2262 (1993)).

The second class of tRNA synthetases was firmly defined when the crystal structure of the *E. coli* Ser-tRNA synthetase active site was shown to have no relationship to the Rossmann fold of class I enzymes (Cusack, S. C., et al., *Nature* 347:249–255 (1990)) X-ray diffraction investigations with an ATP-bound Ser-tRNA synthetase co-crystal from *T. thermophilus* revealed the details of a novel ATP binding site (Cusack, S., et al., in *The Translational Apparatus*, K. H. Nierhaus et al., eds., Plenum Press, New York, pp. 1–9, 1993; Belrhali, H., et al., *Science* 263:1432–1436 (1994); Biou, V., et al., *Science* 263:1404–1410 (1994)).

Motif 3 is comprised of a β-strand followed by an α helix and is characterized by a GLER sequence. This motif is the only one that has been universally detected in all of the class II enzymes studied. The crystal structures of yeast Ser- and Asp- (Ruff, M. S. et al., *Science* 252:1682–1689 (1991)) tRNA synthetases suggest a role for motif 3 in amino acid and ATP binding. Mutations in this region have resulted in a reduction in binding and/or a high $K_m$ for amino acid or ATP binding (Eriani, G., et al., *Nature* 347:203–206 (1993); Anselme, J. and Härtlein, M., *FEBS Lett.* 280:163–166 (1991); Kast, P. and Hennecke, H., *J. Mol. Biol.,* 222:99–124 (1991); Kast, P. et al., *FEBS Lett.* 293:160–163 (1991); Lanker, S., et al., *Cell* 70:647–657 (1992)).

Yeast Asp-tRNA synthetase was the first class II enzyme to be co-crystallized with its cognate tRNA (Ruff, M., et al., *Science* 252:1682–1689 (1991)). The yeast Asp-tRNA synthetase contains a nucleotide binding structure similar to that found in Ser-tRNA synthetase. The combination of these two class II crystal structures provides a model for the active sites of all of the class II tRNA synthetases.

Because motif 1 is at the dimer interface in the crystal structures of yeast Asp-tRNA synthetase (Ruff, M. S., et al., *Science* 252:682–1689 (1991) and *E. coli* Ser-tRNA synthetase (Cusack, S., et al., *Nature* 347:249–255 (1990); Cusack, S., et al., In *The Translational Apparatus*, K. H. Nierhaus et al., eds., Plenum Press, New York, pp. 1–9, 1993; Price, S., et al., *FEBS Lett.* 324:167–170 (1993)) and *T. thermophlius* Ser-tRNA synthetase (Cusack, S., et al., In *The Translational Apparatus*, K. H. Nierhaus et al., eds., Plenum Press, New York, pp. 1–9, 1993; Belrhali, H., et al., *Science* 263:432–1436 (1994); Biou V., et al., *Science* 263:1404–1410 (1994)), motif 1 was thought to be important for dimerization. This motif was identified in the N-terminal region of *E. coli* Ala-tRNA synthetase (Ribas de Pouplana, et al., *Protein Science* 2:2259–2262 (1993)), but a series of deletion mutations had also previously demonstrated that a region at the C-terminus of the protein is needed for oligomerization (Jasin, H., et al., *Nature* 306:441–447 (1983); Jasin, et al., *Cell* 36:1089–1095 (1984)). Thus, motif 1 is not sufficient for oligomerization of this enzyme.

An idiographic representation of the predicted eight-stranded β-structure with three α-helices of the *E. coli* Ala-tRNA synthetase has been constructed (Ribas de Pouplana, L., et al., *Protein Science* 2:2259–2262 (1993)); Shi, J.-P., et al., *Biochemistry* 33:5312–5318 (1994)). Collectively, over 40 mutations in motif 2 and the region between motif 2 and 3 were individually constructed and tested (Davis, M. W., et al., *Biochemistry* 33:9904–9911 (1994); Shi, J.-P., et al., *Biochemistry* 33:5312–5318 (1994)). These mutations were mostly at conserved residues with chemical functional groups. Although motif 2 is of a different size and has only two identical amino acid residues with its counterpart in yeast Asp- and *T. thermophilus* Ser-tRNA synthetases, the mutational analysis of this motif can be explained in terms of those structures, and shows the importance of predicted motif 2 for adenylate synthesis (Ribas de Pouplana, L., et al., *Protein Science* 2:2259–2262 (1993)). A study of the products of random mutagenesis of this region also demonstrated the importance of motif 2 for adenylate transfer (Lu, Y. and Hill, K. A. W., *J. Biol. Chem.* 269:12137–12141 (1994)). Mutagenesis of specific residues in motif 2 of *E. coli* Ala-tRNA synthetase and mutagenesis of their predicted counterparts in motif 2 of yeast Asp-tRNA synthetase yielded similar results with regard to loss of function (Cavarelli, J., et al., *EMBO J.* 13:327–337 (1994); Davis, M. W., et al., *Biochemistry* 33:9904–9911 (1994)). Evidence was obtained for sequence context determining how the energy of adenylate binding is partitioned between ground and transition states in the two enzymes. In addition, a conserved aspartate residue among Ala-tRNA synthetases at the beginning of motif 3 was shown to be important for the adenylate synthesis and particularly for the adenylate transfer reaction (Davis, M. W., et al., *Biochemistry* 33:9904–9911 (1994)). The functional significance of motif 3 for adenylate synthesis has been demonstrated by mutagenesis in the yeast Asp-tRNA synthetase system (Cavarelli, J., et al., *EMBO J.* 13:327–337 (1994)).

Upon consideration of this information, with the remaining teachings of the specification, *P. carinii* tRNA synthetase derivatives can be constructed which possess at least one function characteristic of a pneumocystis aminoacyl tRNA synthetase.

Method of Producing Recombinant aaRSs

Another aspect of the invention relates to a method of producing the pneumocystis aminoacyl-tRNA synthetase or a portion thereof and expression systems and host cells containing a vector appropriate for expression of the aminoacyl-tRNA synthetase.

Cells that express a recombinant aminoacyl-tRNA synthetase or a portion thereof can be made and grown in culture to produce the enzyme for isolation and purification. These cells can be procaryotic or eucaryotic. Examples of procaryotic cells that can be used to express pneumocystis aminoacyl-tRNA synthetases include *Escherichia coli, Bacillus subtilis* and other bacteria. Examples of eucaryotic cells that can be used to express the aminoacyl-tRNA synthetases include yeasts such as *Saccharomyces cerevisiae,* and other lower eucaryotic cells, and cells of higher eucaryotes such as those from insects and mammals (See, e.g., Ausubel, F. M. et al., eds. *Current Protocols in Molecular Biology,* Greene Publishing Associates and John Wiley & Sons Inc., (1993)).

To make host cells that produce a recombinant aaRS protein or portion thereof for isolation and purification, as a first step the gene encoding the enzyme can be inserted into a nucleic acid vector, e.g., a DNA vector, such as a plasmid, virus or other suitable replicon, which can be present in a single copy or multiple copies, or the gene can be integrated in a host cell chromosome. Such a suitable replicon contains all or part of the coding sequence for aminoacyl-tRNA synthetase, and has the coding sequence under the control of transcription signals and linked to appropriate translation signals to permit translation of the aaRS, portion thereof, or of a fusion protein comprising aaRS or portion thereof. As a second step, the vector can then be introduced into cells by a method appropriate to the type of host cells (e.g., transformation, electroporation, infection). In a third step, for expression from the aaRS gene, the host cells can be maintained under appropriate conditions, e.g., in the presence of inducer, normal growth conditions, etc.).

As a particular example of the above approach to producing active pneumocystis aminoacyl-tRNA synthetase, a gene encoding the *P. carinii* aaRS can be integrated into the genome of a virus that enters the host cells. By infection of the host cells, the components of a system which permits the transcription and translation of the pneumocystis aaRS gene are present in the host cells. Alternatively, an RNA polymerase gene, inducer, or other component required to complete such a gene expression system may be introduced into the host cells already containing the pneumocystis aaRS gene, for example, by means of a virus that enters the host cells and contains the required component. The aaRS gene can be under the control of an inducible or constitutive promoter. The promoter can be one that is recognized by the host cell RNA polymerase. The promoter can, alternatively, be one that is recognized by a viral RNA polymerase and is transcribed following infection of the host cells with a virus.

Antibodies

The invention further relates to antibodies that bind to an isolated and/or recombinant pneumocystis aminoacyl-tRNA synthetase, including portions of antibodies (e.g., a peptides), which can specifically recognize and bind to the tRNA synthetase. These antibodies can be used in methods to purify the enzyme or portion thereof by various methods of immunoaffinity chromatography, or to selectively inactivate one of the enzyme's active sites, or to study other aspects of the enzyme's structure, for example.

The antibodies of the present invention can be polyclonal or monoclonal, and, the term antibody is intended to encompass both polyclonal and monoclonal antibodies. Antibodies of the present invention can be raised against an appropriate immunogen, including proteins or polypeptides of the present invention, such as an isolated and/or recombinant pneumocystis aminoacyl-tRNA synthetase or portions thereof, or synthetic molecules, such as synthetic peptides. The immunogen, for example, can be a protein having at least one function of a pneumocystis aminoacyl-tRNA synthetase, as described herein.

The term antibody is also intended to encompass single chain antibodies, chimeric, humanized or primatized (CDR-grafted) antibodies, as well as chimeric or CDR-grafted single chain antibodies, comprising portions from more than one species. For example, the chimeric antibodies can comprise proteins derived from two different species, joined together chemically by conventional techniques or prepared as a single contiguous protein using genetic engineering techniques (e.g., DNA encoding the protein portions of the chimeric antibody can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., *BioTechnology,* 10: 1455–1460 (1992), regarding primatized antibody, and Ladner et al., U.S. Pat. No. 4,946,778 and Bird, R. E. et al., *Science,* 242: 423–426 (1988)) regarding single chain antibodies.)

Whole antibodies and biologically functional fragments thereof are also encompassed by the term antibody. Biologically functional antibody fragments which can be used include those fragments sufficient for binding of the antibody fragment to a pneumocystis aaRS to occur, such as Fv, Fab, Fab' and $F(ab')_2$ fragments. Such fragments can be produced by enzymatic cleavage or by recombinant techniques. For instance, papain or pepsin cleavage can generate Fab or $F(ab')_2$ fragments, respectively. Alternatively, antibodies can be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the CH$_1$ domain and hinge region of the heavy chain.

Preparation of immunizing antigen, and polyclonal and monoclonal antibody production can be performed using any suitable technique. A variety of methods have been described (see e.g., Kohler et al., *Nature,* 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual,* (Cold Spring Harbor Laboratory: Cold Spring Harbor, N.Y.); *Current Protocols In Molecular Biology,* Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0) with antibody producing cells. The antibody producing cell, preferably those obtained from the spleen or lymph nodes, are obtained from animals immunized with the antigen of interest. The fused cells (hybridomas) are isolated using selective culture conditions, and cloned by limiting dilution. Cells which produce antibodies with the desired specificity are selected by a suitable assay (e.g., ELISA).

Assays for Inhibitors and Tester Strains

The enzymatic assays, binding assays, and construction of tester strains described below, which rely upon the nucleic acids and proteins of the present invention, can be used, alone or in combination with each other or other suitable methods, to identify inhibitors of one or more aminoacyl-tRNA synthetases.

Enzyme Assay

Upon the isolation of an aaRS gene from pneumocystis (as described herein), the gene can then be incorporated into an expression system for production of the aaRS, followed by isolation and testing of the enzyme in vitro. The isolated or purified pneumocystis aaRSs can also be used in further structural studies that will allow for the design of antibiotics which specifically target the aaRS of pneumocystis, while not affecting or minimally affecting the mammalian (e.g., human) aaRSs. The design of these drugs will exploit the structural differences between the pathogen aaRS and the aaRSs of mammals, such as humans.

Furthermore, isolated, active pneumocystis aaRSs can be used in an in vitro method of screening for inhibitors of aminoacyl-tRNA synthetase activity in which the inhibitory effect of a compound is assessed by monitoring aaRS activity according to standard techniques. For example, inhibitors of the activity of isolated, recombinant *P. carinii* LysRS, TyrRS, IleRS, MetRS or AlaRS can be identified by the method. In one embodiment, the isolated aaRS enzyme is maintained under conditions suitable for aminoacyl-adenylate formation, the enzyme is contacted with a compound to be tested, and formation of the aminoacyl-adenylate is monitored by standard assay. A reduction in the activity measured in the presence of compound, as compared with the activity in the absence of compound, is indicative of inhibition of aminoacyl-tRNA synthetase activity by the compound. In another embodiment, formation of the aminoacylated tRNA is monitored in a standard aminoacylation assay. Inhibitors identified by enzymatic assay can be further assessed for antimicrobial activity using tester strains as described herein, or using other suitable assays.

Binding Assay

Isolated, recombinant aaRS or a portion thereof, and suitable fusion proteins can be used in a method to select and identify compounds which bind specifically to the aaRS, such as *P. carinii* lysyl-, tyrosyl-, isoleucyl-, methionyl- or alanyl-tRNA synthetase, and which are potential inhibitors of aaRS activity. Compounds selected by the method can be further assessed for their inhibitory effect on aaRS activity and for antimicrobial activity.

In one embodiment, isolated or purified *P. carinii* aaRS can be immobilized on a suitable affinity matrix by standard techniques, such as chemical cross-linking, or via an antibody raised against the isolated or purified aaRS and bound to a solid support. The matrix is packed in a column or other suitable container and is contacted with one or more compounds (e.g., a mixture) to be tested under conditions suitable for binding of compound to the aaRS. For example, a solution containing compounds is made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds. Alternatively, the elution buffer can comprise a release component or components designed to disrupt binding of compounds (e.g., one or more substrates or substrate analogs which can disrupt binding of compound to the aaRS, such as lysine, ATP, a tRNA or other suitable molecules which competitively inhibit binding).

Fusion proteins comprising all of, or a portion of, the aaRS linked to a second moiety not occurring in the pneumocystis aaRS as found in nature (see above), can be prepared for use in another embodiment of the method. Suitable fusion proteins for this purpose include those in which the second moiety comprises an affinity ligand (e.g., an enzyme, antigen, epitope). The fusion proteins can be produced by the insertion of an aaRS gene or portion thereof into a suitable expression vector, which encodes an affinity ligand (e.g., pGEX-4T-2 and pET-15b, encoding glutathione S-transferase and His-Tag affinity ligands, respectively). The expression vector is introduced into a suitable host cell for expression. Host cells are lysed and the lysate, containing fusion protein, can be bound to a suitable affinity matrix by contacting the lysate with an affinity matrix under conditions sufficient for binding of the affinity ligand portion of the fusion protein to the affinity matrix.

In one aspect of this embodiment, the fusion protein is immobilized on a suitable affinity matrix under conditions sufficient to bind the affinity ligand portion of the fusion protein to the matrix, and is contacted with one or more compounds (e.g., a mixture) to be tested, under conditions suitable for binding of compounds to the aaRS portion of the bound fusion protein. Next, the affinity matrix with bound fusion protein is washed with a suitable wash buffer to remove unbound compounds and non-specifically bound compounds. Compounds which remain bound can be released by contacting the affinity matrix with fusion protein bound thereto with a suitable elution buffer (a compound elution buffer). Wash buffer is formulated to permit binding of the fusion protein to the affinity matrix, without significantly disrupting binding of specifically bound compounds. In this aspect, compound elution buffer is formulated to permit retention of the fusion protein by the affinity matrix, but is formulated to interfere with binding of the compound (s) tested to the aaRS portion of the fusion protein. For example, a change in the ionic strength or pH of the elution buffer can lead to release of compounds, or the elution buffer can comprise a release component or components designed to disrupt binding of compounds to the aaRS portion of the fusion protein (e.g., one or more substrates or substrate analogs which can disrupt binding of compounds to the aaRS portion of the fusion protein, such as lysine, ATP, or tRNA$^{Lys}$ for LysRS, or other suitable molecules which competitively inhibit binding).

Immobilization can be performed prior to, simultaneous with, or after contacting the fusion protein with compound, as appropriate. Various permutations of the method are possible, depending upon factors such as the compounds tested, the affinity matrix-ligand pair selected, and elution buffer formulation. For example, after the wash step, fusion protein with compound bound thereto can be eluted from the affinity matrix with a suitable elution buffer (a matrix elution buffer, such as glutathione for a GST fusion). Where the fusion protein comprises a cleavable linker, such as a thrombin cleavage site, cleavage from the affinity ligand can release a portion of the fusion with compound bound thereto. Bound compound can then be released from the fusion protein or its cleavage product by an appropriate method, such as extraction.

To enrich for specific binding to the aaRS portion of the fusion protein, compounds can be pre-treated, for example with affinity matrix alone, with affinity ligand or a portion thereof (e.g., the portion present in the fusion protein), either alone or bound to matrix, under conditions suitable for binding of compound to the aaRS portion of the bound fusion protein.

One or more compounds can be tested simultaneously according to the method. Where a mixture of compounds is tested, the compounds selected by the foregoing processes can be separated (as appropriate) and identified by suitable methods (e.g., PCR, sequencing, chromatography). Large combinatorial libraries of compounds (e.g., organic compounds, peptides, nucleic acids) produced by combinatorial chemical synthesis or other methods can be tested (see e.g., Ohlmeyer, M. H. J. et al., *Proc. Natl. Acad. Sci. U.S.A.* 90:10922–10926 (1993) and DeWitt, S. H. et al., *Proc. Natl. Acad. Sci. U.S.A.* 95:6909–6913 (1993), relating to tagged compounds; see also Rebek et al., Process for Creating Molecular Diversity, U.S. Ser. No. 08/180,215, filed Jan. 12, 1994, relating to compounds without tags; see also, Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible. Where compounds do not carry tags, chromatographic separation, followed by mass spectrophotometry to ascertain structure, can be used to identify individual compounds selected by the method, for example.

Random sequence RNA and DNA libraries see Ellington, A. D. et al., *Nature* 346: 818–822 (1990); Bock, L. C. et al., *Nature* 355: 584–566 (1992); and Szostak, J. W., *Trends in Biochem. Sci.* 17:89–93 (March, 1992)) can also be screened according to the present method to select RNA or DNA molecules which bind to a pneumocystis aaRS. Such molecules can be further assessed for antimicrobial effect upon introduction into a cell (e.g., by expression in the case of an RNA molecule selected by the method).

Tester Strains

Nucleic acids of the present invention can also be used in constructing tester strains for in vivo assays of the effect on the activity of the pneumocystis enzyme of a substance which is added to tester strain cells. A tester strain comprises a host cell having a defect in a gene encoding an endogenous aaRS, and a heterologous aaRS gene which complements the defect in the host cell genes. Thus, complementation of a particular defective host cell aaRS gene by a heterologous aaRS gene is a threshold requirement for a tester strain. Because the aaRS genes are essential, the heterologous gene can be introduced into the host cell simultaneously with inactivation of the host cell gene to preserve viability. Alternatively, the heterologous gene can be introduced into the host cell before inactivation or loss of the host cell gene. In this case, to test for complementation, the host cell is then subjected to some change in conditions (e.g., a change in temperature, growth medium, selection conditions) which causes inactivation or loss of either the host aaRS gene or gene product, or both.

If the heterologous gene complements the inactivated host cell gene, such a cell can be used in a test of whether a substance that is introduced into the cells for testing, can interact specifically with the heterologous tRNA synthetase (or a component in the pathway of the expression of the heterologous tRNA synthetase gene) to cause loss of function of the tested heterologous tRNA synthetase in those host cells. Thus, such cells are "tester strains". Successful cross-species complementation has been described already, for example, for yeast seryl-tRNA synthetase and for yeast isoleucyl-tRNA synthetase in *E. coli* (Weygand-Durasevic, I., et al., *Eur. J. Biochem* 214:869–877 (1993); Racher, K. I., et al., *J. Biol. Chem.* 266:17158–17164 (1991)).

In tester cells to be used in an assay for chemical substances that can inhibit the function of a specific aaRS, the gene for the aminoacyl-tRNA synthetase can, for example, physically replace the host cell aaRS gene or can be present in addition to a host aaRS gene that does not produce a functional product, and the heterologous gene whose gene product is to be tested complements the host gene. A substance to be tested is administered to the tester cells, and the viability or growth of such cells can be compared with that of cells of a suitable control.

Suitable host cells to test *Pneumocystis carinii* genes can be host cells of a species other than *P. carinii*. As a tester strain comprises a host cell comprising a heterologous aaRS gene (i.e., one from a heterologous species), a suitable host cell is heterologous with respect to the species from which the gene to be tested is isolated.

Examples of species which are suitable for use as hosts for the construction of tester strains are *E. coli, S. cerevisiae,* and *B. subtilis.* These species are especially amenable to genetic manipulation because of their history of extensive study.

Suitable host cells having a genotype useful for the construction of a tester strain can be constructed or selected using known methods. For example, both in *E. coli* and in *S. cerevisiae,* a first plasmid which contains a functional copy of a host chromosomal aaRS gene which is to be inactivated later, along with some selectable marker gene, can be constructed and introduced into cells. Then, an inactivating mutation can be caused in the chromosomal copy of the aaRS gene.

This can be accomplished, for instance, by causing or selecting for a double crossover event which creates a deletion and insertion. This can be done by introducing into the cells double-stranded DNA having regions of homology to the DNA flanking the target aaRS gene, and having between these regions a gene encoding a selectable marker, either on a suitable vector or as a DNA fragment, as appropriate (Jasin et al., U.S. Pat. No. 4,713,337; Schimmel, P., U.S. Pat. No. 4,963,487; Toth, M. J. and Schimmel, P., *J. Biol. Chem.* 261:6643–6646 (1986); Rothstein, R., *Methods* in *Enzymology* 194:281–301 (1991)). Such an approach simultaneously inserts a selectable marker and results in a deletion of the endogenous gene between the flanking sequences provided. Where needed to maintain viability, a compatible maintenance plasmid is provided encoding an endogenous or complementing aaRS.

A test plasmid which is compatible with the maintenance plasmid, and which contains the aaRS gene to be tested for complementation, can be introduced into the host cells. If the first plasmid has been constructed to have a mechanism to allow for inhibition of its replication (for example, a temperature sensitive replicon) or to have a mechanism by which cells containing the first plasmid can be selected against (by, for example, the use of 5-fluoroorotic acid to select against *S. cerevisiae* cells which have a first plasmid containing the URA3 gene), cells which survive by virtue of having a complementing aaRS gene on the second plasmid can be selected (Sikorsky, R. S. and Boeke, J. D., *Methods in Enzymology* 194:302–318 (1991)).

Causing or selecting for a double crossover event which creates a deletion and insertion can be used in itself as a one-step method of constructing a tester strain in which a native aaRS gene is replaced by the corresponding foreign gene whose gene product is to be tested. Endogenous recombination mechanisms have been used to advantage previously in *E. coli, B. subtilis,* and *S. cerevisiae* among other organisms. This method depends on the ability of the heterologous gene to be tested to complement the native corresponding aaRS gene. This can be done by introducing into the cells double-stranded DNA having regions of homology to the DNA flanking the target native aaRS gene, and having between these regions a gene encoding a selectable marker as well as the heterologous aaRS gene intended to replace the native aaRS gene. The survival of cells expressing the selectable marker is indicative of expression of the introduced heterologous aaRS gene and complementation of the defect in the endogenous synthetase.

For example, a tester strain useful for testing the effect of a compound on the function of IleRS expressed by an inserted *P. carinii* gene, can be constructed in a one-step method. Optional positive and negative controls for this cross-species transformation can be used to show that the resulting strain depends on the IleRS gene from *P. carinii* for growth and that this recombination event is not lethal. For example, *B. subtilis* cells made competent for transformation (Dubnau, D. and Davidoff-Abelson, R., *J. Mol. Biol.* 56:206–221 (1971)) can be transformed with a suitable construct, such as a linearized plasmid containing an insert. Generally, the construct includes a selectable marker gene for antibiotic resistance, or other suitable selectable marker. In one embodiment, a linearized plasmid which contains the *P. carinii* IleRS gene and an antibiotic resistance gene, situated between sequences homologous to the flanking sequences of the endogenous IleRS gene of the host cells, is used to transform the host cell. For a positive control, the linearized plasmid can be constructed in a similar fashion, except that the native *B. subtilis* IleRS gene replaces the *P. carinii* gene, such that a normal *B. subtilis* IleRS gene is located adjacent to the antibiotic resistance marker in the insert. As a negative control, the insert can be designed to contain only the flanking sequences and the antibiotic resistance marker, for example. Antibiotic resistant transformants are not expected upon transformation with the negative control construct, as homologous recombination with the construct results in deletion of the endogenous IleRS gene. Successful construction of a tester strain can also be confirmed by Southern analysis.

The yeast *S. cerevisiae* offers additional possibilities for genetic manipulations to create tester strains, relative to bacteria. Yeast integrating plasmids, which lack a yeast origin of replication, can be used for making alterations in the host chromosome (Sikorski, R. S. and Heiter, P., *Genetics,* 122:19–27 (1989), Gietz, R. D. and Sugino, A., *Gene,* 74:527–534 (1988)). In another embodiment, one-step gene disruptions can be performed in diploid cells using a DNA fragment comprising a copy of an aaRS gene containing a deletion of the aaRS gene and an insertion of a selectable marker in the deleted gene. A suitable fragment can be introduced into a diploid cell to disrupt a chromosomal copy of the yeast gene. Successful integration of the disrupted aaRS gene can be confirmed by Southern blotting and by tetrad analysis of the sporulated diploid cells. The diploid cells heterozygous for the disrupted aaRS gene provide a diploid host strain which can be transformed with a plasmid containing the heterologous aaRS gene. These cells can be sporulated and the haploid spores analyzed for rescue of the defective chromosomal aaRS by the heterologous aaRS gene.

Alternatively, those diploid cells that are found to contain one copy of the disrupted chromosomal aaRS gene, as well as one functional copy, can be transformed with a maintenance plasmid which contains a gene which complements the disruption, such as the corresponding wild type yeast aaRS gene, and which provides for a mechanism to select against survival of the cells containing this plasmid. These cells can then be made to sporulate to obtain a haploid null strain containing the disrupted chromosomal aaRS gene and the wild type gene on the maintenance plasmid. This haploid host strain can then be transformed with a test plasmid which expresses a heterologous aaRS gene, and the maintenance plasmid can be selected against by growing this strain under appropriate conditions.

Construction of a tester strain may start with the isolation of a mutant host strain which produces only an inactive tRNA synthetase specific for a particular amino acid, a tRNA synthetase which is conditionally inactivatible, or no tRNA synthetase at all specific for that amino acid. Because of studies on the structure and function of the aminoacyl-tRNA synthetases, a number of *E. coli* and *S. cerevisiae* strains have been constructed already that can serve as convenient starting materials for the making of tester strains, or whose construction procedures can serve as models for the making of similar mutant strains in *E. coli, S. cerevisiae* and other host organisms.

A number of *E. coli* strains have been characterized in which an aaRS gene has been inactivated by some method, in whole or in part, yielding an observable phenotypic defect which can be detectably complemented. For example, null strains in which the gene encoding MetRS has been inactivated, and a mutant strain of *E. coli* in which the gene encoding MetRS has been conditionally inactivated, have been described (see Kim, et al., *Proc. Natl. Acad. Sci. U.S.A.* 90:10046–10050 (1993), describing a metG null strain of *E. coli* carrying a maintenance plasmid, MN9261/pRMS615); and Barker, D. G. et al. *Eur. J. Biochem.* 127:449–457 (1982) and Starzyk, R. M. et al., *Biochemistry,* 28:8479–8484 (1989), regarding a mutant strain having a methionine auxotrophy because the $K_m$ for methionine of the enzyme encoded by the chromosomal metG allele is elevated).

A plasmid such as the one reported by P. Walter et al. (*Proc. Natl. Acad. Sci. U.S.A.* 80:2437–2441, 1983), which contains the wild type cytoplasmic methionyl-tRNA synthetase gene of *S. cerevisiae,* MES1, can be the basis for the construction of mes1 strains, and for further construction of plasmids to create tester strains for a cytoplasmic MetRS.

Mitochondrial mutant strains such as the msm1-1 strain and disruption strain QBY43 (aW303ΔMSM1) (MATa ade2-1 his3-11, 15 leu2-3,112 ura3-1 trp1-1 msm1::HIS3; see Tzagoloff, A., et al., Eur. J. Biochem. 179:365–371 (1989)) can be used for the construction of yeast tester strains for testing a pneumocystis methionyl-tRNA synthetase.

Temperature sensitive alleles are examples of genes encoding conditionally inactivatable tRNA synthetases. For example, temperature-sensitive alleles of the genes encoding cytoplasmic IleRS (ils1-1) and MetRS (mes1-1) have been described in S. cerevisiae (Hartwell, L. H., and McLaughlin, C. S., J. Bacteriol. 96:1664–1671 (1968); McLaughlin, C. S., and Hartwell, L. H. Genetics 61:557–566 (1969)), and are available from the Yeast Genetic Stock Center (University of California-Berkeley; catalog nos. 341 and 19:3:4, respectively). Temperature sensitive strains of E. coli having a defect in the tyrS gene encoding TyrRS (see, e.g., Bedouellle, H. and G. Winter, Nature 320:371–373 (1986)); and temperature-sensitive serS strains of E. coli have also been described (Low, B. et al., J. Bacteriol. 108:742–750 (1971); Clarke, S. J. et al., J. Bacteriol. 113:1096–1103 (1973)).

Temperature-sensitive alaS strains of E. coli have been described (Buckel, P. et al, J. Bacteriol. 108:1008–1016 (1971); Lee, A. L. and Beckwith, J., J. Bacteriol. 166:878–883 (1986)), in addition to a number of strains with well-characterized alas deletions and complementing alas alleles on plasmids (Jasin, M., et al., Cell 36:1089–1095 (1984); Jasin, M. and Schimmel, P., J. Bacteriol. 159:783–786 (1984)). Such strains can be used as starting materials to construct E. coli tester strains for alanyl-tRNA synthetase genes of pneumocystis.

The gene (ILS1) encoding the cytoplasmic isoleucyl-tRNA synthetase of S. cerevisiae has been cloned into a shuttle vector and sequenced (Englisch, U., et al., Biol. Chem. Hoppe-Seyler 368:971–979 (1987)). The gene encoding isoleucyl-tRNA synthetase in E. coli has also been isolated and characterized (Webster, T. et al., Science 226:1315–1317 (1984)).

The gene for S. cerevisiae cytoplasmic lysyl-tRNA synthetase (KRS1) has been cloned and sequenced (Mirande, et al., Biochemie 68:1001–1007 (1986); Mirande, M. and Waller, J.-P. J. Biol. Chem. 263:18443–18451 (1988)). The gene was shown to be essential by the construction of a disrupted allele of KRS1 (Martinez, R. et al., Mol. Gen. Genet. 227:149–154 (1991)). The gene encoding S. cerevisiae mitochondrial lysyl-tRNA synthetase also has been cloned and characterized as being homologous in encoded amino acid sequence to both the E. coli and S. cerevisiae cytoplasmic lysyl-tRNA synthetases (Gatti, D. L. and A. Tzagoloff, J. Mol. Biol. 218:557–568 (1991)).

An E. coli strain has been constructed in which both genes encoding a lysyl-tRNA synthetase, lysS (Kawakami, K. et al., Mol. Gen. Genet. 229:333–340 (1989)) and lysU (Leveque, F. et al. Nucleic Acids Res. 18:305–312 (1990); Clark, R. L. and Neidhardt, F. C., J. Bacteriol. 172:3237–3243 (1990)), have been mutated. This strain carries a temperature sensitive maintainence plasmid that is lost at 42° C. (Chen, J. et al., J. Bacteriol. 176:2699–2705 (1994)).

The gene encoding the S. cerevisiae cytoplasmic tyrosyl-tRNA synthetase has been isolated by Chow and RajBhandary (J. Biol. Chem. 268:12855–12863, 1993). An S. cerevisiae strain has been constructed which carries a disruption of NSY1, the gene encoding mitochondrial tyrosyl-tRNA synthetase. Plasmids carrying NSY1 which rescue this defect, also have been constructed (Hill, J. and A. Tzagoloff, Columbia University; see Edwards, H. and P. Schimmel, Cell 51:643–649 (1987)).

E. coli strains having a defect, such as a null mutation, in the tyrosyl-tRNA synthetase gene can be constructed by making use of the E. coli tyrosyl-tRNA synthetase gene (Barker, D. G., Eur. J. Biochem., 125:357–360 (1982); Barker D. G. et al., FEBS Letters, 150:419–423 (1982)).

In S. cerevisiae, to construct a maintenance plasmid or a test plasmid carrying a heterologous gene, a suitable vector, such as a yeast centromere plasmid (CEN; single-copy) or 2' vector (high copy) can be used. A heterologous gene to be tested can also be incorporated into the chromosome, using an integrating plasmid, for example. Examples of convenient yeast vectors for cloning include vectors such as those in the pRS series (integrating, CEN, or 2' plasmids differing in the selectable marker (HIS3, TRP1, LEU2, URA3); see Christianson, T. W., et al., Gene, 110:119–122 (1992) regarding 2μ vectors; see Sikorski, R. S. and Hieter, P. Genetics, 122:19–27 (1989) regarding integrating and CEN plasmids which are available from Stratagene, La Jolla)) and shuttle vectors (integrating, CEN or 2μ vectors) which contain the multiple cloning site of pUC19 (Gietz, R. D. and Sugino, A., Gene, 74:527–534 (1988)). Examples of expression vectors include pEG (Mitchell, D. A. et al., Yeast, 9:715–723 (1993)) and pDAD1 and pDAD2, which contain a GAL1 promoter (Davis, L. I. and Fink, G. R., Cell 61:965–978 (1990)).

A variety of promoters are suitable for expression. Available yeast vectors offer a choice of promoters. In one embodiment, the inducible GAL1 promoter is used. In another embodiment, the constitutive ADH1 promoter (alcohol dehydrogenase; Bennetzen, J. L. and Hall, B. D., J. Biol. Chem., 257:3026–3031 (1982)) can be used to express an inserted gene on glucose-containing media. An example of a vector suitable for expression of a heterologous aaRS gene in yeast is pQB169 (see Example 15).

For illustration, a yeast tester strain can be constructed as follows. An S. cerevisiae strain with convenient markers, such as FY83 (MATa/MATα lys2-128δ/lys2-128δ leu2Δ1/leu2Δ1 ura3-52/ura3-52 trp1Δ63/trp1Δ63) can be used as a host cell.

A genomic clone encoding yeast cytoplasmic tyrosyl-tRNA synthetase has been isolated (p13Gen; Chow, C. M. and U. L. RajBhandary, J. Biol. Chem. 268(17):12855–12863 (1993); GenBank/EMBL Data Bank, Accession No. L12221-L12223). A genomic or cDNA clone encoding yeast cytoplasmic TyrRS can be used to create a null allele of the yeast cytoplasmic TyrRS gene. For example, a deletion/insertion allele can be constructed by excising the TyrRS open reading frame, promoter region and about 200 basepairs of the 3' flanking region from p13Gen, and replacing it with a TRP1 selectable marker. This tyrrs::TRP1 fragment can be used to transform the diploid strain FY83, and Trp+ transformants can be selected (Rothstein, J., Methods in Enzymol. 101:202–211 (1983)). Standard genetic procedures can be employed to identify the appropriate integrant created by this one-step gene disruption (a diploid having the genotype Mata/MATα lys2-128δ/lys2-128δ leu2Δ1/leu2Δ1 ura3-52/ura3-52 trp1Δ63/trp1Δ63 tyrrs::TRP1/TyrRS); Rose, M. D. et al. Methods in Yeast Genetics, 1990, Cold Spring Harbor Press, Cold Spring Harbor, N.Y.).

To construct a maintenance plasmid, a fragment from p13Gen containing the TyrRS coding region, its promoter and some of the 3' untranslated region (a region approximately equivalent to that deleted from p13Gen in the construction of the null allele above) can be excised and introduced into a vector such as YCplac33, a CEN plasmid containing a URA3 selectable marker (Gietz, R. D. and Sugino, A., *Gene* 74:527–534 (1988)). The resulting plasmid can be used to transform the tyrrs::TRP1/TyrRs diploid described above, and Ura+ transformants which contain the maintenance plasmid can be selected. The resulting diploid can be sporulated and a haploid Trp+Ura+ spore (a TyrRS null strain), corresponding to a tyrrs::TRP1 strain dependent upon the URA3-TyrRS maintenance plasmid can be isolated.

To construct a test plasmid (a plasmid bearing a heterologous tRNA synthetase gene to be tested for its ability to complement the defect in the endogenous yeast gene), a heterologous aaRS gene to be tested can be inserted into a suitable vector for expression. For instance, the multicopy vector pQB169 described in Example 15 can be used A fragment containing the *P. carinii* TyrRS gene can be inserted into pQB169, using one or more suitable restriction sites in the multiple cloning site, for example. Alternatively, to test whether a relatively reduced level of expression of the heterologous tRNA synthetase gene permits complementation, a fragment containing the *P. carinii* TyrRS gene can be inserted into a CEN plasmid such as pQB172 for expression (see Example 15). Preferably, the heterologous gene is inserted into the vector so that its ATG start codon is the first ATG within 50 to 100 bp of the transcription start site of the ADH promoter of the vector.

Because these plasmids bear the LEU2 selectable marker, they can be used to transform a null strain, such as the Trp+Ura+Leu– strain described, and Leu+ transformants containing the test plasmid can be selected. Leu+Ura+Trp+ transformants (containing a tyrrs::TRP1 allele, a URA3 maintenance plasmid, and the LEU2 test plasmid) can be tested for growth on media containing 5-fluoroorotic acid (5-FOA). 5-FOA is toxic to URA3 cells, and causes loss of the URA3 maintenance plasmid (Boake, J. et al., *Mol. Gen. Genet.*, 197:345–346 (1984)). Accordingly, growth of cells on media containing 5-FOA is indicative of complementation of the lethal deletion in the aaRS gene on the chromosome (tyrrs::TRP1) by the heterologous TyrRs gene on the test plasmid. Cells that are unable to grow on 5-FOA are dependent upon the maintenance plasmid for viability, and therefore, are indicative of insufficient activity to complement the lethal deletion in the aaRS gene. Where complementation is observed, the strain can be used to test for inhibitors of the product of the heterologous gene encoded by the test plasmid.

In another embodiment, a eucaryotic host cell is used to construct a mitochondrial tester strain. For example, in yeast, each of the mitochondrial tRNA synthetases is essential for growth on non-fermentable carbon sources (e.g., glycerol). Thus, complementation tests can be conducted in mitochondrial tester strains. As the genes encoding mitochondrial aminoacyl-tRNA synthetases are typically nuclear-encoded, the procedures described above can be modified to construct mitochondrial tester strains having a defect in a mitochondrial aminoacyl-tRNA synthetases. Modification is necessitated by the fact that yeast strains with a defect in mitochondrial protein synthesis, such as a defective aminoacyl-tRNA synthetase, lose their mitochondrial DNA, rapidly becoming rho–. As a result, these strains are unable to grow on non-fermentable carbon sources even if a complementing gene is introduced into the strain. Therefore, in a haploid strain having a defect in, for example, the yeast mitochondrial tyrosyl-tRNA synthetase gene (e.g., a gene disruption with a cosegregating selectable marker constructed as indicated above), the haploid strain can be crossed with a rho$^+$ strain having a wild-type mitochondrial tyrosyl-tRNA synthetase gene to restore the mitochondrial DNA. The resulting rho$^+$ diploid (see, for example, QBY243 in Example 18) can then be transformed with a plasmid which encodes the wild-type yeast mitochondrial tyrosyl-tRNA synthetase (i.e., a maintenance plasmid) and a second selectable marker. Following sporulation, progeny spores which carry the defective mitochondrial TyrRS, identified by the presence of the cosegregating selectable marker, and the maintenance plasmid, identified by the presence of the second selectable marker, and which are rho$^+$, can be isolated (e.g., by tetrad analysis). Strains constructed in this manner would be suitable for complementation assays using the pneumocystis aminoacyl-tRNA synthetases.

For instance, a plasmid encoding a pneumocystis tyrosyl-tRNA synthetase gene can be introduced into such a strain on a second plasmid having a third selectable marker. As indicated above, the maintenance plasmid can be selected against (e.g., where the selectable marker is URA3, selection on 5-fluoroorotic acid leads to loss of the maintenance plasmid), and complementation by the pneumocystis gene can be monitored on a non-fermentable carbon source.

In another embodiment, a mitochondrial aminoacyl-tRNA synthetase gene disruption with a cosegregating selectable marker can be constructed in a diploid rho$^+$ strain (see e.g., Edwards, H. and P. Schimmel, *Cell*, 51:643–649 (1987)). A plasmid encoding a pneumocystis aminoacyl-tRNA synthetase gene is introduced on a plasmid having a second selectable marker. Sporulation of a resulting diploid yields two progeny spores carrying the yeast mitochondrial aminoacyl-tRNA synthetase gene disruption, identified by the presence of a cosegregating selectable marker, and two progeny spores carrying the corresponding wild-type gene. The presence of the plasmid can be monitored by the presence of the second selectable marker. Complementation by the pneumocystis gene on the introduced plasmid is indicated by growth on non-fermentable carbon sources of spores carrying the disrupted aminoacyl-tRNA synthetase gene.

In the case of a mitochondrial tester strain, the pneumocystis aminoacyl-tRNA synthetase can be imported into mitochondria to achieve complementation of the mitochondrial defect. When it is necessary to achieve import or desirable to improve the efficiency of import of the aminoacyl-tRNA synthetase in the host cell, a gene fusion can be constructed using a sequence encoding a mitochondrial targeting sequence which functions in the host cell. For example, a mitochondrial targeting sequence can be introduced at the amino-terminal end of the pneumocystis aminoacyl-tRNA synthetase. In one embodiment in yeast, the pneumocystis aaRS gene or a sufficient portion thereof is introduced into a vector in which it is placed under the control of the minimal alcohol dehydrogenase promoter and is fused to the yeast cytochrome oxidase IV targeting signal derived from plasmid pMC4 (Bibus et al., *J. Biol. Chem.*, 263:13097 (1988)). Expression of the construct yields a fusion protein with an N-terminally located cytochrome oxidase IV targeting signal joined to the pneumocystis aaRS protein.

If the construction methods described here are not successful initially, one or more natural or synthetic pneumocystis or other (e.g., procaryotic, such as a bacterial, or eukaryotic, such as a mammalian or fungal) tRNA gene(s) can be introduced into the host cell to provide one or more cognate tRNAs for the pneumocystis aaRS. The tRNA genes of a number of species have been cloned and sequenced (Steinberg, S., et al. "Compilation of tRNA sequences and sequences of tRNA genes", *Nucleic Acids Res.* 21:3011–3015 (1993)). A method for constructing a strain of *Streptomyces lividans* in which an essential tRNA gene has been inactivated in the chromosome, and the gene is instead maintained on a plasmid, has been described (Cohen, S. N., WO 94/08033 (1994)).

Use of Tester Strains

To assess the inhibitory effect of a substance on a tester strain, the cells are maintained under conditions suitable for complementation of the host cell defect, under which complementation of the host cell defect is dependent upon the test gene (i.e., assay conditions). A substance to be tested is administered to the tester cells, and the viability or growth of the tester cells can be compared with that of cells of one or more suitable controls. A variety of control experiments can be designed to assess the inhibitory effect of a substance and/or the specificity of inhibition. The following examples are provided for purposes of illustration.

A preliminary test for inhibitory effect may be conducted where desired. For example, a substance to be tested can be administered to tester cells maintained under assay conditions, and the viability or growth of the tester cells in the presence of the substance can be compared with that of tester cells maintained under the same conditions in the absence of the substance. If it is determined that the substance inhibits growth of the tester cells, a further assessment of the specificity of inhibition by the substance can be conducted as described below.

Alternatively, the inhibitory effect of a substance on tester cell growth and the specificity of inhibition can be determined without conducting the preliminary test for inhibitory activity. The following examples, in which the various cell types are in each case exposed to drug, are provided for purposes of illustration only.

To determine the specificity of inhibition, the viability or growth of the tester cells can be compared with that of cells of one or more suitable control strains maintained under the same conditions. In particular, tester strains and control strains are maintained under assay conditions, and exposed to the substance to be tested.

Strains which are similar to the tester strain, but lack the heterologous aminoacyl-tRNA synthetase gene present in the tester strain (i.e., the "test gene"), can serve as control strains. These control strains comprise a "control gene" which is an aminoacyl-tRNA synthetase gene other than the heterologous aaRS gene present in the tester strain (i.e., an aaRS gene from a different species, such as a procaryotic or eukaryotic species). The control gene can be a cytoplasmic or mitochondrial aaRS gene, and it encodes an aaRS specific for the same amino acid as the aaRS encoded by the test gene. Viability or growth of the control strain is dependent upon the control gene under the conditions of the assay.

In one embodiment, a cell which is a cell of the same species as the host cell used to construct the tester strain, and which further comprises a control aaRS gene, is selected as a control. For example, the control gene can be a wild-type aaRS gene from the control strain species which encodes an aaRS specific for the same amino acid as the aaRS encoded by the test gene. Such a cell can be used when, for example, the substance or compound to be tested does not significantly affect growth of the control strain under the assay conditions. For example, where an *E. coli* host is used to construct a tester strain having a *P. carinii* aaRS gene, an *E. coli* strain having a wild-type *E. coli* control gene can be used as a control strain. As another example, if a yeast host cell having a defect in a mitochondrial aaRS gene is used to construct the tester strain, a yeast strain comprising the wild type mitochondrial gene can be used as a control strain.

In another embodiment, the control strain can be a strain distinct from the tester strain, which is constructed in a manner which generally parallels that of the tester strain comprising the test gene such that complementation of the host cell defect, which is also present in the control strain, is dependent upon the control gene under the assay conditions. In this embodiment, the control strain preferably comprises a host cell of the same species as the host cell used to construct the tester strain, and is closely related in genotype to the tester strain. These preferred control strains comprise a "control gene" which, as indicated above, is an aaRS gene other than the test gene (i.e., an aaRS gene from a different species, such as a heterologous procaryotic or eukaryotic species). Furthermore, the control gene, which can be cytoplasmic or mitochondrial, encodes an aaRS specific for the same amino acid as the test gene. Preferably, the control gene is selected from a species which is a host for the pathogen from which the test gene is derived, permitting the identification of specific inhibitors which selectively inhibit the pathogen aaRS (e.g., human control gene for *P. carinii* test gene). Alternatively, because the eukaryotic aminoacyl-tRNA synthetases are generally more closely related to each other than to procaryotic aminoacyl-tRNA synthetases, a control gene from another eukaryote (e.g., a different mammalian species) can be used in lieu of one selected from the host species (e.g., a rat or mouse control gene for a *P. carinii* test gene).

For example, a strain isogenic with a tester strain, except for the substitution of a human control gene, can serve as a control strain. Such a control strain can be constructed using the same methods and the same host cell used to construct the tester strain with the exception that a human control gene is introduced into the host cell in lieu of the heterologous pneumocystis aaRS gene present in the tester.

Under the conditions of this assay, growth or viability of the control strain is dependent upon the control aaRS gene, which complements the host cell aaRS defect in the control strain. Specific inhibition by a substance can be determined by comparing the viability or growth of the tester strain and control strain in the presence of the substance.

In some cases, further controls may be desired to assess specific inhibition. For this purpose, one or more additional "comparison control" strains are used for purposes of comparison. These additional controls can be used to assess the relative effects of a substance upon growth of the tester and control strains in the presence of the substance.

Strains useful for this purpose include, for example, strains of the same species as the host cell used to construct the tester strain, which contain a wild type version of the aaRS gene which is inactivated in the tester strain. In one embodiment, where an *E. coli* host is used to construct a tester strain comprising an *P. carinii* test gene, an *E. coli* strain comprising a wild-type *E. coli* aaRS gene can be used as a comparison control strain. In another embodiment, "parental-type" cells (e.g., parent host cells or a similar strain) are used as comparison controls. For example, the parent host cells of the tester strain can serve as a comparison control strain for the tester strain. Where the tester strain and the control strain have the same parent, a single strain can be used as the comparison control strain for both tester and control strains.

For example, a parent host cell from which the tester and control strains were both constructed (e.g., by inactivation and replacement of the wild type host aaRS gene) can be used as a comparison control strain. This comparison control strain contains a wild type version of the aaRS gene which is inactivated in the tester and control strains, and the viability or growth of this comparison control strain is dependent upon the wild type aaRS under the conditions of the assay. Specific inhibition of the heterologous pneumocystis aaRS encoded by the test gene (or a step in the expression of the pneumocystis gene) is indicated if, after administering the substance to the tester strain, growth of the tester strain is reduced as compared with an appropriate comparison control strain, and growth of the control strain is not reduced, or is relatively less reduced, as compared with its appropriate comparison control strain.

Testing for Antibiotic Resistance to tRNA Synthetase Inhibitors

Mutation of a drug target can reduce the effectiveness of antimicrobial or antibiotic agents, and can confer drug resistance. Thus, mutation of a target aminoacyl-tRNA synthetase, such as a *P. carinii* LysRS, TyrRS, IleRS, MetRS or AlaRS, could reduce the effectiveness of an inhibitor of aaRS activity. To test for mutations that confer resistance to an inhibitor (e.g., an inhibitor of aaRS activity, including such an inhibitor having antimicrobial activity) a variety of approaches can be used. Mutant pneumocystis aaRS genes can be obtained, for example, by isolation of a mutant gene, or by preparing an individual mutant gene or an expression library of mutant pneumocystis aaRS genes, such as a library of mutants of a pneumocystis aaRS gene. The mutant gone or gene library can be introduced into suitable host cells for screening for resistance to a compound.

An isolated tRNA synthetase gene, such as a *P. carinii* aaRS gene, can be mutagenized by any suitable method including, but not limited to, cassette mutagenesis, PCR mutagenesis (e.g., the fidelity of PCR replication can be reduced to induce mutation by varying $Mg^{2+}$ concentration, increasing the number of amplification cycles, altering temperatures for annealing and elongation, to yield random mutants), or chemical mutagenesis (e.g., nitosoguanidine, ethylmethane sulfonate (EMS), hydroxylamine) of the entire gene or a portion thereof. The mutagenesis products can be used to construct an expression library of mutant genes (e.g., by inserting the gene into an expression vector, or replacing a portion of an expression vector comprising the wild-type gene with mutant fragments) which is introduced into a host cell.

In one embodiment, if the inhibitor is known to inhibit the host cell (e.g., *E. coli,* yeast, *Bacillus subtilis*) aminoacyl-tRNA synthetase specific for the same amino acid, the mutant genes can be introduced into the wild-type host and the resulting cells can be exposed to drug to assess resistance.

In another embodiment, the procedures described above relating to tester strains are used in the method to identify mutants resistant to inhibitor. Introduction of the heterologous mutant aaRS gene(s) (i.e., mutant test gene(s)) into a host cell is carried out as described above for the production of tester strains. For example, the library can be introduced into a host cell having a defect in the endogenous gene encoding MetRS. The metG null strain of *E. coli* designated MN9261/pRMS615 is an example of the type of strain that can be constructed and used as a host for the introduction of mutant pneumocystis aaRS gene(s) (in that case, MetRS genes; see Kim et al., *Proc. Natl. Acad. Sci. U.S.A.* 90:10046–10050 (1993), a describing a strain which carries a null allele of metG, and a temperature sensitive maintenance plasmid, carring a wild type metG allele (encoding *E. coli* MetRS) and having a temperature sensitive replicon which causes loss of the maintenance plasmid at the non-permissive temperature).

Active, drug-resistant mutants are then identified by a selection process in which cells containing mutant genes encoding active aaRS are identified, and the effect of an inhibitor upon aaRS activity is assessed. Cells are maintained under conditions suitable for expression of the mutated gene, and cells containing an active mutant aaRS (e.g., an active recombinant *P. carinii* aaRS) are identified by complementation of the host cell defect. Where complementation occurs, each resulting transformant is, in essence, a tester strain comprising a mutant test gene. Cells containing active mutant aaRS as determined by complementation of the host cell defect are then exposed to inhibitor, and the effect of inhibitor on cell growth or viability is assessed to determine whether the active mutant aaRS further confers resistance to inhibitor.

In the case of the metG null strain, complementation by the pneumocystis gene is indicated by growth at the non-permissive temperature at which the maintenance plasmid is lost. Cells which survive loss of the maintenance plasmid due to the presence of the complementing mutant gene are then challenged with inhibitor to assess resistance. Resistance can be assessed by comparison to a suitable control by methods analogous to those described above for determining inhibition and/or the specificity of inhibition of a substance in tester cells. For example, the relative effects of an inhibitor upon a tester strain comprising the mutant test gene and upon a tester strain differing only in that it contains the test gene lacking the mutation, can be assessed by comparing the viability or growth of cells which are dependent upon either the test gene or mutant test gene for growth under conditions suitable for complementation of the host cell defect. For instance, the effect of inhibitor on the protein encoded by the test gene lacking the mutation can be determined by comparing the growth of cells containing the test gene in the presence of drug to the growth of such cells in the absence of drug, and the effect of inhibitor on the protein encoded by a mutant test gene can be determined by comparing growth of cells containing the mutant test gene in the presence of drug to the growth of such cells in the absence of drug. A decrease in the inhibitory effect on growth of cells carrying the mutant test gene as compared to the inhibitory effect against cells carrying the test gene lacking the mutation is indicative of resistance.

Cells containing a complementing mutant test gene which further confers resistance to an inhibitor can be used to identify derivatives of the inhibitor with improved antimicrobial effect, which circumvent resistance. Such cells can also be used to identify additional inhibitors having inhibitory activity against the active mutant aaRS encoded by the mutant test gene.

In another embodiment, a naturally occurring mutant pneumocystis aaRS gene which confers resistance to an inhibitor upon a pneumocystis cell, can be isolated from the pneumocystis organism using nucleic acids of the present invention as probes. The cloned gene can then be introduced into a host cell as described for the production of tester strains. Tester cells comprising the mutant test gene which confers resistance, and which complements the host defect, can be used as described herein to identify additional inhibitors having reduced susceptibility to the resistance mutation or derivatives of the inhibitor with improved inhibitory activity.

Vectors carrying mutant genes which confer resistance to inhibitor can be recovered and the insert analyzed to locate and identify the mutation by standard techniques, such as DNA sequence analysis, to yield additional information regarding the nature of mutations capable of conferring resistance to selected inhibitors. Mutant proteins can also be expressed and purified for further characterization by in vitro kinetic and binding assays.

Applications in Biochemistry

The pneumocystis aminoacyl-tRNA synthetase or stable subdomains of the protein can be used in a method to separate the amino acid that the enzyme specifically recognizes from a mixture of the amino acid and other compounds such as other amino acids, or to specifically isolate L-amino acid from D-amino acid. The tRNA synthetase can be chemically attached to a solid support material packed in a column or other suitable container. Alternatively, a fusion protein such as a GST-tRNA synthetase fusion or a His tail-tRNA synthetase fusion can permit attachment to a suitable solid support which binds the GST portion or His tail portion of the fusion protein, respectively. For example, a mixture of lysine and other compounds can be loaded onto a column under conditions in which lysine binds to lysyl-tRNA synthetase, while other compounds present in the mixture flow through the column. In a later step, lysine can be released from lysyl-tRNA synthetase by changing the conditions in the column, such as washing with a solution of high ionic strength to elute L-lysine, for example.

In a similar manner, the aminoacyl-tRNA synthetase can be used in a method to isolate tRNA that specifically recognizes the tRNA synthetase.

The pneumocystis aminoacyl-tRNA synthetase can be used in the quantitative determination of an amino acid such as lysine by its conversion to lysyl hydroxamate. An example of an appropriate assay is illustrated by the following series of reactions.

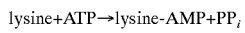

lysine+ATP→lysine-AMP+PP$_i$ (in the presence of excess pyrophosphatase and ATP at pH 7.5, where pyrophosphatase catalyzes the conversion of the product inorganic pyrophospate (PP$_i$) to inorganic orthophosphate (P$_i$); ATP is adenosine triphospate; AMP is adenosine monophosphate)

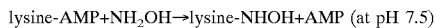

lysine-AMP+NH$_2$OH→lysine-NHOH+AMP (at pH 7.5)

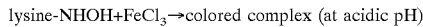

lysine-NHOH+FeCl$_3$→colored complex (at acidic pH)

The resulting colored complex can be quantitated by spectrophotometric measurements of absorbance at 540 nm, and compared with a standard curve made using known concentrations of lysine. This assay is based on the reactions described by Stulberg and Novelli, *Methods in Enzymology* 5:703–707 (1962).

The pneumocystis aminoacyl-tRNA synthetases can also be used for the quantitative determination of ATP. In the presence of excess amino acid such as lysine, and in the presence of pyrophosphatase to convert the product PP$_i$ to P$_i$, the ATP is quantitatively converted to AMP and inorganic pyrophosphate by the lysyl-tRNA synthetase. For example,

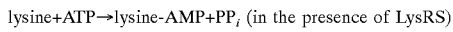

lysine+ATP→lysine-AMP+PP$_i$ (in the presence of LysRS)

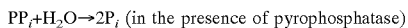

PP$_i$+H$_2$O→2P$_i$ (in the presence of pyrophosphatase)

P$_i$ can be quantitated by reaction with molybdate, measuring the absorbance at 580 nm and comparing to a standard curve made using known quantities of orthophosphate.

Characterization of the PCR Products of tRNA Synthetase Genes Generated from *P. carinii* Genomic DNA Polymerase chain reaction (PCR) fragments were made (Example 1) to use as probes to screen a rat derived *P. carinii* cDNA library for the tRNA synthetase genes. Degenerate oligonucleotide primers to make the PCR fragments were designed to hybridize to regions of tRNA synthetase genes which encode amino acids that are highly conserved among species. The degenerate oligonucleotides were used to prime the polymerase chain reaction on rat derived *P. carinii* genomic DNA under stringent conditions to obtain a PCR fragment of the tRNA synthetase gene.

1.) Characterization of the lysyl-tRNA synthetase PCR fragment

FIG. 1 (SEQ ID NO:34) shows the DNA sequence of the cloned lysyl-tRNA synthetase gene fragment. The fragment contains 177 basepairs (bp) of *P. carinii* DNA and is 63% A:T rich. A query was done to compare the DNA sequence of the lysyl-tRNA synthetase PCR fragment with the non-redundant protein database on the Experimental GENINFO (R) BLAST Network Service (Cruncher; available from the the National Center for Biotechnology Information (NCBI)). The result showed that the translated protein of the PCR fragment is homologous in amino acid sequence to the products of the *Escherichia coli* lysS (Kawakami, K. et al., *Mol. Gen. Genet.* 219:333–340 (1989)) and lysU genes (Leveque, F. et al. *Nucleic Acids Res.* 18:305–312 (1990); Clark, R. L. and Neidhardt, F. C., *J. Bacteriol.* 172:3237–3243 (1990)) and to the *Saccharomyces cerevisiae* (yeast) cytoplasmic lysyl-tRNA synthetase protein (Hirande, M. and Waller, J. P., *J. Biol. Chem.* 263:18443–18451 (1988)).

The results indicate that the cloned PCR product is a gene fragment from the lysyl-tRNA synthetase of *P. carinii*. The A:T richness of the fragment is consistent with the high A:T content of rat-derived *P. carinii* genes (U. Edman, et al., *Proc. Natl. Acad. Sci. U.S.A.* 86:6503 (1989); J. C. Edman, et al., *Proc. Natl. Acad. Sci. U.S.A.* 86:8625 (1989); L. D. Fletcher, et al., *Gene* 129:167–174 (1993)). The translated protein sequence aligns with the *E. coli* and yeast proteins in a statistically significant manner. This suggests that the DNA sequence reported is correct with no frame shift errors. A BLAST Network query of the DNA sequence with the non-redundant DNA database (Example 3) revealed that the cloned PCR fragment is not derived from the *E. coli* or yeast genome. In addition, a direct alignment of the *E. coli* and yeast tRNA synthetase DNA sequences with the PCR fragment sequence shows that the sequences are not significantly homologous.

2.) Characterization of the isoleucyl-tRNA synthetase fragment

The DNA sequence of the cloned PCR fragment is reported in FIGS. 2A–2B (SEQ ID NO:35). The fragment contains 480 bp of *P. carinii* DNA with two small introns of 44 and 42 basepairs. Each of the introns has the GT consensus sequence at its 5' exon-intron junction and the 3' splice-site consensus sequence TAG. The intron sequences are 70% and 86% A:T; the exon sequences are 63% A:T. The BLAST Network search indicates that the translated sequence is most homologous to the human cytoplasmic (Shiba, K. et al., *Proc. Natl. Acad. Sci. U.S.A.* 91:7435–7439 (1994)) and *Tetrahymena thermophila* (Csank, C., and Martindale, D. W. *J. Biol. Chem.* 267:4592–4599 (1992); GenBank Accession No. M30942) isoleucyl-tRNA synthetase proteins. The translated amino acid sequence of the fragment aligns well with the conserved regions of the human, *Tetrahymena thermophila* and yeast (Englisch, U. et al., *Biol. Chem. Hoppe-Seyler* 368:971–979 (1987); Martindale, D. W., et al., *Curr. Genet.* 15:99–106 (1989)) isoleucyl-tRNA synthetases. In a comparison of amino acid sequences, using the Clustal method with the PAM250 residue weight table (software is LaserGene for the Apple Macintosh by DNASTAR (Madison, Wis.), the partial sequence of the *P. carinii* isoleucyl-tRNA synthetase was most similar to the human isoleucyl-tRNA synthetase sequence (NCBI Seq ID: 440799; human isoleucyl-tRNA synthetase mRNA, and translated products; submitted by Nichols, R. C., 1994).

The data are consistent with this cloned PCR product being a *P. carinii* isoleucyl-tRNA synthetase gene fragment. The differential A:T richness of the intron (70% and 86%) and exon (63%) sequences are characteristic percentages for *P. carinii* genes (Edman, J. C. et al, *Proc. Natl. Acad. Sci. U.S.A.* 86:8625–8629 (1989)). In addition, the 42 and 44 bp intron sequences are the typical size for *P. carinii* introns (Fletcher, L. D. et al., *Gene* 129:167–174 (1993)). The locations of the intron sequences are between blocks of DNA that encode amino acids conserved among species.

3.) Characterization of the methionyl-tRNA synthetase fragment

The DNA sequence of the cloned PCR fragment is reported in FIGS. 3A–3B (SEQ ID NO:36). The PCR fragment contains 641 bp of *P. carinii* DNA with two introns of 45 and 57 basepairs. Each of the introns has the GT consensus sequence at its 5' exon-intron junction and the 3' splice-site consensus sequence AG. The intron sequences are 69% and 79% A:T; the exon sequences are 65% A:T. A BLAST Network search indicated that regions of the tranlated amino acid sequence of the fragment align well with the conserved regions of DNA sequences which have been determined for the methionyl-tRNA synthetases of *Thermus aquaticus* (subspecies *thermophilus;* Nureki, O., et al., *J. Biol. Chem.* 266:3268–3277 (1991); GenBank Accession No. M64273), *Bacillus stearothermophilus* (Mechulam, Y. et al., *Nucleic Acids Res.* 19:3673–3681 (1991); NCBI Seq ID No. 135148) and *Saccharomyces cerevisiae* mitochondria (Tzagoloff, A. et al., *Eur. J. Biochem.* 179:365–371 (1989); NCBI Seq ID No. 135147).

The data indicate that the PCR fragment encodes a portion of a *P. carinii* methionyl-tRNA synthetase protein. The sizes and base content of the introns in the PCR fragment are typical for *P. carinii* genes.

4.) Characterization of the tyrosyl-tRNA synthetase fragment

From the sequence analysis as in Example 3, the sequences from each strand of the PCR fragment showed homology to only the *S. cerevisiae* cytoplasmic tyrosyl-tRNA synthetase. The cloned DNA is 590 bp long and is 70% AT. Based on the alignment of open reading frames with the yeast gene (Chow and RajBhandary, *J. Biol. Chem.* 268: 12855–12863 (1993)) and consensus splice sites for *P. carinii* (Edlind et al., *Molec. Microbiol.* 6:3365–3373 (1992)), 3 introns were identified in the first 250 bp of the fragment. These 3 introns are very similar to other introns reported in *P. carinii* genomic DNA: they are 84%, 78%, and 75% AT; all 3 have a GTA 5' splice site; all 3 have an AG 3' splice site (FIG. 4; SEQ ID NO:37).

5.) Characterization of the alanyl-tRNA synthetase fragment

The DNA sequence of the cloned PCR fragment is shown in SEQ ID No:38. It is 329 basepairs long and 71% AT. The first 30 nucleotides are derived from the PCR primer Kiyo 23 (TTTGCGAATGCGGGGATGAACCAGTTCAAA; SEQ ID NO:7) and the last 30 nucleotides are derived from the PCR primer Kiyo 25 (GGTGCCCATCATCATTTCGAAGAAGGTGTGG; SEQ ID NO:8). Analysis of the sequence for this fragment (as in Example 3) shows that the open reading frames only have homology with alanyl-tRNA synthetase from *Bombyx mori* (Chang, P. K. and Dignam, J. D., *J. Biol. Chem.* 265:20890–20906 (1990)) and *Arabidopsis thaliana* (Mireau, H. et al., EMBL Z22673 (1993)). Alignment of the open reading frames and the presence of consensus splice sites led to the identification of intron sequences. There are 3 complete introns at nucleotides 103–143, 175–222 and 245–293. There are 2 partial exons covering nucleotides 1–102 and 294–329 and two complete exons covering nucleotides 147–174 and 223–244. At the exon-intron junctions there are consensus 5' GT and 3' AG splice sites. Removing the intron sequences gives an uninterrupted open reading frame of 64 codons which shows homology to the alanyl-tRNA synthetases from *E. coli* (Putney, S. D. et al., *Science* 213:1497–1502 (1981)) as well as *Bombyx mori* and *Arabadopsis thaliana.*

Isolation of the Coding Region (cDNAs) of the Lysyl- and Isoleucyl-tRNA Synthetase Genes from *P. carinii*

After screening the cDNA library as described in Example 4, 5 phage plaques that hybridized to the *P. carinii* isoleucyl-tRNA synthetase probe, and 3 that hybridized to the lysyl-tRNA synthetase probe were isolated and purified.

Phage from these plaques were converted to plasmid form (Example 5). DNA sequence analysis of the inserts in the plasmids confirmed that the isoleucyl- and lysyl-tRNA synthetases from *P. carinii* had been cloned. Clones lys #1 cDNA/SK+ and lys #2 cDNA/SK+ were identical to each other over the region that was sequenced. Each of these clones contained 7 intron sequences and therefore were not pursued further. The introns were defined by the fact that they: (1) interrupted the reading frame and the alignment of the protein sequence to sequences of other known tRNA synthetases, (2) were extremely A:T rich in DNA sequence and (3) contained consensus 5' and 3' splice-site junction sequences. Clone lys #5 cDNA/SK+ contained a full length copy of the coding region of the gene but also included two intron sequences (SEQ ID NO:39). As described in Example 6, these introns were removed to generate a full length, uninterrupted copy of the coding region of the gene (FIGS. 5A–5B; SEQ ID NO:40). Of the 5 positive phage that hybridized to the isolaucyl-tRNA synthetase gene fragment from PCR, one contained an insert too short to be a full length copy of the gene, and so it was not pursued. Two other phage contained inserts with introns and so they also were not pursued.

Clones ile #3 cDNA/SK+ and ile #5 cDNA/SK+s contained 3.0 kb of the coding region of the *P. carinii* isoleucyl-tRNA synthetase gene without any introns (SEQ ID NO:42). However, the 5' end of the gene encoding about 100 amino acids was missing from these clones based upon an analysis of the amino acid sequence homology to other cloned isoleucyl-tRNA synthetase genes.

Expression of Active Lysyl-tRNA Synthetase of *P. carinii*

The coding region of the lysyl-tRNA synthetase was subcloned into a fusion expression system (Example 7) and induced to express a fusion protein which combines *Schistosoma japonicum* glutathione S-transferase at the amino terminal end with *P. carinii* lysyl-tRNA synthetase at the C-terminal end (Example 7). The fusion protein was purified over a glutathione agarose column. The yield was about 1 mg of fusion protein per liter of culture (Example 9). A fraction of this protein was cleaved with thrombin to remove the GST portion of the hybrid (Example 11). Using a nitrocellulose filter binding assay, the proportion of the total protein that was active was determined (Example 12). A concentration of 11 μM of cleaved protein was used in the reaction as measured by comparison to standards on a Coomassie blue-stained polyacrylamide gel; the results from the assay indicated that 81% of the purified protein was active. The GST-lysyl-tRNA synthetase fusion protein and the cleaved version of the fusion protein synthetase were assayed for enzymatic activity in a tRNA charging assay using either purified *E. coli* lysine tRNA or crude brewers yeast tRNA (Example 13). Both the fusion and the cleaved protein charged both sources of tRNA as seen in FIG. 6.

Isolation of the Coding Region (cDNA) of the Tyrosyl Synthetase Gene from *P. carinii*

Six positive plaques were identified on the autoradiographs of both plaque lifts (Example 4). Plasmids containing the cDNA inserts were excised from three of these plaques (Example 5) according to the protocols of the EXAssist®/SOLR® system (Stratagene).

Phage from the purified plaques were converted to plasmid form. One such plasmid, pMTY4, was determined to contain the full-length cDNA for the *P. carinii* tryosyl-tRNA synthetase gene (Example 5).

The gene sequence (SEQ ID NO:44) includes 100 bases of untranslated DNA upstream from the ATG start codon. The translation of this sequence begins with the start codon at nucleotide 101 and ends with the termination codon at nucleotides 1211–1213. The open reading frame extends for 1.114 bp, ending with a TAA stop codon about 100 bases before the polyadenylation site, and encodes a protein of predicted molecular weight 41.000 Da. This gene is 69% AT and the codon usage reflects the bias for an A or T at the wobble nucleotide, consistent with the gene being from *P. carinii* (Fletcher et al., *Gene* 129:167–174 (1993)). The translated protein is 370 amino acids long. A protein data base search (using the non-redundant protein sequences in the Experimental GENINFO(R) BLAST Network Service) with this translated gene product reveal homology to the cytoplasmic tyrosyl-tRNA synthetase from *S. cerevisiae*. The *P. carinii* gene is 51% homologous to the yeast cytoplasmic tyrosyl-tRNA synthetase at the nucleotide level and 47% homologous at the amino acid level. As a class I synthetase, tyrosyl-tRNA synthetase is expected to have the HIGH and KMSKS concensus amino acid sequences that characterize the nucleotide binding domains of this class (Burbaum, J. J. and P. Schimmel, *J. of Biol. Chem.* 266:16965–16968 (1991)). The HIGH sequence in the *P. carinii* tyrosyl-tRNA synthetase is actually HCGY and the KMSKS sequence is actually KMSAS (similar to the cytoplasmic *S. cerevisiae* tyrosyl-tRNA synthetase).

Expression of Active Tyrosyl-tRNA Synthetase of *P. carinii*

The coding region for the tyrosyl-tRNA synthetase from *P. carinii* was cloned into an expression vector as described in Examples 8 and 10. The vector, expression and purification are as described for lysyl-tRNA synthetase expression. The yield of purified fusion protein was about 10 mg per liter of original culture. Samples of the protein were treated with thrombin to remove the GST portion as in Example 11. Protein concentrations of the cleaved and fusion proteins were measured by the Bradford method using the kit and protocols from Pierce. Activity of the proteins was measured as described in Example 14. Both cleaved and fusion proteins charged crude yeast tRNA with [$^3$H]-tyrosine (FIG. 7).

The present invention is more specifically illustrated in the following examples, which are not intended to be limiting in any way.

EXAMPLES

Example 1

Primer Design and Polymerase Chain Reaction

The amino acid sequences of four lysyl-tRNA synthetases were aligned to allow the design of primers (Kiyo-138 and Kiyo-140; SEQ ID NO:1 and SEQ ID NO:2, respectively; see Table 1) for amplification by polymerase chain reaction (PCR) of a fragment of the *P. carinii* lysyl-tRNA synthetase gene. These four sequences were from *Campylobacter jejuni* (Chan, V. L., and Bingham, H. L.,*J. Bacteriol.* 174:695–701 (1992)), *Saccharomyces cerevisiae* (Mirande, M. and Waller, J., *J. Biol. Chem.* 263:18443–18451 (1988)), and *Escherichia coli* lysS (Kawakami, K. et al., *Mol. Gen. Genet.* 229:333–340 (1989)) and lysU (Leveque, F. et al. *Nucleic Acids Res.* 18:305–312 (1990); Clark, R. L. and Neidhardt, F. C., *J. Bacteriol.* 172:3237–3243 (1990)).

The amino acid sequences of isoleucyl-tRNA synthetases from five different organisms were aligned to allow the design of primers (Kiyo-17 and Kiyo-36; SEQ ID NO:5 and SEQ ID NO:6, respectively; see Table 1) for amplification by PCR of a fragment of the *P. carinii* isoleucyl-tRNA synthetase gene. These five sequences were from *Methanobacterium thermoautotrophicum* (Jenal, U., et al., *J. Biol. Chem.* 266:10570–10577 (1991)), *S. cerevisiae* (ILS1; Englisch, U. et al., *Biol. Chem. Hoppe-Seyler* 368:971–979 (1987); Martindale, D. W., et al., *Curr. Genet.* 15:99–106 (1989)), *T. thermophilus* (S. Yokoyama), *Tetrahymena thermophila* (Csank, C., and Martindale, D. W., *J. Biol. Chem.* 267:4592–4599 (1992); GenBank Accession No. M30942), *Staphylococcus aureus* and *E. coli* (Webster, T. A., et al., *Science* 226:1315–1317 (1984)).

The amino acid sequences of five methionyl-tRNA synthetases from four different organisms were aligned and compared to allow the design of primers (Kiyo-12 and Kiyo-15; SEQ ID NO:9 and SEQ ID NO:10, respectively; see Table 1) for amplification by PCR of a fragment of the *P. carinii* methionyl-tRNA synthetase gene. These five sequences were from *Thermus aquaticus* (subspecies *thermophilus*; Nureki, O., et al., *J. Biol. Chem.* 266:3268–3277 (1991), GenBank Accession No. M64273), *Bacillus stearothermophilus* (Mechulam, Y. et al., *Nucleic Acids Res.* 19:3673–3681 (1991); NCBI Seq ID No. 135148) *Escherichia coli* (Dardel, F. et al., *J. Bacteriol.* 160:1115–1122 (1984)) and *Saccharomyces cerevisiae* (mitochondrial gene: Tzagoloff, A. et al., *Eur. J. Biochem.* 179:365–371 (1989); NCBI Seq ID No. 135147. cytoplasmic gene: Walter, P. et al, *Proc. Natl. Acad. Sci. U.S.A.* 80:2437–2441 (1983)).

involved in binding tyrosyl-adenylate (Monteilhet and Blow, *J. Mol. Biol.* 122:407–417 (1978)). The sequences of the primers were biased to reflect the codon bias of *P. carinii* (Fletcher, L. D. et al., *Gene* 129:167–174 (1993)).

The DNA sequences of the primers used to obtain a PCR fragment of each of the tRNA synthetase genes, along with the regions of amino acid sequence upon which they are based, are given in Table 1.

TABLE 1

| Enzyme | Amino Acid Sequence | Primer Name | SEQ ID NO: | Oligonucleotide Sequence | Priming Direction |
|---|---|---|---|---|---|
| LysRS | (Fv)(LMI)EVETP(Mc)M | Kiyo-138 | 1 | TTY MTI GAR GTI GAR ACI CCI ATG ATG | → |
|  | HNPEFT(MT)IMLc)E(FLW)Y | Kiyo-140 | 2 | TAC MAY TCI AKC ATI GTR AAY TCI GGR TTR TG | ← |
| TyrRS | KLYWGTAPTG | TyrF100 | 3 | AAA YTW TAT TGG GGW ACW GCW CCW ACW GG | → |
|  | DCQFGGVDQ | TyrR281 | 4 | TTG ATC WAC WCC WCC AAA TTG ACA ATC | ← |
| IleRS | GWDCHG(Lv)P | Kiyo-17 | 5 | GCG AAT TCG GIT GGG AYT GYC AYG GIC TIC C | → |
|  | WTTTPWTLP | Kiyo-36 | 6 | GGI ARI GTC CAI GGI GTI GTI GTC CA | ← |
| AlaRS | F(TA)NAGM(Nv)QFK | Kiyo-23 | 7 | TTY RCI AAY GCI GGI ATG AAY CAR TTY AAA | → |
|  | H(H1)TFFEM(M1)GN | Kiyo-25 | 8 | RTT ICC CAT CAT YTC RAA RAA IGT RTG RTG | ← |
| MetRS | (Fy)(Lt)TGTDEHG | Kiyo-12 | 9 | GCG AAT TCT WYC TIA CIG GIA CIG AYG ARC AYG G | → |
|  | YVW(LF)DA(Pt)IGY | Kiyo-15 | 10 | GCG AAT TCR TAI CCR ATI GKI GCR TCI ARC CAI ACR TA | ← |

Two complete coding sequences and two partial sequences of the N-terminal coding regions of alanyl-tRNA synthetases were aligned and studied for conserved regions of amino acid sequence to use as the basis for primer sequences (Kiyo-23 and Kiyo-25; SEQ ID NO:7 and SEQ ID No:8, respectively; see Table 1). The two complete sequences were from *E. coli* (Herlihy, W. C. et al., *Proc. Natl. Acad. Sci. U.S.A.* 77:6531–6535 (1980) and from *Bombyx mori* (Chang, P. K., and Dignam, J. D., *J. Biol. Chem.* 265:20898–20906 (1990)). The partial sequences were from *Rhizobium meliloti* and *R. leguminosarum* biovar *viciae* (Selbitschka, W. A. et al., *Mol. Gen. Genet.* 229:86–95 (1991)).

To design primers to amplify a fragment of DNA within the tyrosyl-tRNA synthetase gene sequences of tyrosyl-tRNA synthetase coding regions from the following organisms were aligned and studied to identify regions of conserved amino acid sequence: *Neurospora crassa* (mitochondrial; Collins and Lambowitz, *J. Mol. Biol.* 184:413–428 (1985)), *Bacillus stearothermophilus,* (Winter et al., *Eur. J. Biochem.* 158:699–709 (1983)), *E. coli* (Barker et al., *J. Bacteriol.* 174:6033–6045 (1992)), *Podospora anserina* (Kaemper et al., *Mol. Cell. Biol.* 12:499–511 (1992)), *Thiobacillus ferrooxidans* (Salazar et al., *J. Bacteriol.* 176:4409–4415 (1994)) *Bacillus subtilis* (Glaser et a., *DNA Seq.* 1:251–261 (1991)), *Bacillus caldotenax* (Jones et al., *Biochemistry* 25:1887–1891 (1986)), and *S. cerevisiae* (cytoplasmic; Chow and RajBhandary, *J. Biol. Chem.* 268:12855–12863 (1993)). Unlike the primers above, the primers to amplify a fragment of the *P. carinii* tyrosyl-tRNA synthetase (TyrF100 and TyrR281; SEQ ID NO:3 and SEQ ID NO:4, respectively; see Table 1) were chosen based not on a concensus amino acid sequence from the known sequences, but on only the amino acid sequence of the *S. cerevisiae* enzyme within two conserved regions. These regions have been identified in the crystal structure of the tyrosyl-tRNA synthetase of *B. stearothermophilus* as being To obtain a fragment of the *P. carinii* tyrosyl-tRNA synthetase gene, a PCR reaction was performed as follows. Forty ng of rat derived *P. carinii* genomic DNA (from Christine Dykstra, University of North Carolina, Chapel Hill; See Fletcher, L. D., et al. *Gene* 129:167–174 (1993)), 2 μM of each primer 100 μM of each of the 4 dNTP's, 1.25 Taq DNA polymerase (Boehringer-Mannheim Biochemicals), 60 mM Tris pH 8.5, 2 mM $MgCl_2$, and 15 mM $NH_4SO_4$ in a total of 50 μl were cycled 40 times at 94° C. for 30 seconds, at 45° C. for 60 seconds, and at 72° C. for 60 seconds. This reaction yielded a DNA fragment that ran as an approximately 600 basepair (bp) fragment on a 1.5% agarose gel in 1×TBE buffer. (TBE buffer is 90 mM Tris, 60 mM boric acid, 2.5 mM ethylenediamine tetraacetic acid (EDTA) at pH 8.0.)

The remaining PCR reactions (to obtain fragments of the alanyl-, methionyl-, lysyl-, and isoleucyl-tRNA synthetase genes of *P. carinii*) were carried out under somewhat different conditions; these reactions were done in 60 mM Tris-HCl pH 8.5, 2 mM $MgCl_2$, 15 mM $(NH_4)SO_4$, 50 μM each dNTP, 100 pM of each primer used, 15 ng *P. carinii* genomic DNA, 1.25 Units of Tag DNA polymerase (Boehringer-Mannheim), 0.5 μM T4 gene 32 protein in a 50 μl volume. Control reactions were run without either primers or template DNA. Reactions were denatured at 94° C. for 30 seconds before adding Taq polymerase. Reactions were cycled 29 times at 94° C. for 30 seconds, 55° C. for 30 seconds, and 72° C. for 1.5 minutes. In the last cycle, the extension time was 10 minutes at 72° C. One fifth of the reaction was checked on a 2% agarose gel to determine that there was a single PCR product. Occasionally, the reaction was cycled for not greater than five more cycles to obtain more PCR product. The entire reaction was precipitated and purified by electrophoresis on a 2% agarose gel. The PCR product was cut out of the gel and purified using the GeneClean kit (Bio101).

Example 2

Cloning and Sequencing

The PCR fragment of the tyrosyl-tRNA synthetase gene was purified by agarose gel electrophoresis followed by extraction from the gel using the Geneclean II kit (Bio101). The fragment was then ligated into the pT7Blue T-Vector using the kit from Novagen, taking advantage of the 3' dT nucleotide overhangs in the vector as supplied and the 3' dA overhangs left by Taq DNA polymerase (Clark, *Nucleic Acids Res.* 16:9677 (1988)). The resulting recombinant plasmid, pQY11, was sequenced on both strands using the T7 promoter primer (taatacgactcactataggg; Novagen cat. #69348-1) (SEQ ID NO:11) and the U-19mer primer (gttttcccagtcacgacgt; Novagen cat. π69819-1) (SEQ ID NO:12), as well as primers designed to be complementary to the inserted DNA sequence.

One-half of the total yield of PCR fragment obtained for the alanyl-, lysyl-, isoleucyl- and methionyl-tRNA synthetase genes was ligated into 50 ng of the pT7Blue T-Vector (Novagen) which is supplied in linear form with single 5' dT-nucleotide overhangs. NovaBlue competent cells (Novagen) were transformed with the ligation reaction and plated on LB medium containing 100 µg/ml ampicillin and 15 µg/ml tetracycline. 35 µl of 50 mg/ml 5-bromo-4-chloro-3-indolyl-β-D-galactopyranoside (X-gal) and 20 µl 130 mM isopropyl-1-thio-β-D-galactoside (IPTG) were spread on the plates in order to screen for blue or white colonies (as described by Novagen). Potential recombinants were rapidly screened by direct colony PCR using primers that hybridize to the vector sequences flanking the cloning site, T7 promoter primer and U-19mer primer. The recombinant plasmids were purified using a Qiagen column and the DNA sequences of the inserts in the plasmids were determined by dideoxy-sequencing (Amersham kit). Plasmid 5-1/pT7 encoded part of the alanyl-tRNA synthetase gene, plasmid 3-25/pT7 encoded part of the lysyl-tRNA synthetase gene, plasmid 1-6/pT7 encoded part of the isoleucyl-tRNA synthetase gene and plasmid 4-3/pT7 encoded part of the methionyl-tRNA synthetase gene.

Example 3

Data Analysis of Cloned PCR Products

The DNA sequences of all the cloned PCR fragments were queried against the Non-redundant Protein (Non-redundant PDB+SwissProt+SPupdate+PIR+GenPept+GPupdate, 1994) and Nucleic Acid Data Bases using the Experimental GENINFO(R) BLAST Network Service (Cruncher) at the National Center for Biotechnology Information (NCBI). (See, for BLAST algorithm (Basic Local Alignment Search Tool), Altschul, S. F., et al., *J. Mol. Biol.*, 215:403–410 (1990); Gish, W., and D. J. States, *Nature Genetics*, 3:266–272 (1990)). The MegAlign program in the DNASTAR (Hadison, Wis.) software package was used to do alignments of amino acid homologies between the translated sequences of the PCR fragments and tRNA synthetases from other species.

Example 4 cDNA Library Screening

The rat-derived *P. carinii* cDNA library was obtained from the NIH AIDS Research and Reference Reagent Program. The library was constructed in the unidirectional Uni-Zap® XR lambda phage vector (Stratagene) and contained sequences ranging in size from 0.2 to 5.0 kilobasepairs in 90% of the phage particles.

The cloned fragment of the tyrosyl-tRNA synthetase gene was amplified by PCR using the T7 promoter primer and the U-19mer primers described in Example 2. The PCR reactions were in 50 µl volumes with 50 ng of each primer; about 100 ng of PQY11 plasmid; 100 µM each of ATP, dCTP, dGTP and dCTP; 1.25 Taq DNA polymerase (Boehringer-Mannheim Biochemicals); 60 mM Tris pH 8.5; 2 mM $MgCl_2$; and 15 mM $NH_4SO_4$. The reaction was cycled 35 times at 94° C. for 30 sec, 50° C. for 60 sec, and 72° C. for 60 sec.

The gel purified (Geneclean II Kit, Bio101) PCR fragment of the tyrosyl-tRNA synthetase gene (approximately 600 bp in size) was labeled with $^{32}P$ using the DecaPrime random labeling kit, which uses random decamer primers to initiate synthesis of a complementary strand (Ambion) and used to probe the *P. carinii* cDNA library obtained from the NIH AIDS Reagent Program. The library, cloned into the λzap expression vector, Uni-Zap XR (Stratagene) was plated out on *E. coli* XL1Blue cells with about 30,000 plaques on a large (9×9 inch) plate. Duplicate Hybond N (DuPont NEN) lifts of the plate were probed with about $10^6$ cpm of labeled probe/ml in hybridization buffer (5×SSC, 0.1% SDS, 50% formamide, 0.1 mg/ml sheared salmon sperm DNA and 1×Denhardt's solution; 1×SSC is 0.15M NaCl/0.015M $Na_3$-citrate pH 730; 1×Denhardt's solution is 0.2% polyvinylpyrrolidone, 0.02% Ficoll and 0.2% bovine serum albumin) at 42° C. overnight. The hybridized blots were washed once in 2×SSC/0.1% SDS at room temperature, and a second time for one hour. Six plaques that hybridized to the labeled PCR fragment of the tyrosyl-tRNA synthetase gene were subjected to 3 rounds of plaque purification with rehybridization to the probe. Three pure plaques were isolated that hybridized to this probe.

The recombinant plasmids containing the *P. carinii* isoleucyl-tRNA and lysyl-tRNA synthetase gene fragments generated by PCR were digested with NdeI and BamHI, releasing the cloned PCR product (plus a few basepairs at either end originating in the T7-Blue T-Vector cloning region) from the vector. The resulting fragments were separated by electrophoresis on a 2% agarose gal and purified by using GeneClean (Bio101) on the excised gel band. About 200 ng of the fragment was internally labeled with $[\alpha\text{-}^{32}P]$ dATP using the random primer labeling method (Invitrogen).

One hundred and fifty thousand plagues were screened using the labeled isoleucyl-tRNA synthetase fragment as isolated from the plasmid and 200,000 plaques were screened using the lysyl-tRNA synthetase fragment. Plaques were lifted onto large Gene Screen Plus filters (DuPont NEN, Boston) from plates containing 50,000 plaques. Two filters per plate were made to control for false positive signals. The phage were denatured on the filters by saturating the filters with 1.5M NaCl, 0.5M NaOH for 1 to 2 minutes. The filters were neutralized by saturating the filters with 1.5M NaCl, 0.5M Tris-HCl pH 74 for 1 to 2 minutes. The filters were then washed with 2×SSC at room temperature and baked under vacuum at 80° C. for 1 hour. Filters were pre-hybridized for 2–3 hours at 42° C. In a 50 ml volume of 5×SSC, 1×Denhardt's solution, 0.1% SDS, 50% formamide, 0.1 mg/ml denatured, sheared, salmon sperm DNA. After boiling, $1\times10^7$ counts per minute (cpm) of the $^{32}P$-labeled fragment were added to 50 ml of the pre-hybridization solution. The duplicate filters were hybridized with the $^{32}P$-labeled fragment overnight at 40° C. The filters were washed twice in 2×SSC, 1.0% SDS at room temperature for 20 minutes, and then washed in 0.5×SSC, 1.0% SDS at 65° C. for 1 hour.

After washing, the dried blots were wrapped in plastic and exposed to Kodak X-OMAT film with amplifying screens at −80° C. overnight.

Example 5

Excision of Phagemid from the Lambda Phage

To obtain plasmid forms of the lambda cDNA clones, the phagemid was excised from the Uni-Zap® XR lambda phage vector as described by the vendor ("ExAssist®/SOLR® System Instruction Manual" Catalog #200253; Stratagene; Jun. 24, 1993). An agarose plug of a purified plaque was resuspended in 500 μl SM buffer (0.1M NaCl, 0.02M MgSO$_4$, 0.05M Tris-HCl (pH 7.5), and 0.01% gelatin) with 20 μl chloroform for 1 hour at room temperature 100 μl of this phage suspension was incubated with 200 μl of bacterial strain XL1Blue (Stratagene) at OD$_{600}$ 1.0 and 1 μl Ex-Assist helper phage (>1×10$^3$ plaque-forming units) for 15 minutes at 37° C. Three ml of 2×YT medium was added and the infected cells were incubated with shaking for 3–5 hours at 37° C. This was heated to 70° C. for 20 minutes, then spun down to pellet the bacterial cells. In two different tubes, 1 or 50 μl of the supernatant was incubated for 15 minutes at 37° C. with 200 μl of the bacterial SOLR strain (Stratagene) grown to an OD$_{600}$ of 1.0. 100 μl from each tube of the cells infected with the phagemid was plated on LB agar with 100 μg/ml ampicillin and incubated overnight at 37° C. Phagemid DNA was isolated from these colonies by growing cell cultures overnight in LB plus 100 μg/ml and using Wizard plasmid isolation kits (Pharmacia, Uppsala).

One isolate, pNTY4, derived from a plaque that hybridized to the labeled PCR fragment of the tyrosyl synthetase gene, contained a 1.35 kb (kilobasepair) EcoRI to XhoI insert encoding the full length cDNA for the *P. carinii* tyrosyl-tRNA synthetase gene. This insert was sequenced on both strands using the Sequenase sequencing kit from U.S. Biochemicals. The sequence is shown in FIG. 4 (SEQ ID NO:37).

The other DNA sequences of the inserts in the phagemids were determined by dideoxy sequencing (Amersham Kit). Plasmid lys 5' #1 cDNA/SK+ contained a full length clone of the *P. carinii* lysyl-tRNA synthetase but there were two intron sequences present in the clone that interrupted the coding region of the protein.

Example 6

Excision of the Introns from the Coding Region of the *P. carinii* Lysyl-tRNA Synthetase Gene Two intron sequences present in the full length cDNA clone had to be removed from the DNA to obtain the full length coding region to express the protein. The introns were removed by generating PCR products that lacked the intron sequences using the lys 5' #1 cDNA/SK+ plasmid as a template and replacing the sequences containing the introns in this plasmid with these PCR products.

The sequences of the primers used for this plasmid construction to prime PCR using the lys 5' #1 cDNA/SK+ as template are as follows.

Primer 23a (SEQ ID NO:13) consists of nucleotides 62–78 of the coding strand of the LysRS gene, with an extra 12 nucleotide sequence at the 5' end to provide a BamHI site.
23a: GGA,TCC,GGA,TCC,ATG,GAG,GAA,TCT,TCA,CC Primer 24a (SEQ ID NO:14) consists of nucleotides 277–246 of the non-coding strand of the LysRS gene, with an extra 10 bases at the 5' end.

24a: GCT,CAT,AAT,AAA,CAT,TAG,GCG,TTA,AAT,CTT,CAT,TAA,TTT,CTG

Primer 25a consists of nucleotides 624 through 590 of the non-coding strand of the LysRS gene (SEQ ID NO:40), and contains a naturally-occurring NsiI site at nucleotides 622–615.
25a: GCT,CAT,GCA,TTT,CTA,AGT,AGT,CTT,TTT,CAC,AAT,CC Primer 26a (SEQ ID NO:15) consists of nucleotides 330–363 of the coding strand of the LysRS gene, plus an additional 7 nucleotides at the 5' end.
26a: CT,AAT,GTT,ATT,ATG,AGC,TTC,GTT,CTC,GGC,ATA,TTA,ATA,TGC Primer 27 consists of nucleotides 1551–1579 of the coding strand of the LysRS gene (SEQ ID NO:40), and contains a naturally-occurring BglII site at nucleotides 1554–1559.
27: CAT,AGA,TCT,AAT,GTA,GGA,TTA,TGT,GAA,AG Primer 28 (SEQ ID NO:16) consists of nucleotides 1735–1704 of the non-coding strand of the LysRS gene, and has an additional 9 nucleotides at the 5' end.
28: CCA,TAA,TCC,AAA,GCT,AAA,CAA,AAA,TTC,TCA,TCA,ATA,ATT,TG Primer 29 consists of nucleotides 2123–2089 of the non-coding strand of the LysRS gene (SEQ ID NO:40), and contains a naturally-occurring XhoI site at nucleotides 2124–2129.
29: CCT,CGA,GTT,TTT,TTT,TTT,TTT,TTT,TAA,ATA,CAT,AC Primer 31 (SEQ ID NO:17) consists of nucleotides 1781–1810 of the coding strand of the LysRS gene, and contains an additional 10 nucleotides at the 5' end.
30: GTT,TAG,CTT,TGG,ATT,ATG,GAT,TAC,CGC,CTA CTG,CAG,GAT,G The polymerase chain reactions were done in a 50 μl total volume containing: 10 ng template lys 5' #1 cDNA/SK+ DNA or 50 ng of each of PCR products A and B (or products C and D), 50 ng of either primer 23a, 25a, 27 or 29, 100 ng of primer 24a, 26a, 28, or 30, 2 μl of a stock solution of 2.5 mM dNTPs, 200 units of Vent DNA polymerase (New England Biolabs), 10 mM KCl, 10 mM (NH$_4$)$_2$SO$_4$, 20 mM Tris-HCl (pH 8.8 at 25° C.), 2 mM MgSO$_4$, 0.1% Triton X-100. The cycle conditions were (1) 99° C., 2 minutes; (2) 99° C., 1 minute; (3) 55° C., 30 seconds; (4) 75° C., 1 minute; (5) repeat steps 2–4, 29 more times; (6) 75° C., 3 minutes. PCR products were purified by electrophoresis through an agarose gel, followed by extraction from the gel using GeneClean (Bio101).

To remove intron 1, two PCR products were generated. Primers 23a and 24a were used to make PCR product A. Primers 25a and 26a were used to make PCR product B. Products A and B were annealed and used as a template for another round of PCR using 23a and 25a as primers. This generated a PCR fragment with BamHI and NsiI ends which contained part of the lysyl-tRNA synthetase coding region and lacked intron 1.

To remove intron 2, two PCR products were generated. Primers 27 and 28 were used to make PCR product C. Primers 29 and 30 were used to make PCR product D. Products C and D were annealed and used as a template for another round of PCR using 27 and 29 as primers. This generated a PCR fragment with BglII and XhoI ends which contained part of the lysyl-tRNA synthetase coding region and lacked intron 2. The BamHI-NsiI and BglII-XhoI PCR fragments were each cloned into the pT7Blue T-Vector (Novagen). DNA sequence analysis confirmed that their sequence was as expected. The lys 5' #1 cDNA/SK+ plasmid was cut with BamHI and NsiI and the BamHI-NsiI fragment containing the intron was replaced with the BamHI-NsiI fragment from pT7Blue T-Vector which contained the lysyl-tRNA synthetase coding region without intron 1. This plasmid (Lys1 a+b(−)intron 1/SK+ #6) was then cut with BglII and XhoI and the BglII-XhoI fragment containing the intron was replaced with the BglII-XhoII fragment from pT7Blue which contained the lysyl-tRNA synthetase coding region without intron 2. This final construct yielded a plasmid named Lys(−)introns 1,2,SK+ #16. As determined by dideoxy sequencing (Amersham kit), this plasmid contained the entire coding region of the *P. carinii* lysyl-tRNA synthetase gene with no intron sequences.

Biolabs) which anneals downstream from the XhoI cloning site in the cDNA cloning vector in the PCR amplification of *P. carinii* tyrosyl-tRNA synthetase using pNTY4 as template. The resulting PCR fragment was digested with BamHI and XhoI restricition enzymes. The digested PCR fragment was gel purified and cloned into pGEX-4T-1 digested with the same two restriction enzymes. This plasmid pGEXYG18, was sequenced to verify the insertion of the gene at the expected cloning sites and the integrity of Taq polymerase in incorporating the correct nucleotides in the PCR amplification. Engineering this expression vector leads to a protein fusion junction with the structure as shown below (DNA sequence is SEQ ID NO:20; amino acid sequence is SEQ ID NO:21), in which the line over the amino acid sequence shows the thrombin recognition site, and the bold letters designate the sequence of *P. carinii* tyrosyl-tRNA protein and gene. Cleavage should occur between the R and G amino acid residues.

| ... L | V | P | R | G | S | M | G | F | T | S | E | I ... |
|---|---|---|---|---|---|---|---|---|---|---|---|---|
| ... ctg | gtt | ccg | cgt | gga | tcc | atg | gga | ttt | aca | agt | gaa | ata ... |

Example 7

Construction of a Plasmid for Expression of a *P. carinii* Lysyl-tRNA Synthetase Fusion Protein A BamHI-XhoI fragment containing the entire coding region of the *P. carinii* lysyl-tRNA synthatase protein was excised from plasmid Lys(−)introns 1,2SK+ #16 and ligated into the BamHI-XhoI site of plasmid pGEX-4T-2 (Pharmacia) to generate a new plasmid named lys/pGEX.4T.2 #2. This plasmid contains an in-frame fusion of the coding regions of glutathione S-transferase (GST) with the *P. carinii* lysyl-tRNA synthetase gene such that a fusion protein can be produced. (See procedures manual from Pharmacia P-L Biochemicals, Inc.: *GST Gene Fusion System* (1993) regarding use of pGEX expression vectors and glutathione S-transferase fusion proteins.) This construct was sequenced by dideoxy sequencing (Amersham Kit).

Example 8

Construction of a Plasmid For Expression of *P. carinii* Tyrosyl-tRNA Synthetase A primer was designed to allow PCR amplification of the *P. carinii* tyrosyl-tRNA synthetase gene in pNTY4, without untranslated DNA sequences, for cloning as an in-frame gene fusion to the glutathione S-transferase gene (GST) in the pGEX-4T-1 expression vector (Pharmacia) or a yeast expression vector. This primer, PcY5GST has the following sequence (SEQ ID NO:18):

cgc gga tcc *atg gga ttt aca agt gaa ata* g where the italicized nucleotides reflect the inclusion of a BamHI restriction site and the underlined nucleotides reflect the codons for the N-terminal amino acids of the *P. carinii* tyrosyl-tRNA synthetase open reading frame. The primer was paired with the commercially available universal primer (gtaaaacgacggccagt (SEQ ID NO:19); New England

Example 9

Expression and Purification of a GST-Lysyl-tRNA Synthetase Fusion Protein

To express the GST-lysyl-tRNA synthetase fusion protein, 25 ml of an overnight culture of DH5α containing the lys/pGEX.4T.2 #2 plasmid was grown in 1 liter of LB plus 100 μg/ml media at 37° C. until the culture reached an $OD_{600}$ of between 0.6 and 1.0. It was then induced by addition of IPTG to a final concentration of 1 mM and grown at 18° C. for 2.5 days with aeration. (An alternative procedure in which the cells were induced with IPTG in the same manner and grown overnight at 37° C. did not lead to overproduction of the fusion protein, as judged by analysis of a crude protein extract on an SDS-polyacrylamide gel.) The cells were pelleted and resuspended in 30 ml cold 1×PBS (phospate buffered saline). The cell suspension was lysed using a French press, keeping all reagents cold. The suspension was centrifuged at 14,000 rpm for 40 minutes at 4° C. In a cold room, the supernatant was passed over a 10 ml bed volume glutathione agarose column (Sigma, Cat.# G4510) pre-equilibrated with 1×PBS. The column was washed three times with 100 ml of 1×PBS. The sample was eluted by applying 5 ml of 10 mM reduced glutathione in 50 mM Tris-HCl pH 8.0 to the column at room temperature and collecting the volume for 30 minutes. This step was repeated two more times. The 15 ml elution volume was concentrated to 1 ml using a Centricon-100 filter (Amicon) centrifuged at 3,000 rpm at 4° C. The sample was diluted 1:10 in 30 mM $KPO_4$ (1 ml in 10 ml) and concentrated to a volume of 1 ml using a Centricon-100 filter. This 1 ml volume was concentrated to approximately 100 μl using a Centricon-30 filter centrifuged at 3,000 rpm at 4° C. The protein was stored at 4° C. or −20° C. in 40% glycerol.

Example 10

Expression and Purification of a GST-Tyrosyl-tRNA Synthetase Fusion Protein pGEXYG18 was used to express the *P. carinii* tyrosyl-tRNA synthetase with an N-terminal fusion to glutathione S-transferase (GST). Because most of the expressed protein appears to form insoluble inclusion bodies when the cells are grown at 37° C., an alternative procedure was used for the induction and growth of the cells. Cells were grown to mid-log phase in LB plus 100 µg/ml ampicillin at 37° C. before inducing by adding 0.1 mM IPTG and allowing continued growth for 3 days at 18° C. with shaking. As seen on a 12% polyacrylamide SDS gel stained with Coomassie blue, the fusion protein is found in both the soluble (supernatant) and insoluble (pellet) fractions of the lysed cells, and has a molecular weight of 67,000. Fusion protein from the soluble fraction was purified on a glutathione-agarose affinity column following the protocols described by Pharmacia (Procedures 7 and 11 in Pharmacia Manual, *GST Gene Fusion System;* Pharmacia P-L Biochemicals, Inc.; 1993), and a sample of the purified fusion protein was run on the gel to confirm the identity of the bands appearing in the lanes loaded with crude cell extract. Lysed cell supernatant was purified on a glutathione agarose column and digested with thrombin as in Example 11. A sample of this purified, digested GST-tyrosyl-tRNA synthetase showed two protein bands on PAGE-SDS. A band at about 26 kDa is the glutathione S-transferase; the other band at about 40 kDa is the tyrosyl-tRNA synthetase.

EXAMPLE 11

Cleavage of the GST-Lysyl-tRNA Synthetase Fusion Protein and the GST-Tyrosyl-tRNA Synthetase Fusion Protein To cleave off the GST portion of the GST-lysine tRNA synthetase fusion protein (see Procedure 12 in Pharmacia Manual, *GST Gene Fusion System;* Pharmacia P-L Biochemicals, Inc.; 1993), 250 µg fusion protein was cleaved in a 50 µl volume with 3.15 units thrombin (Novagen, cat.#69672-1) in 50 mM sodium citrate, pH 6.5, 200 mM NaCl and 0.1% polyethylene glycol (average molecular weight 8000) at room temperature for 4–5 hours or at 4° C. for 16 hours. The GST portion removed by passing the cleavage reaction over a glutathione agarose column with a 1 ml bed volume. The sample was brought up to a 1 ml volume of PBS and applied to the column. The flow-through was collected. An additional 1 ml of 1× PBS was applied to the column and collected and pooled with the flow-through from the sample application. This 2 ml volume was concentrated to-100 µl using a Centricon-30 filter as described in Example 11. The cleaved protein was stored in 40% glycerol at –20° C.

The GST portion of the GST-tyrosyl-tRNA synthetase protein was cleaved off, thereby producing cleaved tyrosyl-tRNA synthetase, by digestion with thrombin (10 units thrombin/mg protein, 16° C. for 20 hours plus a room temperature incubation for 2–3 hours).

EXAMPLE 12

Active Site Titration Assay of the GST=Lysyl-tRNA Synthetase Fusion Protein

A nitrocellulose filter binding assay (Ferst, Alan R. et al. *Biochemistry* 14l (1975)) was done to determine what fraction of the purified GST-lysyl-tRNA synthetase fusion protein was active. The amount of active protein was determined by measuring complex formation of [$^3$]H-lysine with ATP and the lysyl-tRNA synthetase. This reaction was done in a 50 µl volume containing: 50 mM Bis-Tris (pH 5.8), 10 mM MgCl$_2$, 30 mM KCl, 20 mM DTT, 4 mM ATP, 40 µM of a 1:10. ratio of [$^3$]-lysine: unlabeled lysine, 1.2 units inorganic pyrophosphatase (Sigma) and between 50 and 400 nM lysyl-tRNA synthetase. The reaction was incubated at 25° C. for 20 minutes. The reaction product was counted in duplicate by applying 15 µl of the reaction to a prewet nitrocellulose filter and washed 10× with 1 ml cold 50 mM Bis-Tris, pH 5.8. The filters were dried under vacuum and counted in 9 ml Hydrofluor, 1 ml 1 N HCl.

EXAMPLE 13

Activity Assay of the Purified GST-*P. carinii* Lysyl-tRNA Synthetase Fusion Protein and the Purified, Cleaved *P. carinii* Lysyl-tRNA Synthetase Protein A tRNA charging assay was used to determine the enzymatic activity of the proteins. The 50 µl reaction contained: 0.1 M Hepes, pH 7.5, 20 mM KCl, 20 mM MgCl$_2$, 0.02 M β-mercaptoethanol, 4.4 mH ATP, 100 µpH brewers yeast tRNA or 2 µM *E. coli* purified lysine tRNA (Sigma), 20 µM of a 1:10 ratio of [$^3$H]-lysine unlabeled lysine. To initiate the reaction, either the GST-lysine tRNA synthetase fusion protein was added to a final concentration of 2.2 µM or the cleaved lysyl-tRNA synthetase protein was added to a final concentration of 0.31 µM. (Protein concentrations were determned by comparison to standards of known amounts of protein visualized on a polyacrylamide gel stained with Coomassie blue. Control reactions were done in which either the tRNA or the lysyl-tRNA synthetase protein was not added. The reaction was incubated at 25° C. 10 µl aliquots were removed at 2 minutes, 4 minutes, 8 minutes and 16 minutes time points, applied to a Whatman 3 MM filter disc and soaked in 5% trichloroacetic acid (TCA) on ice. The filters were sequentially washed: 3× in 5% TCA on ice for 15', 1× with 100% ethanol on ice for 5', 1× with ether at room temperature for 5'. The filters were dried under a heat lamp and counted in 3 ml of Beta-fluor in a scintillation counter.

EXAMPLE 14

Activity Assay of the Purified GST-Tyrosyl-tRNA Synthetase Fusion Protein and the Purified, Cleaved Tyrosyl-tRNA Synthetase Protein The purified proteins were assayed for activity by measuring the incorporation of radiolabeled tyrosine on yeast tRNA. The assay conditions are modified from Chow and RajBhandary (*J. Biol. Chem.* 268:12855–12863 (1993)). The conditions were as follows: a 60 µl reaction contained 150 mH Tris HCl, pH 7.5; 150 mH KCl; 10 mM MgCl$_2$; 20 mM β-mercaptoethanol, 2 mM ATP, 25 µM tyrosine (22.5 µM unlabeled tyrosine with 2.5 µM $^3$H-tyrosine at 50 Ci/mmol, 1 mCi/ml), 0.1 mM crude yeast tRNA (brewers yeast, Boehringer Mannheim) and 10 µl of enzyme dilution (100 nM for the cleaved protein or 8–16 nM for the fusion protein). At timed intervalsa 10 ul aliquots of the enzyme assay were removed from the vial and spotted onto cellulose filters saturated with 5% TCA to stop the reaction. The filters were then washed for 15 minute intervals: 3 times in 5% TCA, once in 95% ethanol, and once in diethyl ether at 4° C. The filters were then air-dried and placed in scintillation vials with 10 ml scintillation fluid and the number of radioactive counts incorporated onto the tRNA was measured in a liquid scintillation counter. An example of the activity assay for the *P. carinii* tyrosyl-tRNA synthetase fused to GST is shown in FIG. 7.

EXAMPLE 15

Construction of Plasmids pQB169 pQB172 pYeK02 and pdYK1

Plasmid pHC4 carries the ADH promoter of *S. cerevisiae* and downstream of the promoter, the coding sequence for the cytochrome oxidase IV mitochondrial targeting peptide (Pinkham, J. et al., *Mol. Cell. Biol.*, 14:4643–4652, (1994); Hurt, E. C. et al., *J. Biol. Chem.*, 262:420–1424 (1987); Hurt, E. C., et al., *EMBO J.* 3:3149–3156 (1984)). Derivatives of plasmid pMC4 can be constructed which lack or interrupt the sequence encoding the mitochondrial targeting sequence (e.g., by insertion of a gene between the promoter and targeting sequence), permitting cytoplasmic expression. Alternatively, the ADH promoter of pHC4 can be excised and inserted into another suitable vector. pQB169 and pQB172, which were constructed for the expression of heterologous genes in yeast cytoplasm, are examples of vectors constructed in this manner.

pQB169 contains the constitutive ADH promoter, a polylinker and the ILS1 transcriptional terminator. A 450 bp fragment containing the constitutive ADH promoter (pADH) with its transcriptional start sites (but not a translational start site (i.e., ATG)) was amplified by PCR using plasmid pMC4 as template. Primers were designed to incorporate a HindIII site at the 5' end (primer JK-1; SEQ ID NO:22) of the fragment and a PstI site at the 3' end (primer JK-2; SEQ ID NO:23):

HindIII
JK-1: 5'-CCA AGA AGC TTG AAG TAA TAA TAG GCG CAT GC

Pst I
JK-2: 5'-CGT ACT GCA GGA TTG TAT GCT TGG TAT AGC

The resulting PCR product was cleaved with HindIII and PstI, and the HindIII-PstI fragment containing pADH was subcloned into the HindIII and PstI sites of vector YEplac181 (Gietz and Sugino, *Gene,* 74: 527–534 (1988)), a 2μ LEU2 yeast shuttle vector, to yield intermediate plasmid pQB147.

For efficient transcription termination, a 270 bp terminator fragment (tILS1) containing conserved transcription termination signals (Zaret and Sherman, *Cell,* 28:563–573 (1982)) was generated by PCR, using plasmid pQB89 as template. pQB89 is a derivative of YCplac33 (a URA3, CEN4 plasmid; Geitz and Sugino, *Gene,* 74:527–534 (1988))). pQ389 was constructed by subcloning a 6 kb BamHI fragment obtained from a λ clone (ATCC Accession No. 70323) containing a yeast genomic fragment which includes the ILS1 gene (yeast cytoplasmic isoleucyl-tRNA synthetase gene; Englisch et al., *Biol. Chem. Hoppe-Seyler,* 368:971–979 (1987)) into YCplac33.

The 270 bp tILS1 PCR fragment was engineered to have an EcoRI site at the 5' end (JK-5; SEQ ID NO:24), and a NarI site at the 3' end (JK-6; SEQ ID NO:25), and contains the 3' untranslated region of ILS1, including bases 3519–3846 of the ILS1 gene. The primers used to prepare this fragment were:

EcoRI
JK-5: 5'-GGA ATT CTG AAA ACA ACT CAT ATA AAT ACG

NarI
JK-6: 5'-GAG GCG CCC TCT TAT CAA TCC CCT CCT CAA CC

The resulting PCR product was cleaved with EcoRI and NarI. pQB147 was cleaved with EcoRI and NarI, and the EcoRI-NarI tILS1 fragment was subcloned into the EcoRI and NarI sites of the vector to yield expression vector pQB169. Transformants of *E. coli* DH5α containing pQB169 were obtained. Transcription of a gene inserted into this vector can be initiated from pADH, and translation can be initiated at the first ATG of the insert.

To make a single-copy (CEN) version of this vector, the expression cassette (pADH-polylinker-tILS1) of pQB169 was excised with HindIII and NarI, and was subcloned into the HindIII and NarI sites of HindIII-NarI cut YCplac111 (Gietz and Sugino, *Gene* 74:527–534 (1988)) to yield pQB172. Transformants of *E. coli* DH5α containing pQB172 were obtained.

EXAMPLE 16

Complementation of a krs1Δ Strain of *S. cerevisiae* by *P. carinii* LysRS Gene

Maintenance plasmid carrying *S. cerevisiae* KRS1 gene

The "maintenance plasmid" pYeK02 contains a PstI-SacI fragment (carrying the KRS1 gene encoding yeast cytoplasmic lysyl-tRNA synthetase) from pYK02 (Martinez, et al. *Mol. Gen. Genet.* 227:149–154 (1991)) subcloned into the BamHI site of pEMBLYe23 (Baldari and Cesarini, *Gene* 35:27–32 (1985)), a 2μ URA3 vector.

Construction of haploid krs1Δ strain CdYK02/pYeK02 pdYK1 was constructed by inserting the SphI-BsmI fragment from pYK04 (Martinez & Mirande, *Euro J. Biochem.* 207:1–11 (1992)) into pYK06 (Martinez & Mirande, *Euro J. Biochem.* 207:1–11 (1992)) which had been digested with SphI and SnaBI. Strain CC456 (Martinez, et al., *Mol Gen. Genet*$_0$ 227:149–154 (1991); genotype: MAT a/α his3/his3 leu2/leu2, ura3/ura3, trp1/trp1) was transformed with the SphI-SmaI fragment from pdYK1, selecting for Trp+. Transformants were screened by Southern analysis (Southern, *J. Mol. Biol.* 98:503–517 (1975)) for disruption of the KRS1 gene. The krs1::TRP1/KRS1 diploid thus generated was transformed with pYeK02a this transformant was sporulated, and a haploid. Trp+ Ura+ spore was identified and designated CdYK02/pYEK02. Its genotype is thus his3 leu2 ura3 krs1::TRP1/pYeK02 (URA3 KRS1).

*P. carinii* LysRS Gene in Yeast Expression Vector

A PCR product containing BglII and KpnI restriction sites at its ends was made from the cloned *P. carinii* lysyl-tRNA synthetase gene The PCR reaction contained 90 ng of the plasmid template Lys(–)introns 1,2,SK+ #16 and oligonucleotide primers 33 and 27. oligonucleotide primer 33 contains a KpnI site (GGTACC). Oligonucleotide primer 27 (see Example 6) contains a BglII site (AGATCT).

oligonucleotide primer 33:
GGTACCGGTAC-CTTTTTTTTTTTTTTTTTAAATACATAC (SEQ ID NO:46)

oligonucleotide primer 27:
CATAGATCTAATGTAGGATTATGTGAAAG

The reaction cycle was 99° C. for 1 minute, 55° C. for 30 seconds, 75° C. for 1 minute, repeated for 25 cycles. For the last cycle the sample was at 75° C. for 2 minutes instead of 1 minute. The PCR product was separated by electrophoresis on a 1.5% agarose gel, purified from the gel band, and digested for cloning.

The vector plasmid pQB169 (1 μg), was digested in a 30 μl volume with BamHI and KpnI. Plasmid Lys-introns 1,2/SK+16 (1.4 μg) was digested in a 30 μl volume with BamHI and BglII.

The PCR product lys[33,27] was digested in a 30 μl volume with BglII and BamHI. All digestions were done at 37° C. for 2 hours. The ligation reaction (10 μl) contained 100 ng of BamHI-KpnI digested plasmid pQB169, 6 μl of the BglII-KpnI digested PCR product lys[33,27] and 2 μl of the BamHI-BglII digested Lys(–)introns 1,2,SK+ #16 plasmid. The reaction mixture was incubated at room temperature for 1 to 2 hours. 50 μl of competent DH5α cells were transformed with 2 μl of the transformation reaction. Plasmids were isolated from 7 transformants and digested with BglII-KpnI to confirm the presence of an insert of the correct size. One such plasmid, Lys[33,27]/pQB169#1 (also referred to herein as pQB235) was analyzed further by partial DNA sequence determination and by restriction enzyme digestion to confirm the sequence and size of the insert.

Strain CdYK02/pYeK02 was transformed with either pQB169 (vector alone) or pQB235 (vector+*P. carinii* LysRS), selecting for Leu+ transformants.

Complementation of krs1Δ by *P. carinii* LysRS

A plasmid shuffle (Sikorski, R. S. & Boeke, *J. Methods Enzymol.* 194:302–318 (1991)) was attempted to check for complementation of the lethal krs1Δ mutation by *P. carinii* LysRS. Purified single transformants (Ura+ Trp+ Leu+) were streaked on 5-fluoro-orotic acid (5-FOA) plates to select against cells carrying the URA3 plasmid (Boeke, et al. *Mol. Gen. Genet.,* 197:345–346 (1984)). Only the pQB235 transformants grew on 5-FOA medium (at 30° C.), indicating that the pQB169 transformants could not survive without the maintenance plasmid pYeK02.

To check that the 5-FOA+ colonies that arose had not undergone gene conversion at either kzrs1Δ on the chromosome or URA3 on pYeK02, the following two experiments were done: (1) Rich medium (YPD) was inoculated with independent colonies and grown for at least 10 generations (>24 hours at 30° C.) to allow for plasmid loss. Cells were diluted and spread on rich (YPD) medium to yield about 200 colonies after 2 days at 30° C. These colonies were replica plated to SC-Ura, SC-Trp, SC-Leu, and SC medium (Rose, M. D., et al. *Methods in Yeast Genetics,* Cold Spring Harbor Laboratory Press, Cold Spring Harbor, N.Y., 1990). The plates were incubated overnight at 30° C. and scored the following day. All (800/800) colonies were Ura-Trp+ Leu+, indicating the cells had maintained the TRP1 disruption of KRS1 and were dependent on the LEU2 plasmid. (2) Plasmid DNA was isolated from the same YPD cultures by isolating total DNA transforming bacteria (DH5α), and preparing plasmid DNA from multiple independent bacterial transformants: Restriction analysis revealed that all (8/8) colonies contained the plasmid pQB235. Thus, the 5-FOA+ colonies have lost the maintenance plasmid, are dependent on a LEU2 plasmid, and that plasmid is pQB235, containing the *P. carinii* LysRS gene. This strain, QBY336 (his3 leu2 ura3 trp1 krs1::TRP1/pQB235 (LEU2 $p_{ADH}$-P.c. LysRS)) is therefore dependent on *P. carinii* LysRS.

EXAMPLE 17

Testing *P. carinii* LysRS Gene for Complementation of *S. cerevisiae* msk1 (Mitochondrial LysRS Gene)

Standard methods for yeast propagation and transformation were used (*Current Protocols in Molecular Biology,* Ausubel, F. M. et al., eds., John Wiley and Sons, 1992; Rose, et al., *Methods in Yeast Genetics,* Cold Spring Harbor Laboratory Press, Cold Spring Harbor, N.Y. (1990)).

QBY4=(EY722) (MATα ade2-1 his3-11,15 leu2-3,112 ura3-1 trp1-1 can1-100 Gal$^+$) (Elion, E. A. et al., Proc. Natl. Acad. Sci. USA 88:9392–9396 (1991))

QBY47=(W303∇MSK1) (MATα ade2-1 his3-11,15 leu2-3,112 ura3-2 trp1-1 msk1::HIS3) (Gatti, D. L. and Tzagoloff, A. *J. Mol. Biol.* 218:557–568 (1991))

QBY274 (=QBY4 kar1Δ15) was made by integrative transformation of W303 strains with pMR1593 (=YIp5 URA3 bla kar1Δ15); obtained from Mark Rose, Princeton, U.; *J. Cell. Biol.* 117:1277–1287 (1992)). Ten μg of pMR1593 linearized with BglII was used to direct integration into the KAR1 locus via integrative transformation in QBY4. Ura$^+$transformants were grown twice on complete synthetic medium containing 5-FOA (1 g/liter) to select for the replacement of KAR1 by the kar1Δ,15 allele. Chromosomal DNA was prepared from the resulting strain (10 purified independent isolates), restricted with NsiI and checked by Southern hybridization for the presence of the deletion in the chromosomal copy of the KAR1 gene, using a 600 bp fragment from plasmid pMR1593 as probe. The strains containing the kar1Δ15 allele were subsequently tested for their deficiency in karyogamy by mating assays.

QBY47(pQB218) was made by transformation of QBY47 with pQB218.

QBY74(pQB218) rho$^+$derivatives were made by cytoduction. 5×10$^6$ Cells from logarithmic phase cultures of QBY47 (pQB218) and QBY274 strains were mixed and spread onto a nitrocellulose filter laid on top of a YPD agar plate. The plate was incubated at 30° for 5 h. Cytoductants were then micromanipulated on YPD agar and allowed to form colonies; the colonies were later purified on SC-glycerol media lacking histidine and uracil to select for rho$^+$derivatives of QBY47(pQB218). Selection on 5-FOA plates following transformation was used to replace pQ3218 (MSK$^+$URA3$^+$) with the test plasmids, which were based on a LEU2-marked 2μ vector.

Construction of Positive Control Plasmid Bearing NSK, QB218 pQB42 is YEplac195 (Sugino, A., and Gietz, R. D. *Gene* 74:527–534 (1988)), a 2μURA3 vector. Plasmid pQB106 (pG11/T6) carrying the yeast MNSK1 gene (GenBank Accession No. X57360) has already been described (Gatti, D. L. and Tzagoloff, A. *J. Mol. Biol.* 218:557–568 (1991); ATCC® No. 77080, available from the American Type Culture Collection, 12301 Parklawn Drive, Rockville, Md. 20852-1776). pQB106 is an isolate out of an *S. cerevisiae* genomic library constructed with the LEU2-bearing shuttle vector YEp13 (Nasmyth, K. A. and Reed, S. I. *Proc. Natl. Acad. Sci. USA* 77:2119–2123 (1980)), that contains an approximately 6 kb insert of nuclear DNA and is capable of complementing a msk::HIS3 allele. Plasmid pQB218 was made by excising a 3 kb XbaI fragment comprising NSK1 from plasmid pQB106, and inserting it into pQB42.

Construction of pQB161

PQB111 and pQB136:

The presequence from the cytochrome oxidase IV was used in the mitochondrial import vectors pQB111 and pQB136. This sequence has been used to allow import of several heterologous proteins in the mitochondria (Hurt, E. C., et al., EMBO J. 3:3149–3156 (1984), Pinkham, J., et al., *Mol. and Cell. Biol.* 14:4643–4652, (1994)).

In order to construct pQB111, an SphI-XbaI fragment bearing the ADH1 promoter and 22 of the 25 amino acids of COXIV (cytochrome oxidase IV) presequence were excised from plasmid pMC4 (obtained from J. Pinkham University of Massachusetts, Amherst) (Bibus, C. R., et al., *J. Biol. Chem.* 263:13097–13102 (1988); Hurt E. C., et al., *J. Biol. Chem.* 262:1420–1424 (1987)) and cloned into the SphI and XbaI sites of YEplac195 (also referred to as pQB42) (Sugino, A., and Gietz, R. D. *Gene* 74:527–534 (1988)) to form pQB111.

Plasmid pQB136 is a derivative of PQB111 which allows construction of GST fusion proteins targeted to mitochondria. PCR was used to amplify the GST gene from pGEX-4T-2 (Pharmacia) using the following primers:

5'        G C G C T C T A G A T A T C T G C T T A T G T C-CCCTATACTAGGTTATTGG 3' (SEQ ID NO:26), and 5' GGGGTACCTCACGATGCGGCCGCTCGAG 3' (SEQ ID NO:27; the ATG underlined in the 5'-primer is the start site of GST; the bases in boldface specify amino acids 22–25 of the COXIV presequence). The 5' primer introduced an XbaI site (underlined), which when fused to the XbaI site in plasmid pQB111, restores the entire (25 amino acid residue) presequence of COXIV. The 3' primer introduces a KpnI site (underlined) downstream of the GST stop codon. The PCR product was cleaved with XbaI and KpnI and inserted into the XbaI and KpnI sites of pQB111 to yield pQB136.

pQB152

Plasmid pQB152 carrying a GST-MSM1 protein fusion was constructed by PCR amplification of the wild type MSM1 gene from plasmid pQB104 (pG72/T1) (Tzagoloff, A., et al., *Eur. J. Biochem.* 179:365–371 (1989)) using the following primers: 5' CCGCTCGAGCGATGCAATGTC-GATCAATTGTGC 3' (SEQ ID NO:28) and 5' GGGGTACCCCTTTTTCATGACCTCATATTCG 3' (SEQ ID NO:29). The PCR product was cleaved with XhoI and KpnI and cloned into the XhoI and KpnI sites of pQB136. In subsequent studies pQB152, encoding a GST-MSM1 fusion, was observed to complement msm1-1 and msm1::HIS3 strains on YEPG medium₀ pQB161 was made by transferring a GST fusion of the mitochondrial methionyl-tRNA synthetase from pQB152 on a KpnI-HindIII fragment to the same sites in pQB41 (a LEU2-based vector, also referred to as YEplac181; Gietz and Sugino, *Gene* 74:527–534 (1988)). Because restriction sites present on this plasmid proved to be useful for cloning purposes, the backbone from this plasmid is used as a substitute for a pQB111-like vector (i.e. it has the ADH promoter and 22 amino acids of the COXIV) except that the LEU2 marker is present on this vector instead of the URA3 marker.

Construction of Test Plasmid Bearing *P. carinii* Lysyl-tRNA Synthetase Gene, pQB189

In order to clone the lysyl-tRNA synthetase gene from *P. carinii* into the mitochondrial targeting vector, the gene was first amplified from plasmid Lys(−)introns 1,2,SK+ #16 using primer 5'lys-y (SEQ ID NO:30) and primer #29 (SEQ ID NO:31)).

5'lys-y: CAGACGTCTAGATATCTGCTTGGATC-CATGGAGGAATCTTCACCAAGT

29: CCTCGAGTTTTTTTTTTTTTTTT-TAAATACATAC

The PCR fragment had to be initially subcloned into the pT7Blue T-vector (Novagen) since the XbaI site within the #29 primer was too close to the end to be cleavable. The resulting plasmid is pQB188. A 1.9 kb fragment from an XbaI partial digest which contains the *P. carinii* lysyl-tRNA synthetase gene was cloned from pQB188 into a pQB161-XbaI cut backbone, and the resulting plasmid having the *P. carinii* lysyl-tRNA synthetase gene in the correct orientation was named pQB189.

Complementation Tests

In order to test complementation in the mitochondrial lysyl- tRNA synthetase disruption strain (QBY47), attempts were made initially to make the strain rho⁺(i.e. carrying functional mitochondria) through mating with QBY4. The resulting diploid strain gave rise to inviable spores. Functional mitochondria then had to be introduced through cytoduction by mating the strain with the disrupted allele and carrying the maintenance plasmid, QBY47 (pQB218), with strain QBY274 (QBY4 kar1Δ15).

To achieve a "plasmid shuffle," transformants of QBY47 (pQB218) with pQ3189 or pQB106 were plated on agar containing 5-FOA and to select against those cells carrying URA3 on pQB218. As expected, 5-FOA-resistant cells transformed with plasmid pQB106 could grow on glycerol media, but 5-FOA-resistant cells transformed with pQB189 were not able to grow on glycerol as carbon source.

The *P. carinii* lysyl-tRNA synthetase construct has a few extra amino acid sequences in between the mitochondrial targeting signal junction and the ORF which may compromise the correct export and processing of this fusion. When the junction fragment from plasmid pQB189 was sequenced a T was observed in lieu of the C at position 19 in the 5'lys-y primer sequence, in the codon immediately preceding the XbaI site, resulting in the presence of a phenylalanine residue instead of the expected leucine residue in the transit peptide. The peptide also contains two extra amino acid residues from an extra engineered BamHI site (underlined in the primer sequence encoding glycine and serine). These changes may affect import and or processing into the mitochondria. Alternatively the altered *P. carinii* lysyl-tRNA synthetase may enter the mitochondria but not recognize mitochondrial lysine tRNA

EXAMPLE 18

Testing *P. carinii* TyrRS Gene for Complementation of *S. cerevisiae* msy (Mitochondrial TyrRS Gene)

Yeast Strains

QBY55=(aW303ΔMSY1) MATa ade2-1 his3-11,15 leu2-112 ura3-1 trp1-msy1:LEU2 (Edwards, H and P. Schimmel *Cell* 51:643–649 (1987))

QBY4=(EY722) (MATα ade2-1 his3-11,15 leu2-3,112 ura3-1 trp1-1 can1-100 Gal⁺) (Elion, E. A. et al., *Proc. Natl. Acad. Sci. USA* 88:939209396 (1991))

QBY243=MATa/MATα ade2-1/ade2-1 ura3-1/ura3-1 his3,11-15/his3, 11-15 trp1-1/trp1-1 msy::LEU2/MSY⁺

QBY171=(D273-10B) (ATCC#24657) MATα mal rho⁺ This wild type rho⁺strain is used as the parental strain for all the mitochondrial point mutation strains.

QBY54=(C31/HL1dp⁺) (MATa his3Δleu2-3,112 msy1-1) (Edwards, H. and P. Schimmmel *Cell* 51:643–649 (1987))

Construction of Control Plasmids Bearing MSY

Plasmid pQB108 (pG26/T2) is a 2μ-based plasmid with a LEU2 marker that has been described previously (Edwards, H. and P. Schimmmel *Cell* 51:643–649 (1987)). Plasmid pQB182 is a URA3 version of plasmid pQB108 which was made by transferring a 2.3 kb HindIII/SalI fragment containing the portion of the MSY open reading frame (ORF) present on pQB108 into the respective sites in plasmid pQB136. Plasmid pQB207 contains the 3' end of the MSY gene (corresponding to codons 418 to the C terminal end of the MSY gene product, plus sequence 3' to the coding region which is complementary to the MSY-2# primer) amplified from yeast genomic DNA (Promega) using primers:

MSY-1#: GCAGTATGCTGATAGAGAGATTGA (SEQ ID NO:32)

MSY-2#: GAAGCTTCGCAAGTAGTAAAGATGAA (SEQ ID. NO:33)

cloned in pT7Blue T-vector (Novagen). Plasmid pQB229 contains the entire NSY open reading frame (ORF) and was made by cloning an SpeI-HindIII fragment from pQB207 into a pQB182 backbone. pQB229 contains most of the MSY ORF but lacks the 3' end. pQB207 contains a PCR fragment of the 3' end of the gene. The two MSY gene fragments were fused in plasmid pQB229 using the SpeI site (in the MSY coding region) and HindIII site (in the vectors) to restore the complete ORF.

Construction of Test Plasmids Bearing the *P. carinii* Tyrosyl tRNA Synthetase Gene A PCR fragment was made as in Example 8 using primers PcY5XE and universal primer (New England Biolabs) on pNTY4 as the template DNA. This fragment was ligated directly into T7Blue T-Vector (Novagen, Madison, Wis.) to produce pT7blueYX. pQB111 was constructed as in Example 17. Plasmid pQB195 was obtained by cloning an XbaI-KpnI fragment containing the P. carinii tyrosyl-tRNA synthetase gene from plasmid pT7blueYX into the corresponding sites in plasmid PQB111. An SphI-XbaI fragment from plasmid pQB195 was then used to transfer this fusion (of the ADH1 promoter and COXIV signal peptide coding sequence to the coding sequence of the P. carinii TyrRS gene) to plasmid pQB183, a 2μ-based plasmid with a LEU2 marker, thus creating plasmid pQB206 Plasmid pQB212 is a URA3-based 2μ plasmid which was made by ligating an XhoI-BamHI insert from PGEXYG18 (see Example 8) into the respective sites of the plasmid pQB151. Plasmid pQB213 was constructed in the same manner by ligating the same XhoI-BamHI insert from pGEXYG18 into the 2μ LEU2 plasmid pQB183.

Complementation Tests

Strains of S. cerevisiae having mutations (e.g., point mutations) in nuclear PET genes (petite or pet mutants), whose expression is required for the morphogenesis of respiratory-competent mitochondriae cannot grow on non-fermentable carbon sources such as glycerol media. However, because S. cerevisiae is a facultative anaerobee such strains are capable of growing on fermentable carbon sources such as glucose, in the absence of mitochondrial function. On rich media such as glucose, these "petite" strains exhibit the small colony phenotype for which they are named. The majority of mitochondrial proteins, including the mitochondrial aminoacyl-tRNA synthetases, are nuclear encoded, synthesized in the cytoplasm and imported into mitochondria. Petite mutants of S. cerevisiae having defects in genes encoding a mitochondrial aminoacyl-tRNA synthetases have been identified (see e.g., Tzagoloff, A. and A. M. Myers, Ann. Rev. Biochem. 55:249–285 (1986); Tzagoloff, A. and C. L. Diekmann, Microbiol. Rev. 54(9) :211–225 (1990); Myers, A. M., et al., EMBO J. 4(8) :2087–2092 (1985)).

Although pet strains having mutations in nuclear genes encoding components of the mitochondrial translational apparatus, such as mitochondrial aminoacyl-tRNA synthetase genes, can grow on glucose, these strains tend to lose their mitochondrial DNA at high frequency, converting to rho⁻ or rho⁰ strains, with large deletions in their mitochondrial DNA (rho⁻) or no mitochondrial DNA (rho⁰) (Tzagoloff, A. and A. M. Myers, Ann. Rev. Biochem. 55:249–285 (1986); Myers, A. M., et al., EMBO J. 4(8) :2087–2092 (1985)).

Functional mitochondria were introduced into strain QBY55 by mating with the wild type strain QBY4 and selecting for diploids on SC glycerol medium lacking leucine. The resulting rho⁺ diploid strain, QBY243 was transformed with negative control plasmids pQB111 (vector alone, without MSY insert) and pQB182 (MSY'), positive control plasmid pQB229 (MSY⁺), and test plasmids pQB195 (TyrRS gene of P. carinii) and pQB212 (GST-TyrRS fusion gene), then set for sporulation and tetrad dissection. Haploid progeny bearing markers from both the disrupted gene (LEU2) and the plasmid (URA3) were tested on glycerol media to evaluate complementation. Spores germinated from at least one full tetrad were analyzed in each case on various selective media. Growth on YEPG, containing 3% glycerol and 2% ethanol as carbon source, was observed only for disruption alleles transformed with pQB229 (bearing the complete wild type gene). The control strains used were QBY4 (W303), QBY55 (MSY::LEU2), QBY243, and QBY171 (another wild type rho⁺ strain). The negative complementation result was verified by analysis of additional tetrads.

Since complementation of a point mutation strain is often less stringent, complementation was also tested in strain QBY54. To this end, LEU2 versions of the P. carinii TyrRS vectors were created. The ability to grow on glycerol media was assessed following transformation and colony purification. Cells harboring plasmids pQB206 (TyrRS gene of P carinii) or plasmid pQB213 (GST-TyrRS fusion gene) failed to grow on YEPG plates, while the control plasmid PQB108 (which carries the 5' portion of the MSY gene) enabled growth on glycerol media indistinguishable from wild type calls. The control strains used were QBY4(W303), QBY54 (msy1-1), and QBY171 (another wild type rho⁺ strain).

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. An isolated nucleic acid which encodes at least a functional portion of a lysyl-tRNA synthetase of *Pneumocystis carinii,* said portion having catalytic activity or binding function.

2. The isolated nucleic acid of claim 1 wherein said portion has catalytic activity.

3. An isolated nucleic acid which encodes at least a functional portion of a tyrosyl-tRNA synthetase of *Pneumocystis carinii,* said portion having catalytic activity or binding function.

4. The isolated nucleic acid of claim 3 wherein said portion has catalytic activity.

5. An isolated nucleic acid which encodes a lysyl-tRNA synthetase of *Pneumocystis carinii* origin, and hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to a nucleic acid having a sequence set forth in SEQ ID NO: 40 or to a complement thereof.

6. An isolated nucleic acid which encodes a tyrosyl-tRNA synthetase of *Pneumocystis carinii* origin, and hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to a nucleic acid having a sequence set forth in SEQ ID NO: 44 or to a complement thereof.

7. An isolated nucleic acid which encodes a fusion protein comprising a lysyl-tRNA synthetase of *Pneumocystis carinii* origin or functional portion thereof, said portion having catalytic activity or binding function, wherein said nucleic acid hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having sequence SEQ ID NO:40 or the complement thereof.

8. An isolated nucleic acid which encodes a fusion protein comprising a tyrosyl-tRNA synthetase of *Pneumocystis carinii* origin or functional portion thereof, said portion having catalytic activity or binding function, wherein said nucleic acid hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having sequence SEQ ID NO:44 or the complement thereof.

9. An essentially pure nucleic acid which encodes at least a portion of a lysyl-tRNA synthetase of *Pneumocystis carinii* origin, said portion having catalytic activity or binding function, and which hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having a sequence of SEQ ID NO:40 or the complement thereof.

10. An essentially pure nucleic acid which encodes the amino acid sequence SEQ ID NO:41.

11. An essentially pure nucleic acid which encodes the amino acid sequence SEQ ID NO:45.

12. An essentially pure nucleic acid which encodes at least a portion of a tyrosyl-tRNA synthetase of *Pneumocystis carinii* origin, said portion having catalytic activity or binding function, and which hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having sequence SEQ ID NO:44 or the complement thereof.

13. An isolated nucleic acid comprising a nucleic acid that hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having the sequence in SEQ ID NO:40, or to DNA having the sequence in SEQ ID NO:44.

14. A recombinant vector comprising nucleic acid which encodes at least a functional portion of a lysyl-tRNA synthetase of *Pneumocystis carinii* origin, said portion having catalytic activity or binding function, wherein the nucleic acid hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having sequence SEQ ID NO:40 or the complement thereof.

15. The recombinant vector of claim 14 comprising nucleic acid which encodes a lysyl-tRNA synthetase.

16. The recombinant vector of claim 14, wherein said portion has catalytic activity.

17. A recombinant vector comprising nucleic acid which encodes at least a functional portion of a tyrosyl- tRNA synthetase of *Pneumocystis carinii* origin, said portion having catalytic activity or binding function, wherein the nucleic acid hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having sequence SEQ ID NO:44 or the complement thereof.

18. The recombinant vector of claim 17, wherein said portion has catalytic activity.

19. The recombinant vector of claim 17 comprising nucleic acid which encodes a tyrosyl-tRNA synthetase.

20. A recombinant vector comprising nucleic acid encoding a fusion protein comprising a lysyl-tRNA synthetase of *Pneumocystis carinii* origin or functional portion thereof, said portion having catalytic activity or binding function, wherein the nucleic acid hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having sequence SEQ ID NO:40 or the complement thereof.

21. A recombinant vector comprising nucleic acid encoding a fusion protein comprising a tyrosyl-tRNA synthetase of *Pneumocystis carinii* origin or functional portion thereof, said portion having catalytic activity or binding function, wherein the nucleic acid hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having sequence SEQ ID NO:44 or the complement thereof.

22. A host cell comprising a recombinant gene which can express a lysyl-tRNA synthetase of *Pneumocystis carinii* origin or a functional portion thereof, said portion having catalytic activity or binding function, wherein the gene hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having sequence SEQ ID NO:40 or the complement thereof.

23. A host cell comprising a recombinant nucleic acid encoding a fusion protein comprising a lysyl-tRNA synthetase of *Pneumocystis carinii* origin or functional portion thereof, said portion having catalytic activity or binding function, wherein said nucleic acid hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having sequence SEQ ID NO:40 or the complement thereof.

24. A host cell comprising a recombinant gene which can express a tyrosyl-tRNA synthetase of *Pneumocystis carinii* origin or a functional portion thereof, said portion having catalytic activity or binding function, wherein the gene hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having sequence SEQ ID NO:44 or the complement thereof.

25. A host cell comprising a recombinant nucleic acid encoding a fusion protein comprising a tyrosyl-tRNA synthetase of *Pneumocystis carinii* origin or functional portion thereof, said portion having catalytic activity or binding function, wherein said nucleic acid hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having sequence SEQ ID NO:44 or the complement thereof.

26. A host cell comprising a recombinant nucleic acid encoding a polypeptide comprising a lysyl-tRNA synthetase having SEQ ID NO:40 or a functional portion thereof having catalytic activity or binding function.

27. A method for producing a polypeptide comprising a lysyl-tRNA synthetase having SEQ ID NO:40 or a functional portion thereof having catalytic activity or binding function, comprising maintaining a host cell of claim 26 under conditions suitable for expression of the nucleic acid, whereby the encoded polypeptide is produced.

28. The method of claim 27 further comprising the step of isolating the polypeptide.

29. A host cell comprising a recombinant nucleic acid encoding a polypeptide comprising a tyrosyl-tRNA synthetase having SEQ ID NO:44 or a functional portion thereof having catalytic activity or binding function.

30. A method for producing a polypeptide comprising a tyrosyl-tRNA synthetase having SEQ ID NO:44 or a functional portion thereof having catalytic activity or binding function, comprising maintaining a host cell of claim 29 under conditions suitable for expression of the nucleic acid, whereby the encoded polypeptide is produced.

31. The method of claim 30 further comprising the step of isolating the polypeptide.

32. A method for producing isolated lysyl-tRNA synthetase of *Pneumocystis carinii* origin, comprising the following steps:
   a) providing host cells containing a gene encoding lysyl-tRNA synthetase of *Pneumocystis carinii* origin;
   b) maintaining the host cells under conditions in which the gene is expressed; and
   c) isolating said lysyl-tRNA synthetase from the host cells.

33. A method for producing isolated tyrosyl-tRNA synthetase of *Pneumocystis carinii* origin, comprising the following steps:
   a) providing host cells containing a gene encoding tyrosyl-tRNA synthetase of Pneumocystis carinii origin;
   b) maintaining the host cells under conditions in which the gene is expressed; and
   c) isolating said tyrosyl-tRNA synthetase from the host cells.

34. A method for producing a polypeptide comprising a lysyl-tRNA synthetase of *Pneumocystis carinii* origin or a functional portion thereof, said portion having catalytic activity or binding function, comprising maintaining a host cell comprising a nucleic acid encoding said polypeptide under conditions suitable for expression of the nucleic acid, whereby the encoded polypeptide is produced, wherein said nucleic acid hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having sequence SEQ ID NO:40 or the complement thereof.

35. The method of claim 34 further comprising the step of isolating the polypeptide.

36. A method for producing a polypeptide comprising a tyrosyl-tRNA synthetase of *Pneumocystis carinii* origin or a functional portion thereof, said portion having catalytic activity or binding function, comprising maintaining a host cell comprising a nucleic acid encoding said polypeptide under conditions suitable for expression of the nucleic acid, whereby the encoded polypeptide is produced, wherein said nucleic acid hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having sequence SEQ ID NO:44 or the complement thereof.

37. The method of claim 36 further comprising the step of isolating the polypeptide.

38. A tester strain comprising host cells containing a lysyl-tRNA synthetase gene capable of expressing a lysyl-tRNA synthetase of *Pneumocystis carinii* origin or a functional portion thereof, said portion having catalytic activity or binding function, wherein the gene complements or substitutes in function for a host cell aminoacyl-tRNA synthetase gene, and wherein said gene hybridizes under conditions of hybridization overnight at 40° C. in 5× SSC, 1× Denhardt's solution, 0.1% SDS. 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having sequence SEQ ID NO:40 or the complement thereof.

39. The tester strain of claim 38 in which a host cell aminoacyl-tRNA synthetase gene has been lost or has been altered relative to wild type so as to make no gene product, a gene product which is inactive, or a gene product which can be conditionally made inactive.

40. A tester strain comprising host cells containing a tyrosyl-tRNA synthetase gene capable of expressing a tyrosyl-tRNA synthetase of *Pneumocystis carinii* origin or a functional portion thereof, said portion having catalytic activity or binding function, wherein the gene complements or substitutes in function for a host cell aminoacyl-tRNA synthetase gene, and wherein said gene hybridizes under conditions of hybridization overnight at 40° C. in 5× SSC, 1× Denhardt's solution, 0.1% SDS, 50% formamide, 0.1 mg/ml denatured, sheared salmon sperm DNA, washing twice in 2× SSC, 1.0% SDS at room temperature for 20 minutes and washing twice in 0.5× SSC, 1.0% SDS at 65° C. for 1 hour, to DNA having sequence SEQ ID NO:44 or the complement thereof.

41. The tester strain of claim 40 in which a host cell aminoacyl-tRNA synthetase gene has been lost or has been altered relative to wild type so as to make no gene product, a gene product which is inactive, or a gene product which can be conditionally made inactive.

* * * * *

SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: other nucleic acid (ix) FEATURE:
      (A) NAME/KEY: modified_base
      (B) LOCATION: 6
      (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 18
        (D) OTHER INFORMATION: /mod_base= i (ix) FEATURE:
        (A) NAME/KEY: modified_base
        (B) LOCATION: 21
        (D) OTHER INFORMATION: /mod_base= i (xi) SEQUENCE DESCRIPTION: SEQ ID NO:1:

TTYMTNGARG TNGARACNCC NATGATG                                    27

(2) INFORMATION FOR SEQ ID NO:2:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 24
        (D) OTHER INFORMATION: /mod_base= i (xi) SEQUENCE DESCRIPTION: SEQ ID NO:2:

TACMAYTCNA KCATNGTRAA YTCNGGRTTR TG                               32

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

AAAYTWTATT GGGGWACWGC WCCWACWGG                                  29

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

TTGATCWACW CCWCCAAATT GACAATC                                    27

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: modified_base
        (B) LOCATION: 11
        (D) OTHER INFORMATION: /mod_base= i (ix) FEATURE:
        (A) NAME/KEY: modified_base
        (B) LOCATION: 26
        (D) OTHER INFORMATION: /mod_base= i (ix) FEATURE:
        (A) NAME/KEY: modified_base
        (B) LOCATION: 29
        (D) OTHER INFORMATION: /mod_base= i (xi) SEQUENCE DESCRIPTION: SEQ ID NO:5:

GCGAATTCGG NTGGGAYTGY CAYGGNCTNC C                                        31

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 18
        (D) OTHER INFORMATION: /mod_base= i (ix) FEATURE:
        (A) NAME/KEY: modified_base
        (B) LOCATION: 21
        (D) OTHER INFORMATION: /mod_base= i (xi) SEQUENCE DESCRIPTION: SEQ ID NO:6:

GGNARNGTCC ANGGNGTNGT NGTCCA                                             26

(2) INFORMATION FOR SEQ ID NO:7:

(i) SEQUENCE CHARACTERISTICS:
        (A) LENGTH: 30 base pairs
        (B) TYPE: nucleic acid

```
        (C) STRANDEDNESS: single
        (D) TOPOLOGY: linear (ii) MOLECULE TYPE: other nucleic acid (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 15
        (D) OTHER INFORMATION: /mod_base= i (xi) SEQUENCE DESCRIPTION: SEQ ID NO:7:

TTYRCNAAYG CNGGNATGAA YCARTTYAAA                                           30

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: modified_base
        (B) LOCATION: 4
        (D) OTHER INFORMATION: /mod_base= i (ix) FEATURE:
        (A) NAME/KEY: modified_base
        (B) LOCATION: 22
        (D) OTHER INFORMATION: /mod_base= i (xi) SEQUENCE DESCRIPTION: SEQ ID NO:8:

RTTNCCCATC ATYTCRAARA ANGTRTGRTG                                           30

(2) INFORMATION FOR SEQ ID NO:9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: modified_base
        (B) LOCATION: 14
        (D) OTHER INFORMATION: /mod_base= i (ix) FEATURE:
        (A) NAME/KEY: modified_base
        (B) LOCATION: 17
        (D) OTHER INFORMATION: /mod_base= i (ix) FEATURE:
        (A) NAME/KEY: modified_base
        (B) LOCATION: 20
        (D) OTHER INFORMATION: /mod_base= i (ix) FEATURE:
        (A) NAME/KEY: modified_base
        (B) LOCATION: 23
        (D) OTHER INFORMATION: /mod_base= i
```

(xi) SEQUENCE DESCRIPTION: SEQ ID NO:9:

GCGAATTCTW YCTNACNGGN ACNGAYGARC AYGG                                        34

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 18
        (D) OTHER INFORMATION: /mod_base= i (ix) FEATURE:
        (A) NAME/KEY: modified_base
        (B) LOCATION: 21
        (D) OTHER INFORMATION: /mod_base= i (ix) FEATURE:
        (A) NAME/KEY: modified_base
        (B) LOCATION: 27
        (D) OTHER INFORMATION: /mod_base= i (ix) FEATURE:
        (A) NAME/KEY: modified_base
        (B) LOCATION: 33
        (D) OTHER INFORMATION: /mod_base= i (xi) SEQUENCE DESCRIPTION: SEQ ID NO:10:

GCGAATTCRT ANCCRATNGK NGCRTCNARC CANACRTA                                    38

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

TAATACGACT CACTATAGGG                                                        20

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

GTTTTCCCAG TCACGACGT                                                         19

(2) INFORMATION FOR SEQ ID NO:13:

(i) SEQUENCE CHARACTERISTICS:
        (A) LENGTH: 29 base pairs
        (B) TYPE: nucleic acid (C) STRANDEDNESS: single
            (D) TOPOLOGY: linear (ii) MOLECULE TYPE: other nucleic acid (xi) SEQUENCE DESCRIPTION: SEQ ID NO:13:

GGATCCGGAT CCATGGAGGA ATCTTCACC                                29

(2) INFORMATION FOR SEQ ID NO:14:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:14:

GCTCATAATA AACATTAGGC GTTAAATCTT CATTAATTTC TG                 42

(2) INFORMATION FOR SEQ ID NO:15:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:15:

CTAATGTTAT TATGAGCTTC GTTCTCGGCA TATTAATATG C                  41

(2) INFORMATION FOR SEQ ID NO:16:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:16:

CCATAATCCA AAGCTAAACA AAAATTCTCA TCAATAATTT G                  41

(2) INFORMATION FOR SEQ ID NO:17:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:17:

GTTTAGCTTT GGATTATGGA TTACCGCCTA CTGCAGGATG                    40

(2) INFORMATION FOR SEQ ID NO:18:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:18:

CGCGGATTCA TGGGATTTAC AAGTGAAATA G                              31

(2) INFORMATION FOR SEQ ID NO:19:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:19:

GTAAAACGAC GGCCAGT                                              17

(2) INFORMATION FOR SEQ ID NO:20:

(i) SEQUENCE CHARACTERISTICS:
            (A) LENGTH: 39 base pairs
            (B) TYPE: nucleic acid
            (C) STRANDEDNESS: double
            (D) TOPOLOGY: linear (ii) MOLECULE TYPE: other nucleic acid (ix) FEATURE:
            (A) NAME/KEY: CDS
            (B) LOCATION: 1..39

(xi) SEQUENCE DESCRIPTION: SEQ ID NO:20:

CTG GTT CCG CGT GGA TCC ATG GGA TTT ACA AGT GAA ATA             39
Leu Val Pro Arg Gly Ser Met Gly Phe Thr Ser Glu Ile
 1               5                  10

(2) INFORMATION FOR SEQ ID NO:21:

(i) SEQUENCE CHARACTERISTICS:
            (A) LENGTH: 13 amino acids
            (B) TYPE: amino acid
            (D) TOPOLOGY: linear (ii) MOLECULE TYPE: protein (xi) SEQUENCE DESCRIPTION: SEQ ID NO:21:

Leu Val Pro Arg Gly Ser Met Gly Phe Thr Ser Glu Ile
 1               5                  10

(2) INFORMATION FOR SEQ ID NO:22:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:22:

CCAAGAAGCT TGAAGTAATA ATAGGCGCAT GC                             32

(2) INFORMATION FOR SEQ ID NO:23:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:23:

CGTACTGCAG GATTGTATGC TTGGTATAGC                                30

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:24:

GGAATTCTGA AAACAACTCA TATAAATACG                                30

(2) INFORMATION FOR SEQ ID NO:25:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:25:

GAGGCGCCCT CTTATCAATC CCCTCCTCAA CC                             32

(2) INFORMATION FOR SEQ ID NO:26:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:26:

GCGCTCTAGA TATCTGCTTA TGTCCCCTAT ACTAGGTTAT TGG                 43

(2) INFORMATION FOR SEQ ID NO:27:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:27:

GGGGTACCTC ACGATGCGGC CGCTCGAG                                  28

(2) INFORMATION FOR SEQ ID NO:28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:28:

CCGCTCGAGC GATGCAATGT CGATCAATTG TGC                            33

(2) INFORMATION FOR SEQ ID NO:29:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:29:

```
GGGGTACCCC TTTTTCATGA CCTCATATTC G                          31
```

(2) INFORMATION FOR SEQ ID NO:30:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:30:

```
CAGACGTCTA GATATCTGCT TGGATCCATG GAGGAATCTT CACCAAGT        48
```

(2) INFORMATION FOR SEQ ID NO:31:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:31:

```
CCTCGAGTTT TTTTTTTTT TTTTTAAATA CATAC                       35
```

(2) INFORMATION FOR SEQ ID NO:32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:32:

```
GCAGTATGCT GATAGAGAGA TTGA                                  24
```

(2) INFORMATION FOR SEQ ID NO:33:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:33:

```
GAAGCTTCGC AAGTAGTAAA GATGAAA                               27
```

(2) INFORMATION FOR SEQ ID NO:34:

(i) SEQUENCE CHARACTERISTICS:
        (A) LENGTH: 287 base pairs (B) TYPE: nucleic acid
    (C) STRANDEDNESS: double
    (D) TOPOLOGY: linear (ii) MOLECULE TYPE: other nucleic acid (xi) SEQUENCE DESCRIPTION: SEQ ID NO:34:

```
GGTCGACTCT AGAGGATCTA CTAGTCATAT GGATTATGGA AGTGGAGACG CCGATGATGA      60

ATTTTATTCC AGGAGGTGCC AGTGCTAAGC CTTTTATCAC ACATCATAAC GAGCTTGATC     120

TTAATCTTTA TTTAAGAGTT GCACCTGAAT TATATTTAAA AATGTTAGTG ATAGGAGGCT     180

TGAATCGGGT TTATGAAATT GGAAAGCAAT TTAGGAATGA GAGTATTGAT CTTACGCACA     240

ACCCCGAATT CACCATGATA ATCGGATCCC CGGGTACCGA GCTCGAA                   287
```

(2) INFORMATION FOR SEQ ID NO:35:

(i) SEQUENCE CHARACTERISTICS:
    (A) LENGTH: 628 base pairs
    (B) TYPE: nucleic acid
    (C) STRANDEDNESS: double
    (D) TOPOLOGY: linear (ii) MOLECULE TYPE: other nucleic acid (xi) SEQUENCE DESCRIPTION: SEQ ID NO:35:

```
TTCGAGCTCG GTACCCGGGG ATCCGATTGC GAATTCGGGT GGGATTGTCA TGGGCTGCCT      60

GTTGAACATG AAATAGATAA AAAACTTGGG ATTAATGGAA AAGAAGATAT AATGGCAATA     120

GGGATTGAGA AGTGACGAGA AATGGTTTAT TTATATCTGT TTTACCATAT TCTAGATATA     180

ACAGTGAATG CCGTGCAATT GTTATGAGGT ATTCTGAGCA ATGGAGGGAG AAAATTGAAA     240

GATTAGGTAG ATGGATTGAG TTTGATAATG ATTACAAGAC TCTTGATACA TTATTTATGC     300

AATCAGTATG GTATATTTTT AAGAAGCTGT ATGAAAAGGG TAAAGTATAT AGAGGGTTTA     360

AGGTTATGCC ATATTCTACA GCATGCATGA CACCTCTTAG TAACTTTGAA GCTCAGCAGA     420

ATTATAAAAA AGTTAGTGAT CCATCTGGTA AATTTTTTGA ATATATGTTT TATATTCTAA     480

ATTGAATAGT TGTTATATCT TTTCCTTTAT TGGAAGATCC ATCTACATCA TTACTTGCAT     540

GGACCACCAC CCCCTGGACC CTCCCAATCC ATATGACTAG TAGATGGTGT AGAGTCGACC     600

TGCAGGCATG CAAGCTTTCC CTATAGTG                                        628
```

(2) INFORMATION FOR SEQ ID NO:36:

(i) SEQUENCE CHARACTERISTICS:
    (A) LENGTH: 693 base pairs
    (B) TYPE: nucleic acid
    (C) STRANDEDNESS: double
    (D) TOPOLOGY: linear (ii) MOLECULE TYPE: other nucleic acid (xi) SEQUENCE DESCRIPTION: SEQ ID NO:36:

```
GAATTCTTTC TGACGGGGAC GGACGAGCAC GGTATTAAAG TGGAACATTT ATTCATTTTT      60

TAGGATGATA CCAATGCCTT ATAGGTAGAG AAGGCGGCTT TAAAATCAGG TTTAAGTCCT     120

TCATTATTTT GTGAGAAAAT GTCGGAGCGT TTTAAATATT TGGCTAAATT AGCAAATATT     180

GATCATAAAG ATTTTAGTCG TACAACTAAT CCTAAACATT GTCAATCTGT CCAATGTTTT     240

TGGAAAGTTT TGAGGGATAA AGGATATATT TATGAAAATA AACATGAAGG ATGGTATGCT     300

GCACGTGATG AAACCTTTTA CCCATCTAAA GCTGTTAAAA AAATACGGAA TTCAGATGGT     360

GCTATGCTGA CTGTAAATGT TTTTATTATT TTTAAGTGTT TTTCTTAGTC ATAGTAGATT     420
```

| | |
|---|---|
| TCTATTGAGA CGGGTGCCAA TGTTGAATGG ATTTCTGAAA ATAATTATCA TTTCCGACTA | 480 |
| TCTAAATTTA AAAATCAGTT ATTGGATCAT TACAGAAAAA ATCCTTGTTT TGTTATTCCC | 540 |
| AGATCCGAAC AAAATAATTT ATATCATATG ATCGAGCAAG GATTAAATGA TATTAGTATA | 600 |
| TCTAGACCAA GCTCTCGCTA TTCATGGGGT ATTCGAGTAC CTGATGATGA GTCTCAAACA | 660 |
| ATATACGTCT GGCACGACGC CACCATCGGC TAT | 693 |

(2) INFORMATION FOR SEQ ID NO:37:

(i) SEQUENCE CHARACTERISTICS:
        (A) LENGTH: 590 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:37:

| | |
|---|---|
| AAACTTTATT GGGGAACTGC TCCTACAGGA AAACCTCATT GTGGTATATA TTTTTTATAA | 60 |
| TGTATGTATG ATTTATAATA CGTTTAGGAT ACTTTGTTCC TATGATCAAA ATTGCAGACT | 120 |
| TTTTAAAAGC AGAAGTTGAA GTAAGAGAAA TTAGTATATA TGAATGTAAT GTTTATGAAT | 180 |
| TTCAAGGTTA CTATTCTTTT TGCAGGTAAT GTTTATATTC TACATACCTA GTAACTCTAG | 240 |
| TAAAAAAGAT ATTCATGCAT TTTTAGATAA TCTTAAAGCA CCTATTGATA TTGTAAAATA | 300 |
| TAGGGCCAAA TATTATGAAT TTATTATTAA AGCTATTCTT AAATCAATTG GCGTTTCAAC | 360 |
| TGAAAAGCTC AGATTTGTTC TTGGATCGTC TTATCAACTA AGTTCTAAGT ATTGTATGGA | 420 |
| CAATTTTCGT CTTTGTACTA TTGTTACAGA ACATGATGCA AAACGCGCAG GAGCAGAAGT | 480 |
| TGTAACGCAA GTAGAAAACA GTCTACTTTC AGGACTTCTA TATCCAGGAA TGCAAGCTTT | 540 |
| AGATGAAGAA TATTTAGATA GTGATTGTCA ATTTGGAGGA GTAGATACAA | 590 |

(2) INFORMATION FOR SEQ ID NO:38:

(i) SEQUENCE CHARACTERISTICS:
        (A) LENGTH: 329 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:38:

| | |
|---|---|
| TTTGCGAATG CGGGGATGAA CCAGTTCAAA TCTATTTTTC TAGGCACGGT GGATTTATAT | 60 |
| AGTCCTCTTG GAAAGTTAAG AAGAGCGGTT AATTCTCAAA AGGTGAATTT TTTATGATAG | 120 |
| AAGAGGGATT TTAACTATTA TAAAAGGTTA TTAGAGCAGG AGGGAAACAT AATGGTAATA | 180 |
| TTTTTATGTA TTTTTATGTA TTTTTTTAAA AAATAATTTA GATCTTGAAG ATGTTGGAAA | 240 |
| AGATGTAAGT ATATGTTATT GTGAAATAAT TTAATAATTT AATATTATTT GAGAGTTATC | 300 |
| ACCACACCTT CTTCGAAATG ATGGGCAAC | 329 |

(2) INFORMATION FOR SEQ ID NO:39:

(i) SEQUENCE CHARACTERISTICS:
        (A) LENGTH: 2128 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:39:

```
CGCTCTAGAA CTAGTGGATC CCCCGGGCTG CAGGAATTCG GCACGAGAAA AAAACAAAAG    60

GATGGAGGAA TCTTCACCAA GTAACCCGAT AAAACAGCTT GGAAACCTTT GTTTAGATGA   120

AAGGTCGGGG AATATGTCT CAAAAACAGA GTTAAAAGA CGGTTAAAAC TTCAGGAAAA    180

AAAAGAAAAA AGAGAAGCTA AAGCATTAAC TACAGTTTCA CCAAAACCTG TTAAAAAACA   240

TGTTTCAGAA ATTAATGAAG ATTTAACGCC TAATGTTTTA TTTTTTGACT TTAAACTAAG   300

ATGAAATGAT TGTTAAGTTG TTATAGAAGT ATTATGAGCT TCGTTCTCGG CATATTAATA   360

TGCTTCGTGC TTCTAAAAAC TTAGATCCAT ATCCGCATAA GTTTTGTGTC AATATTCAGA   420

TTGAAGAATT CATTAAAACC TACAGTTTTA TGAAGAGAGG AGAAGTTAAT AGGGACATTA   480

TTGTTTCTGT TGCAGGAAGA ATATTAAATA AGCGGGATTC GGGTTCAAAA TTGCGTTTTT   540

ATGATCTTTG TGATGATGGT GCAAAAATTC AAGTGATGGC GCAAGCACAG GATTGTGAAA   600

AAGACTACTT AGAAATGCAT GAGCATATTC AGAGAGGAGA TATTGTAGGA ATTATTGGGT   660

ATCCTGGCCG TACATCGCCT AAAGGCAAAG GAAAGGATGA GGGAGAAGGA GGGGAATTGA   720

GTATATTTTG CAAAGAAATG GTGCTTTTAA GTCCATGTCT TCGTATGCTT CCAATGGAGC   780

GTCAAGGTTT AACAAATCAA GAAACAAGGT ATCGACAAAG ATATCTTGAT CTTATTATTA   840

ATAAATCTAC ACGAGAGAAG TTTATCATGA GATGTAAAAT TATTGAATAT ATTAGAAAAT   900

TTCTGAATTC ACGCAAGTTT CTAGAGGTTG AAACTCCTAT GATGAATTTT ATTCCAGGAG   960

GTGCCAGTGC TAAGCCTTTT ATCACACATC ATAACGAGCT TGATCTTAAT CTTTATTTAA  1020

GAGTTGCACC TGAATTATAT TTAAAAATGT TAGTGATAGG AGGCTTGAAT CGGGTTTATG  1080

AAATTGGAAA GCAATTTAGG AATGAGAGTA TTGATCTTAC GCATAATCCT GAATTTACAA  1140

GCTGCGAATT TTATTGTGCT TATGCAGATA TGTATGATCT TATTGATATA ACAGAAGAAA  1200

TGTTATCAAA TATGGTTTAT GAATTAACCG GTGATTACAA GATTAAATAT CATGTTAATG  1260

AGCTCGAAGA AGTTACTATT GATTTCTCAA GGCCATGGAA TCGTATAGAA GTTATTCCAT  1320

TTTTGGAAGA AAAACTCAAT GTTGTTTTTC CTCCTGGTGA TCAATTGCAT ACAGAAGAAA  1380

CGACTAACTT TCTTATCTCC TTATGTGAAA AACATCATGT TGAATATTTA CCACCCATAA  1440

CAAATTCTAG ATTATTTGAT AAGCTTATCA GTGAATTTTT GGAACCTCTA TGTCTTAATC  1500

CGACATTTTT GATAGGTCAT CCTCAAATTA TGTCTCCATT GGCAAAACAT CATAGATCTA  1560

ATGTAGGATT ATGTGAAAGA TTTGAATTAT TTGTAGCCTA TAAAGAACTT GTTAACGCAT  1620

ACACGGAACT AAATGATCCA GTTCAACAAC GAATAAGATT TGAGGAACAG ATCAAACAAA  1680

GGGATCAAGG AGATGATGAA GTTCAAATTA TTGATGAGAA TTTTTGTTTA GCTTTGTAAG  1740

TTTTATTGTT AAAATTATCT TGTTTTTTTA CTTTCAAAAG GGATTATGGA TTACCGCCTA  1800

CTGCAGGATG GGAATGGGA ATAGATCGAC TAGTAATGTT TTTGACGGAT TCATGCAATA  1860

TTAAGGAAGT TTTATTATTT CCTACAATGA AACCTGATGC TACTTCTAAT TGATTAATTT  1920

TTAATAAAAA TATTTTGAAA ATAATTATTT TCAAAATATA ACTCTTATTT TTGCATATAT  1980

TTTTGAATAA AAAAATTAAA CAAATTTGTA TTATAAAATG ATTAAAATTA CTTAAAATAT  2040

ATTAAAAGTG ATTATTTTAA AGTTATAAAT TCTTGTAAAA TAATCTATGT ATGTATTTAA  2100

AAAAAAAAAA AAAAAACTCG AGGGGGGG                                    2128
```

(2) INFORMATION FOR SEQ ID NO:40:

(i) SEQUENCE CHARACTERISTICS:
        (A) LENGTH: 1991 base pairs
        (B) TYPE: nucleic acid
        (C) STRANDEDNESS: double (D) TOPOLOGY: linear (ii) MOLECULE TYPE: cDNA (ix) FEATURE:
        (A) NAME/KEY: CDS
        (B) LOCATION: 29..1780

(xi) SEQUENCE DESCRIPTION: SEQ ID NO:40:

```
GAATTCGGCA CGAGAAAAAA ACAAAAGG ATG GAG GAA TCT TCA CCA AGT AAC            52
                               Met Glu Glu Ser Ser Pro Ser Asn
                                15              20

CCG ATA AAA CAG CTT GGA AAC CTT TGT TTA GAT GAA AGG TCG GGG GAA          100
Pro Ile Lys Gln Leu Gly Asn Leu Cys Leu Asp Glu Arg Ser Gly Glu
         25                  30                  35

TAT GTC TCA AAA ACA GAG TTA AAA AGA CGG TTA AAA CTT CAG GAA AAA          148
Tyr Val Ser Lys Thr Glu Leu Lys Arg Arg Leu Lys Leu Gln Glu Lys
 40                  45                  50

AAA GAA AAA AGA GAA GCT AAA GCA TTA ACT ACA GTT TCA CCA AAA CCT          196
Lys Glu Lys Arg Glu Ala Lys Ala Leu Thr Thr Val Ser Pro Lys Pro
     55                  60                  65

GTT AAA AAA CAT GTT TCA GAA ATT AAT GAA GAT TTA ACG CCT AAT GTT          244
Val Lys Lys His Val Ser Glu Ile Asn Glu Asp Leu Thr Pro Asn Val
 70                  75                  80                  85

TAT TAT GAG CTT CGT TCT CGG CAT ATT AAT ATG CTT CGT GCT TCT AAA          292
Tyr Tyr Glu Leu Arg Ser Arg His Ile Asn Met Leu Arg Ala Ser Lys
             90                  95                 100

AAC TTA GAT CCA TAT CCG CAT AAG TTT TGT GTC AAT ATT CAG ATT GAA          340
Asn Leu Asp Pro Tyr Pro His Lys Phe Cys Val Asn Ile Gln Ile Glu
        105                 110                 115

GAA TTC ATT AAA ACC TAC AGT TTT ATG AAG AGA GGA GAA GTT AAT AGG          388
Glu Phe Ile Lys Thr Tyr Ser Phe Met Lys Arg Gly Glu Val Asn Arg
        120                 125                 130

GAC ATT ATT GTT TCT GTT GCA GGA AGA ATA TTA AAT AAG CGG GAT TCG          436
Asp Ile Ile Val Ser Val Ala Gly Arg Ile Leu Asn Lys Arg Asp Ser
        135                 140                 145

GGT TCA AAA TTG CGT TTT TAT GAT CTT TGT GAT GAT GGT GCA AAA ATT          484
Gly Ser Lys Leu Arg Phe Tyr Asp Leu Cys Asp Asp Gly Ala Lys Ile
150                 155                 160                 165

CAA GTG ATG GCG CAA GCA CAG GAT TGT GAA AAA GAC TAC TTA GAA ATG          532
Gln Val Met Ala Gln Ala Gln Asp Cys Glu Lys Asp Tyr Leu Glu Met
                170                 175                 180

CAT GAG CAT ATT CAG AGA GGA GAT ATT GTA GGA ATT ATT GGG TAT CCT          580
His Glu His Ile Gln Arg Gly Asp Ile Val Gly Ile Ile Gly Tyr Pro
            185                 190                 195

GGC CGT ACA TCG CCT AAA GGC AAA GGA AAG GAT GAG GGA GAA GGA GGG          628
Gly Arg Thr Ser Pro Lys Gly Lys Gly Lys Asp Glu Gly Glu Gly Gly
        200                 205                 210

GAA TTG AGT ATA TTT TGC AAA GAA ATG GTG CTT TTA AGT CCA TGT CTT          676
Glu Leu Ser Ile Phe Cys Lys Glu Met Val Leu Leu Ser Pro Cys Leu
        215                 220                 225

CGT ATG CTT CCA ATG GAG CGT CAA GGT TTA ACA AAT CAA GAA ACA AGG          724
Arg Met Leu Pro Met Glu Arg Gln Gly Leu Thr Asn Gln Glu Thr Arg
230                 235                 240                 245

TAT CGA CAA AGA TAT CTT GAT CTT ATT ATT AAT AAA TCT ACA CGA GAG          772
Tyr Arg Gln Arg Tyr Leu Asp Leu Ile Ile Asn Lys Ser Thr Arg Glu
                250                 255                 260

AAG TTT ATC ATG AGA TGT AAA ATT ATT GAA TAT ATT AGA AAA TTT CTG          820
Lys Phe Ile Met Arg Cys Lys Ile Ile Glu Tyr Ile Arg Lys Phe Leu
            265                 270                 275

AAT TCA CGC AAG TTT CTA GAG GTT GAA ACT CCT ATG ATG AAT TTT ATT          868
Asn Ser Arg Lys Phe Leu Glu Val Glu Thr Pro Met Met Asn Phe Ile
```

```
                280                 285                 290
CCA GGA GGT GCC AGT GCT AAG CCT TTT ATC ACA CAT CAT AAC GAG CTT      916
Pro Gly Gly Ala Ser Ala Lys Pro Phe Ile Thr His His Asn Glu Leu
    295                 300                 305

GAT CTT AAT CTT TAT TTA AGA GTT GCA CCT GAA TTA TAT TTA AAA ATG      964
Asp Leu Asn Leu Tyr Leu Arg Val Ala Pro Glu Leu Tyr Leu Lys Met
310                 315                 320                 325

TTA GTG ATA GGA GGC TTG AAT CGG GTT TAT GAA ATT GGA AAG CAA TTT     1012
Leu Val Ile Gly Gly Leu Asn Arg Val Tyr Glu Ile Gly Lys Gln Phe
                330                 335                 340

AGG AAT GAG AGT ATT GAT CTT ACG CAT AAT CCT GAA TTT ACA AGC TGC     1060
Arg Asn Glu Ser Ile Asp Leu Thr His Asn Pro Glu Phe Thr Ser Cys
            345                 350                 355

GAA TTT TAT TGT GCT TAT GCA GAT ATG TAT GAT CTT ATT GAT ATA ACA     1108
Glu Phe Tyr Cys Ala Tyr Ala Asp Met Tyr Asp Leu Ile Asp Ile Thr
        360                 365                 370

GAA GAA ATG TTA TCA AAT ATG GTT TAT GAA TTA ACC GGT GAT TAC AAG     1156
Glu Glu Met Leu Ser Asn Met Val Tyr Glu Leu Thr Gly Asp Tyr Lys
    375                 380                 385

ATT AAA TAT CAT GTT AAT GAG CTC GAA GAA GTT ACT ATT GAT TTC TCA     1204
Ile Lys Tyr His Val Asn Glu Leu Glu Glu Val Thr Ile Asp Phe Ser
390                 395                 400                 405

AGG CCA TGG AAT CGT ATA GAA GTT ATT CCA TTT TTG GAA GAA AAA CTC     1252
Arg Pro Trp Asn Arg Ile Glu Val Ile Pro Phe Leu Glu Glu Lys Leu
                410                 415                 420

AAT GTT GTT TTT CCT CCT GGT GAT CAA TTG CAT ACA GAA GAA ACG ACT     1300
Asn Val Val Phe Pro Pro Gly Asp Gln Leu His Thr Glu Glu Thr Thr
            425                 430                 435

AAC TTT CTT ATC TCC TTA TGT GAA AAA CAT CAT GTT GAA TAT TTA CCA     1348
Asn Phe Leu Ile Ser Leu Cys Glu Lys His His Val Glu Tyr Leu Pro
        440                 445                 450

CCC ATA ACA AAT TCT AGA TTA TTT GAT AAG CTT ATC AGT GAA TTT TTG     1396
Pro Ile Thr Asn Ser Arg Leu Phe Asp Lys Leu Ile Ser Glu Phe Leu
    455                 460                 465

GAA CCT CTA TGT CTT AAT CCG ACA TTT TTG ATA GGT CAT CCT CAA ATT     1444
Glu Pro Leu Cys Leu Asn Pro Thr Phe Leu Ile Gly His Pro Gln Ile
470                 475                 480                 485

ATG TCT CCA TTG GCA AAA CAT CAT AGA TCT AAT GTA GGA TTA TGT GAA     1492
Met Ser Pro Leu Ala Lys His His Arg Ser Asn Val Gly Leu Cys Glu
                490                 495                 500

AGA TTT GAA TTA TTT GTA GCC TAT AAA GAA CTT GTT AAC GCA TAC ACG     1540
Arg Phe Glu Leu Phe Val Ala Tyr Lys Glu Leu Val Asn Ala Tyr Thr
            505                 510                 515

GAA CTA AAT GAT CCA GTT CAA CAA CGA ATA AGA TTT GAG GAA CAG ATC     1588
Glu Leu Asn Asp Pro Val Gln Gln Arg Ile Arg Phe Glu Glu Gln Ile
        520                 525                 530

AAA CAA AGG GAT CAA GGA GAT GAT GAA GTT CAA ATT ATT GAT GAG AAT     1636
Lys Gln Arg Asp Gln Gly Asp Asp Glu Val Gln Ile Ile Asp Glu Asn
    535                 540                 545

TTT TGT TTA GCT TTG GAT TAT GGA TTA CCG CCT ACT GCA GGA TGG GGA     1684
Phe Cys Leu Ala Leu Asp Tyr Gly Leu Pro Pro Thr Ala Gly Trp Gly
550                 555                 560                 565

ATG GGA ATA GAT CGA CTA GTA ATG TTT TTG ACG GAT TCA TGC AAT ATT     1732
Met Gly Ile Asp Arg Leu Val Met Phe Leu Thr Asp Ser Cys Asn Ile
                570                 575                 580

AAG GAA GTT TTA TTA TTT CCT ACA ATG AAA CCT GAT GCT ACT TCT AAT     1780
Lys Glu Val Leu Leu Phe Pro Thr Met Lys Pro Asp Ala Thr Ser Asn
            585                 590                 595

TGATTAATTT TTAATAAAAA TATTTTGAAA ATAATTATTT TCAAAATATA ACTCTTATTT   1840
```

```
TTGCATATAT TTTTGAATAA AAAAATTAAA CAAATTTGTA TTATAAAATG ATTAAAATTA        1900

CTTAAAATAT ATTAAAAGTG ATTATTTTAA AGTTATAAAT TCTTGTAAAA TAATCTATGT        1960

ATGTATTAAA AAAAAAAAAA AAAAACTCGA G                                      1991
```

(2) INFORMATION FOR SEQ ID NO:41:

(i) SEQUENCE CHARACTERISTICS:
      (A) LENGTH: 584 amino acids
      (B) TYPE: amino acid
      (D) TOPOLOGY: linear (ii) MOLECULE TYPE: protein (xi) SEQUENCE DESCRIPTION: SEQ ID NO:41:

```
Met Glu Glu Ser Ser Pro Ser Asn Pro Ile Lys Gln Leu Gly Asn Leu
 1               5                  10                  15

Cys Leu Asp Glu Arg Ser Gly Glu Tyr Val Ser Lys Thr Glu Leu Lys
                20                  25                  30

Arg Arg Leu Lys Leu Gln Glu Lys Lys Glu Lys Arg Glu Ala Lys Ala
            35                  40                  45

Leu Thr Thr Val Ser Pro Lys Pro Val Lys Lys His Val Ser Glu Ile
    50                  55                  60

Asn Glu Asp Leu Thr Pro Asn Val Tyr Tyr Glu Leu Arg Ser Arg His
65                  70                  75                  80

Ile Asn Met Leu Arg Ala Ser Lys Asn Leu Asp Pro Tyr Pro His Lys
                85                  90                  95

Phe Cys Val Asn Ile Gln Ile Glu Glu Phe Ile Lys Thr Tyr Ser Phe
            100                 105                 110

Met Lys Arg Gly Glu Val Asn Arg Asp Ile Ile Val Ser Val Ala Gly
        115                 120                 125

Arg Ile Leu Asn Lys Arg Asp Ser Gly Ser Lys Leu Arg Phe Tyr Asp
    130                 135                 140

Leu Cys Asp Asp Gly Ala Lys Ile Gln Val Met Ala Gln Ala Gln Asp
145                 150                 155                 160

Cys Glu Lys Asp Tyr Leu Glu Met His Glu His Ile Gln Arg Gly Asp
                165                 170                 175

Ile Val Gly Ile Ile Gly Tyr Pro Gly Arg Thr Ser Pro Lys Gly Lys
            180                 185                 190

Gly Lys Asp Glu Gly Glu Gly Gly Glu Leu Ser Ile Phe Cys Lys Glu
        195                 200                 205

Met Val Leu Leu Ser Pro Cys Leu Arg Met Leu Pro Met Glu Arg Gln
    210                 215                 220

Gly Leu Thr Asn Gln Glu Thr Arg Tyr Arg Gln Arg Tyr Leu Asp Leu
225                 230                 235                 240

Ile Ile Asn Lys Ser Thr Arg Glu Lys Phe Ile Met Arg Cys Lys Ile
                245                 250                 255

Ile Glu Tyr Ile Arg Lys Phe Leu Asn Ser Arg Lys Phe Leu Glu Val
            260                 265                 270

Glu Thr Pro Met Met Asn Phe Ile Pro Gly Gly Ala Ser Ala Lys Pro
        275                 280                 285

Phe Ile Thr His His Asn Glu Leu Asp Leu Asn Leu Tyr Leu Arg Val
    290                 295                 300

Ala Pro Glu Leu Tyr Leu Lys Met Leu Val Ile Gly Gly Leu Asn Arg
305                 310                 315                 320

Val Tyr Glu Ile Gly Lys Gln Phe Arg Asn Glu Ser Ile Asp Leu Thr
                325                 330                 335
```

```
His Asn Pro Glu Phe Thr Ser Cys Glu Phe Tyr Cys Ala Tyr Ala Asp
            340                 345                 350

Met Tyr Asp Leu Ile Asp Ile Thr Glu Glu Met Leu Ser Asn Met Val
        355                 360                 365

Tyr Glu Leu Thr Gly Asp Tyr Lys Ile Lys Tyr His Val Asn Glu Leu
    370                 375                 380

Glu Glu Val Thr Ile Asp Phe Ser Arg Pro Trp Asn Arg Ile Glu Val
385                 390                 395                 400

Ile Pro Phe Leu Glu Glu Lys Leu Asn Val Val Phe Pro Pro Gly Asp
                405                 410                 415

Gln Leu His Thr Glu Glu Thr Thr Asn Phe Leu Ile Ser Leu Cys Glu
            420                 425                 430

Lys His His Val Glu Tyr Leu Pro Pro Ile Thr Asn Ser Arg Leu Phe
        435                 440                 445

Asp Lys Leu Ile Ser Glu Phe Leu Glu Pro Leu Cys Leu Asn Pro Thr
    450                 455                 460

Phe Leu Ile Gly His Pro Gln Ile Met Ser Pro Leu Ala Lys His His
465                 470                 475                 480

Arg Ser Asn Val Gly Leu Cys Glu Arg Phe Glu Leu Phe Val Ala Tyr
                485                 490                 495

Lys Glu Leu Val Asn Ala Tyr Thr Glu Leu Asn Asp Pro Val Gln Gln
            500                 505                 510

Arg Ile Arg Phe Glu Glu Gln Ile Lys Gln Arg Asp Gln Gly Asp Asp
        515                 520                 525

Glu Val Gln Ile Ile Asp Glu Asn Phe Cys Leu Ala Leu Asp Tyr Gly
    530                 535                 540

Leu Pro Pro Thr Ala Gly Trp Gly Met Gly Ile Asp Arg Leu Val Met
545                 550                 555                 560

Phe Leu Thr Asp Ser Cys Asn Ile Lys Glu Val Leu Leu Phe Pro Thr
                565                 570                 575

Met Lys Pro Asp Ala Thr Ser Asn
            580

(2) INFORMATION FOR SEQ ID NO:42:

(i) SEQUENCE CHARACTERISTICS:
        (A) LENGTH: 2993 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..2934

(xi) SEQUENCE DESCRIPTION: SEQ ID NO:42:

ATA GAT AAA AAA CTT GGG ATT AAT GGA AAA GAA GAT ATA ATG GCA ATA        48
Ile Asp Lys Lys Leu Gly Ile Asn Gly Lys Glu Asp Ile Met Ala Ile
585                 590                 595                 600

GGG ATT GAG AAA TAT AAC AGT GAA TGC CGT GCA ATT GTT ATG AGG TAT        96
Gly Ile Glu Lys Tyr Asn Ser Glu Cys Arg Ala Ile Val Met Arg Tyr
                605                 610                 615

TCT GAG CAA TGG AGG GAG AAA ATT GAA AGA TTA GGT AGA TGG ATT GAG       144
Ser Glu Gln Trp Arg Glu Lys Ile Glu Arg Leu Gly Arg Trp Ile Glu
            620                 625                 630

TTT GAT AAT GAT TAC AAG ACT CTT GAT ACA TTA TTT ATG CAA TCA GTA       192
Phe Asp Asn Asp Tyr Lys Thr Leu Asp Thr Leu Phe Met Gln Ser Val
```

-continued

|  |  |  |  |  |  |  |  |  |  |  |  |  |  |  |  |
|---|---|---|---|---|---|---|---|---|---|---|---|---|---|---|---|
| | | 635 | | | | 640 | | | | 645 | | | | | |
| TGG | TAT | ATT | TTT | AAG | AAG | CTG | TAT | GAA | AAG | GGT | AAA | GTA | TAT | AGA | GGG | 240 |
| Trp | Tyr | Ile | Phe | Lys | Lys | Leu | Tyr | Glu | Lys | Gly | Lys | Val | Tyr | Arg | Gly | |
| | 650 | | | | 655 | | | | 660 | | | | | | |
| TTT | AAG | GTT | ATG | CCA | TAT | TCT | ACA | GCA | TGC | ATG | ACA | CCT | CTT | AGT | AAC | 288 |
| Phe | Lys | Val | Met | Pro | Tyr | Ser | Thr | Ala | Cys | Met | Thr | Pro | Leu | Ser | Asn | |
| 665 | | | | | 670 | | | | 675 | | | | | 680 | | |
| TTT | GAA | GCT | CAG | CAG | AAT | TAT | AAA | AAA | GTT | AGT | GAT | CCA | TCT | GTT | GTT | 336 |
| Phe | Glu | Ala | Gln | Gln | Asn | Tyr | Lys | Lys | Val | Ser | Asp | Pro | Ser | Val | Val | |
| | | | | 685 | | | | 690 | | | | | 695 | | | |
| ATA | TCT | TTT | CCT | TTA | TTG | GAA | GAT | CCA | TCT | ACA | TCA | TTA | CTT | GCA | TGG | 384 |
| Ile | Ser | Phe | Pro | Leu | Leu | Glu | Asp | Pro | Ser | Thr | Ser | Leu | Leu | Ala | Trp | |
| | | | 700 | | | | 705 | | | | 710 | | | | | |
| ACG | ACA | ACA | CCT | TGG | ACA | TTG | CCA | TCA | CAT | CTT | AAT | TTA | TGT | GTG | AAT | 432 |
| Thr | Thr | Thr | Pro | Trp | Thr | Leu | Pro | Ser | His | Leu | Asn | Leu | Cys | Val | Asn | |
| | | 715 | | | | 720 | | | | 725 | | | | | | |
| CCT | GAT | TTT | GAA | TAT | ATC | AAG | ATA | TAT | GAT | GAA | GCT | TCT | GGA | GAG | AAT | 480 |
| Pro | Asp | Phe | Glu | Tyr | Ile | Lys | Ile | Tyr | Asp | Glu | Ala | Ser | Gly | Glu | Asn | |
| | 730 | | | | 735 | | | | 740 | | | | | | | |
| TAT | ATT | TTA | TTA | GAA | AAA | TGT | TTG | AGT | ATT | CTT | TAT | AAA | GAT | CCT | AAA | 528 |
| Tyr | Ile | Leu | Leu | Glu | Lys | Cys | Leu | Ser | Ile | Leu | Tyr | Lys | Asp | Pro | Lys | |
| 745 | | | | | 750 | | | | 755 | | | | | 760 | | |
| AAT | GCT | AAA | TTT | ACA | AAA | TTG | CAA | ACT | ATT | AAA | GGT | GCT | GAT | ATG | AAA | 576 |
| Asn | Ala | Lys | Phe | Thr | Lys | Leu | Gln | Thr | Ile | Lys | Gly | Ala | Asp | Met | Lys | |
| | | | | 765 | | | | 770 | | | | | 775 | | | |
| GGT | TGG | AAA | TAT | GAT | CCA | CCT | TTT | TAT | TAT | TTT | TAT | GAG | CGT | TTT | AAA | 624 |
| Gly | Trp | Lys | Tyr | Asp | Pro | Pro | Phe | Tyr | Tyr | Phe | Tyr | Glu | Arg | Phe | Lys | |
| | | | 780 | | | | 785 | | | | 790 | | | | | |
| GAA | AGG | GCA | TTT | AAC | GTT | CTT | TTG | GCT | CAA | TAC | GTT | ACT | TCT | GAT | AAT | 672 |
| Glu | Arg | Ala | Phe | Asn | Val | Leu | Leu | Ala | Gln | Tyr | Val | Thr | Ser | Asp | Asn | |
| | | 795 | | | | 800 | | | | 805 | | | | | | |
| GGC | ACT | GGA | ATT | GTT | CAT | CAA | GCT | CCA | GCA | TTT | GGT | GAA | GAT | GAT | TAT | 720 |
| Gly | Thr | Gly | Ile | Val | His | Gln | Ala | Pro | Ala | Phe | Gly | Glu | Asp | Asp | Tyr | |
| | 810 | | | | 815 | | | | 820 | | | | | | | |
| AAT | GTG | GCT | TTT | GAG | AAT | GGA | ATT | ATT | GAT | GAG | AAT | TTT | TAT | CCT | CCT | 768 |
| Asn | Val | Ala | Phe | Glu | Asn | Gly | Ile | Ile | Asp | Glu | Asn | Phe | Tyr | Pro | Pro | |
| 825 | | | | | 830 | | | | 835 | | | | | 840 | | |
| TGC | CCA | TTG | GAT | GAA | AAA | GGG | AAT | TTT | ACA | GCT | GAA | GTT | TCT | GAT | TTT | 816 |
| Cys | Pro | Leu | Asp | Glu | Lys | Gly | Asn | Phe | Thr | Ala | Glu | Val | Ser | Asp | Phe | |
| | | | | 845 | | | | 850 | | | | | 855 | | | |
| GCT | GGG | ATG | TAT | GTT | AAA | GAT | GCT | GAT | AAA | GCT | ATA | CAG | AAA | GTT | CTT | 864 |
| Ala | Gly | Met | Tyr | Val | Lys | Asp | Ala | Asp | Lys | Ala | Ile | Gln | Lys | Val | Leu | |
| | | | 860 | | | | 865 | | | | 870 | | | | | |
| AAA | CAA | AAA | AAA | AGA | TTG | GTT | ATT | CAA | AGT | CAA | ATA | ATA | CAT | AGT | TAT | 912 |
| Lys | Gln | Lys | Lys | Arg | Leu | Val | Ile | Gln | Ser | Gln | Ile | Ile | His | Ser | Tyr | |
| | | 875 | | | | 880 | | | | 885 | | | | | | |
| CCA | TTT | TGT | TGG | AGA | TCT | GAT | ACA | CCT | CTT | TTA | TAT | AGA | GTA | GTT | CCA | 960 |
| Pro | Phe | Cys | Trp | Arg | Ser | Asp | Thr | Pro | Leu | Leu | Tyr | Arg | Val | Val | Pro | |
| | 890 | | | | 895 | | | | 900 | | | | | | | |
| TCG | TGG | TTT | GTA | AAA | GTT | AAA | GAA | TCT | ACA | AAA | GAG | ATG | CTA | GAA | GCT | 1008 |
| Ser | Trp | Phe | Val | Lys | Val | Lys | Glu | Ser | Thr | Lys | Glu | Met | Leu | Glu | Ala | |
| 905 | | | | 910 | | | | 915 | | | | | 920 | | | |
| CTT | GAA | TCA | ACT | AGA | TGG | GTG | CCC | TCG | TTT | GTT | AAG | GAT | AAA | CGT | TTT | 1056 |
| Leu | Glu | Ser | Thr | Arg | Trp | Val | Pro | Ser | Phe | Val | Lys | Asp | Lys | Arg | Phe | |
| | | | 925 | | | | 930 | | | | 935 | | | | | |
| GCG | AAT | TGG | ATT | ACA | GGT | TGT | AGA | GAT | TGG | AAT | ATT | TCT | CGA | AAT | CGT | 1104 |
| Ala | Asn | Trp | Ile | Thr | Gly | Cys | Arg | Asp | Trp | Asn | Ile | Ser | Arg | Asn | Arg | |
| | | | 940 | | | | 945 | | | | 950 | | | | | |
| TAT | TGG | GGA | ACT | CCC | ATA | CCT | TTA | TGG | GTT | TCT | GAT | GAT | TTT | GAA | GAA | 1152 |
| Tyr | Trp | Gly | Thr | Pro | Ile | Pro | Leu | Trp | Val | Ser | Asp | Asp | Phe | Glu | Glu | |

```
                  955                 960                 965
ATT GTA TGT ATA GGT TCA GTT TCT GAG CTT GAG GAA CTC TCT GGA GTG    1200
Ile Val Cys Ile Gly Ser Val Ser Glu Leu Glu Glu Leu Ser Gly Val
        970                 975                 980

CGA AAT TTG ACA GAT ATT CAT CGA GAT AAG ATA GAT CAC ATT ACA ATT    1248
Arg Asn Leu Thr Asp Ile His Arg Asp Lys Ile Asp His Ile Thr Ile
985                 990                 995                1000

CCC TCT AAA AAA GGA AAA AAT GCT CTT AAA AGA ATA GAA GAT GTG TTT    1296
Pro Ser Lys Lys Gly Lys Asn Ala Leu Lys Arg Ile Glu Asp Val Phe
                1005                1010                1015

GAT TGT TGG TTT GAA TCT GGA AGT ATG CCT TAT GCA TCT GTA TAT TAT    1344
Asp Cys Trp Phe Glu Ser Gly Ser Met Pro Tyr Ala Ser Val Tyr Tyr
            1020                1025                1030

CCA TTT CAA AAT TCT GAG AAT TTT ATG GAA AAA TTC CCT GCT GAT TTT    1392
Pro Phe Gln Asn Ser Glu Asn Phe Met Glu Lys Phe Pro Ala Asp Phe
        1035                1040                1045

ATT GCA GAA GGT CTT GTA CAA ACT CGT GGT TGG TTT TAT ACC CTT CTT    1440
Ile Ala Glu Gly Leu Val Gln Thr Arg Gly Trp Phe Tyr Thr Leu Leu
    1050                1055                1060

GTT CTT GGT GTT CAA TTG TTT GGG ATT GCA CCT TTC AAA AAT GTT ATT    1488
Val Leu Gly Val Gln Leu Phe Gly Ile Ala Pro Phe Lys Asn Val Ile
1065                1070                1075                1080

GTG AAT GGA TTG GTT CTT GCT TCT GAT GGG AAA AAG ATG TCA AAA CGC    1536
Val Asn Gly Leu Val Leu Ala Ser Asp Gly Lys Lys Met Ser Lys Arg
                1085                1090                1095

CTT AAG AAT TAT CCT GAA TTA TCT ATT GTT TTA GAC AAG TAT GGT GCA    1584
Leu Lys Asn Tyr Pro Glu Leu Ser Ile Val Leu Asp Lys Tyr Gly Ala
            1100                1105                1110

GAT GCA TTA CGA TTG TAT CTT ATT AAC TCC CCT GTT GTA CGT GCT GAA    1632
Asp Ala Leu Arg Leu Tyr Leu Ile Asn Ser Pro Val Val Arg Ala Glu
        1115                1120                1125

CCT TTA AAA TTT AAG GAA GAT GGT GTT AAA GAT GTT GTT GCA AAA GTT    1680
Pro Leu Lys Phe Lys Glu Asp Gly Val Lys Asp Val Val Ala Lys Val
    1130                1135                1140

ATT ATT CCA TGG TGG AAT AGT TAT AAT TTT TTT GAA ATG CAA GTG AAA    1728
Ile Ile Pro Trp Trp Asn Ser Tyr Asn Phe Phe Glu Met Gln Val Lys
1145                1150                1155                1160

CTA CTG AAG AAA ACT CAT AAT ATC GAC TTT ATG TAT AAT CTT TCT AAT    1776
Leu Leu Lys Lys Thr His Asn Ile Asp Phe Met Tyr Asn Leu Ser Asn
                1165                1170                1175

GAA GTA AGT GAT AAT GTG ACG GAT AAG TGG ATA TTG TCG AGT TGT CAA    1824
Glu Val Ser Asp Asn Val Thr Asp Lys Trp Ile Leu Ser Ser Cys Gln
            1180                1185                1190

AGT CTT ATA AGT TTC ATT AAG AAA GAA ATG TCA GAG TAT CGT TTA TAT    1872
Ser Leu Ile Ser Phe Ile Lys Lys Glu Met Ser Glu Tyr Arg Leu Tyr
        1195                1200                1205

ACA GTG TTA CCA ATG CTT CTT AAA CTT ATT GAA GAT ATG ACA AAT TGG    1920
Thr Val Leu Pro Met Leu Leu Lys Leu Ile Glu Asp Met Thr Asn Trp
    1210                1215                1220

TAT ATT AGA TTT AAT AGG CAA AGG TTA AAA GGA ATG TAT GGA AAA GAT    1968
Tyr Ile Arg Phe Asn Arg Gln Arg Leu Lys Gly Met Tyr Gly Lys Asp
1225                1230                1235                1240

GAT ACT TTG ATT GCA TTG AAT GTA CTT TTT GAT GTT TTA TAT ACT TTA    2016
Asp Thr Leu Ile Ala Leu Asn Val Leu Phe Asp Val Leu Tyr Thr Leu
                1245                1250                1255

TGT AGA ACA ATG GCT CCT TTT ACA CCA TTT TTG ACA GAA GCT ATT TAT    2064
Cys Arg Thr Met Ala Pro Phe Thr Pro Phe Leu Thr Glu Ala Ile Tyr
            1260                1265                1270

CAA AAT CTT AAG AAA TAT ATT CCA AAG ACT ACA GAG GAT GAT GTT AGA    2112
Gln Asn Leu Lys Lys Tyr Ile Pro Lys Thr Thr Glu Asp Asp Val Arg
```

```
                1275                1280                1285
TCA ATA CAT TTT GTT AGT TTT CCT GAT GTT ATA GAA GAG CGT TTT CAG     2160
Ser Ile His Phe Val Ser Phe Pro Asp Val Ile Glu Glu Arg Phe Gln
    1290                1295                1300

CTT GAT GTT GAA AGA AAA TTT AAT AGA ATG CAA AAG GTA GTT GAT TTA     2208
Leu Asp Val Glu Arg Lys Phe Asn Arg Met Gln Lys Val Val Asp Leu
1305                1310                1315                1320

GCA CGT AAT CTT AGA GAA AAA GAA TCA GTT AGA TTG AAG GTA CCT TTA     2256
Ala Arg Asn Leu Arg Glu Lys Glu Ser Val Arg Leu Lys Val Pro Leu
            1325                1330                1335

AAA CAG CTT GTT GTA ATA CAT CAT GAT GAA CAA TAT TTG AGT GAT ATT     2304
Lys Gln Leu Val Val Ile His His Asp Glu Gln Tyr Leu Ser Asp Ile
        1340                1345                1350

AAA TCT GTC GAA CAA TAT ATT AAA GAA GAG TTA AAT ATT AGA GAT CTT     2352
Lys Ser Val Glu Gln Tyr Ile Lys Glu Glu Leu Asn Ile Arg Asp Leu
    1355                1360                1365

TTT CTT TCT CCA AAT GAA GAG GAA TAT GGT GTT AGA TAT AGT CTT GTA     2400
Phe Leu Ser Pro Asn Glu Glu Glu Tyr Gly Val Arg Tyr Ser Leu Val
1370                1375                1380

GCA GAT TGG CCT GTT CTT GGT AAA CGA CTT CGA AAA GAT ATT GTT AAA     2448
Ala Asp Trp Pro Val Leu Gly Lys Arg Leu Arg Lys Asp Ile Val Lys
1385                1390                1395                1400

GTT AAG GAC TTT CTA TCA AAT GTA ACT TCT GAA CAA GCC AAA GAA TTT     2496
Val Lys Asp Phe Leu Ser Asn Val Thr Ser Glu Gln Ala Lys Glu Phe
            1405                1410                1415

ATG AAA AAT AAA GAA ATT ATT GTT GAT GAT ATT AAA TTA GTT GAA GGA     2544
Met Lys Asn Lys Glu Ile Ile Val Asp Asp Ile Lys Leu Val Glu Gly
        1420                1425                1430

GAT CTT CAG GTT ATA CGG ACT CTT GAT TTT AAA GAT ACA ATG TAT TAT     2592
Asp Leu Gln Val Ile Arg Thr Leu Asp Phe Lys Asp Thr Met Tyr Tyr
    1435                1440                1445

CAA ACC AAT ACT GAT CAA GAT GTT TTT ATC ATT TTA GAT ACT AAA ATT     2640
Gln Thr Asn Thr Asp Gln Asp Val Phe Ile Ile Leu Asp Thr Lys Ile
1450                1455                1460

TAT CCT GAA TTA AAA ACT GAA TAT CTT GTA AGA GAG GTA ATT AAT CGT     2688
Tyr Pro Glu Leu Lys Thr Glu Tyr Leu Val Arg Glu Val Ile Asn Arg
1465                1470                1475                1480

GTT CAA CGT CTT CGT AAG AAA GTT GGT TTA CAA GTT ATT GAT GAT ATT     2736
Val Gln Arg Leu Arg Lys Lys Val Gly Leu Gln Val Ile Asp Asp Ile
            1485                1490                1495

CGA ATG GAA TAT GTT ATA ATT GAT GAT TCT ATA GGT TTG GAA GAT GCT     2784
Arg Met Glu Tyr Val Ile Ile Asp Asp Ser Ile Gly Leu Glu Asp Ala
        1500                1505                1510

ATT TCT CAG CAT CAG ATA CTT TTA ACC AAA ATC CTT CGT AGG CCT TTA     2832
Ile Ser Gln His Gln Ile Leu Leu Thr Lys Ile Leu Arg Arg Pro Leu
    1515                1520                1525

GAA AAA AAT CAA TCA ATA TTA GAT GAA ACA GAT CCT AAA CAG ATT GTA     2880
Glu Lys Asn Gln Ser Ile Leu Asp Glu Thr Asp Pro Lys Gln Ile Val
1530                1535                1540

AAA GAA AAA CAG GAT GTT CAA GGC GCA ACA TTT ATG TTA TCT TTA TTA     2928
Lys Glu Lys Gln Asp Val Gln Gly Ala Thr Phe Met Leu Ser Leu Leu
1545                1550                1555                1560

CGA TTA TAAAATATTT ATTAATAAAA ATCATTAATA TTTCAAAAAA AAAAAAAAA       2984
Arg Leu
AAAAAAAAA                                                            2993

(2) INFORMATION FOR SEQ ID NO:43:

(i) SEQUENCE CHARACTERISTICS:
        (A) LENGTH: 978 amino acids
        (B) TYPE: amino acid
```

(D) TOPOLOGY: linear (ii) MOLECULE TYPE: peptide (xi) SEQUENCE DESCRIPTION: SEQ ID NO:43:

```
Ile Asp Lys Lys Leu Gly Ile Asn Gly Lys Glu Asp Ile Met Ala Ile
  1               5                  10                  15
Gly Ile Glu Lys Tyr Asn Ser Glu Cys Arg Ala Ile Val Met Arg Tyr
                 20                  25                  30
Ser Glu Gln Trp Arg Glu Lys Ile Glu Arg Leu Gly Arg Trp Ile Glu
             35                  40                  45
Phe Asp Asn Asp Tyr Lys Thr Leu Asp Thr Leu Phe Met Gln Ser Val
         50                  55                  60
Trp Tyr Ile Phe Lys Lys Leu Tyr Glu Lys Gly Lys Val Tyr Arg Gly
 65                  70                  75                  80
Phe Lys Val Met Pro Tyr Ser Thr Ala Cys Met Thr Pro Leu Ser Asn
                 85                  90                  95
Phe Glu Ala Gln Gln Asn Tyr Lys Lys Val Ser Asp Pro Ser Val Val
                100                 105                 110
Ile Ser Phe Pro Leu Leu Glu Asp Pro Ser Thr Ser Leu Leu Ala Trp
            115                 120                 125
Thr Thr Thr Pro Trp Thr Leu Pro Ser His Leu Asn Leu Cys Val Asn
        130                 135                 140
Pro Asp Phe Glu Tyr Ile Lys Ile Tyr Asp Glu Ala Ser Gly Glu Asn
145                 150                 155                 160
Tyr Ile Leu Leu Glu Lys Cys Leu Ser Ile Leu Tyr Lys Asp Pro Lys
                165                 170                 175
Asn Ala Lys Phe Thr Lys Leu Gln Thr Ile Lys Gly Ala Asp Met Lys
            180                 185                 190
Gly Trp Lys Tyr Asp Pro Pro Phe Tyr Phe Tyr Glu Arg Phe Lys
        195                 200                 205
Glu Arg Ala Phe Asn Val Leu Leu Ala Gln Tyr Val Thr Ser Asp Asn
    210                 215                 220
Gly Thr Gly Ile Val His Gln Ala Pro Ala Phe Gly Glu Asp Asp Tyr
225                 230                 235                 240
Asn Val Ala Phe Glu Asn Gly Ile Ile Asp Glu Asn Phe Tyr Pro Pro
                245                 250                 255
Cys Pro Leu Asp Glu Lys Gly Asn Phe Thr Ala Glu Val Ser Asp Phe
            260                 265                 270
Ala Gly Met Tyr Val Lys Asp Ala Asp Lys Ala Ile Gln Lys Val Leu
        275                 280                 285
Lys Gln Lys Lys Arg Leu Val Ile Gln Ser Gln Ile Ile His Ser Tyr
    290                 295                 300
Pro Phe Cys Trp Arg Ser Asp Thr Pro Leu Leu Tyr Arg Val Val Pro
305                 310                 315                 320
Ser Trp Phe Val Lys Val Lys Glu Ser Thr Lys Glu Met Leu Glu Ala
                325                 330                 335
Leu Glu Ser Thr Arg Trp Val Pro Ser Phe Val Lys Asp Lys Arg Phe
            340                 345                 350
Ala Asn Trp Ile Thr Gly Cys Arg Asp Trp Asn Ile Ser Arg Asn Arg
        355                 360                 365
Tyr Trp Gly Thr Pro Ile Pro Leu Trp Val Ser Asp Phe Glu Glu
    370                 375                 380
Ile Val Cys Ile Gly Ser Val Ser Glu Leu Glu Leu Ser Gly Val
385                 390                 395                 400
```

```
Arg Asn Leu Thr Asp Ile His Arg Asp Lys Ile Asp His Ile Thr Ile
                405                 410                 415
Pro Ser Lys Lys Gly Lys Asn Ala Leu Lys Arg Ile Glu Asp Val Phe
                420                 425                 430
Asp Cys Trp Phe Glu Ser Gly Ser Met Pro Tyr Ala Ser Val Tyr Tyr
                435                 440                 445
Pro Phe Gln Asn Ser Glu Asn Phe Met Glu Lys Phe Pro Ala Asp Phe
450                 455                 460
Ile Ala Glu Gly Leu Val Gln Thr Arg Gly Trp Phe Tyr Thr Leu Leu
465                 470                 475                 480
Val Leu Gly Val Gln Leu Phe Gly Ile Ala Pro Phe Lys Asn Val Ile
                485                 490                 495
Val Asn Gly Leu Val Leu Ala Ser Asp Gly Lys Lys Met Ser Lys Arg
                500                 505                 510
Leu Lys Asn Tyr Pro Glu Leu Ser Ile Val Leu Asp Lys Tyr Gly Ala
                515                 520                 525
Asp Ala Leu Arg Leu Tyr Leu Ile Asn Ser Pro Val Val Arg Ala Glu
                530                 535                 540
Pro Leu Lys Phe Lys Glu Asp Gly Val Lys Asp Val Val Ala Lys Val
545                 550                 555                 560
Ile Ile Pro Trp Trp Asn Ser Tyr Asn Phe Phe Glu Met Gln Val Lys
                565                 570                 575
Leu Leu Lys Lys Thr His Asn Ile Asp Phe Met Tyr Asn Leu Ser Asn
                580                 585                 590
Glu Val Ser Asp Asn Val Thr Asp Lys Trp Ile Leu Ser Ser Cys Gln
                595                 600                 605
Ser Leu Ile Ser Phe Ile Lys Lys Glu Met Ser Glu Tyr Arg Leu Tyr
                610                 615                 620
Thr Val Leu Pro Met Leu Leu Lys Leu Ile Glu Asp Met Thr Asn Trp
625                 630                 635                 640
Tyr Ile Arg Phe Asn Arg Gln Arg Leu Lys Gly Met Tyr Gly Lys Asp
                645                 650                 655
Asp Thr Leu Ile Ala Leu Asn Val Leu Phe Asp Val Leu Tyr Thr Leu
                660                 665                 670
Cys Arg Thr Met Ala Pro Phe Thr Pro Phe Leu Thr Glu Ala Ile Tyr
                675                 680                 685
Gln Asn Leu Lys Lys Tyr Ile Pro Lys Thr Thr Glu Asp Asp Val Arg
                690                 695                 700
Ser Ile His Phe Val Ser Phe Pro Asp Val Ile Glu Glu Arg Phe Gln
705                 710                 715                 720
Leu Asp Val Glu Arg Lys Phe Asn Arg Met Gln Lys Val Val Asp Leu
                725                 730                 735
Ala Arg Asn Leu Arg Glu Lys Ser Val Arg Leu Lys Val Pro Leu
                740                 745                 750
Lys Gln Leu Val Val Ile His His Asp Glu Gln Tyr Leu Ser Asp Ile
                755                 760                 765
Lys Ser Val Glu Gln Tyr Ile Lys Glu Leu Asn Ile Arg Asp Leu
                770                 775                 780
Phe Leu Ser Pro Asn Glu Glu Tyr Gly Val Arg Tyr Ser Leu Val
785                 790                 795                 800
Ala Asp Trp Pro Val Leu Gly Arg Leu Arg Lys Asp Ile Val Lys
                805                 810                 815
Val Lys Asp Phe Leu Ser Asn Val Thr Ser Glu Gln Ala Lys Glu Phe
```

-continued

```
                      820                 825                 830
Met Lys Asn Lys Glu Ile Ile Val Asp Asp Ile Lys Leu Val Glu Gly
                835                 840                 845

Asp Leu Gln Val Ile Arg Thr Leu Asp Phe Lys Asp Thr Met Tyr Tyr
    850                 855                 860

Gln Thr Asn Thr Asp Gln Asp Val Phe Ile Ile Leu Asp Thr Lys Ile
865                 870                 875                 880

Tyr Pro Glu Leu Lys Thr Glu Tyr Leu Val Arg Glu Val Ile Asn Arg
                885                 890                 895

Val Gln Arg Leu Arg Lys Lys Val Gly Leu Gln Val Ile Asp Asp Ile
                900                 905                 910

Arg Met Glu Tyr Val Ile Ile Asp Asp Ser Ile Gly Leu Glu Asp Ala
                915                 920                 925

Ile Ser Gln His Gln Ile Leu Leu Thr Lys Ile Leu Arg Arg Pro Leu
    930                 935                 940

Glu Lys Asn Gln Ser Ile Leu Asp Glu Thr Asp Pro Lys Gln Ile Val
945                 950                 955                 960

Lys Glu Lys Gln Asp Val Gln Gly Ala Thr Phe Met Leu Ser Leu Leu
                965                 970                 975

Arg Leu
```

(2) INFORMATION FOR SEQ ID NO:44:

(i) SEQUENCE CHARACTERISTICS:
        (A) LENGTH: 1352 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 101..1210

(xi) SEQUENCE DESCRIPTION: SEQ ID NO:44:

```
GAATTCAGCT CGTGCCGCTC GTGCCGGTTA ATATTTAGAG AAGTTGTACT GTAAAAACAA         60

CGTTTTATAA TATACATTTT TAAAAGAACT TTTAAGCATT ATG GGA TTT ACA AGT        115
                                             Met Gly Phe Thr Ser
                                                             980

GAA ATA GTT AAT AAA AAA TAT GAA CTT ATT ACA CGT GGA CTT CAA GAA        163
Glu Ile Val Asn Lys Lys Tyr Glu Leu Ile Thr Arg Gly Leu Gln Glu
    985                 990                 995

GTT CTT GGT GCA GAA AGA CTT AGA AAG ATT TTA GAG GAG AGG GAT TTA        211
Val Leu Gly Ala Glu Arg Leu Arg Lys Ile Leu Glu Glu Arg Asp Leu
1000                1005                1010                1015

AAA CTT TAT TGG GGC ACT TCA CCT ACA GGA AAA CCT CAT TGT GGA TAC        259
Lys Leu Tyr Trp Gly Thr Ser Pro Thr Gly Lys Pro His Cys Gly Tyr
                1020                1025                1030

TTT GTT CCT ATG ATC AAA ATT GCA GAC TTT TTA AAA GCA GAA GTT GAA        307
Phe Val Pro Met Ile Lys Ile Ala Asp Phe Leu Lys Ala Glu Val Glu
                1035                1040                1045

GTT ACT ATT CTT TTT GCA GAT ATT CAT GCA TTT TTA GAT AAT CTT AAA        355
Val Thr Ile Leu Phe Ala Asp Ile His Ala Phe Leu Asp Asn Leu Lys
                1050                1055                1060

GCA CCT ATT GAT ATT GTA AAA TAT AGG GCC AAA TAT TAT GAA TTT ATT        403
Ala Pro Ile Asp Ile Val Lys Tyr Arg Ala Lys Tyr Tyr Glu Phe Ile
                1065                1070                1075

ATT AAA GCT ATT CTT AAA TCA ATT GGC GTT TCA ACT GAA AAG CTC AGA        451
Ile Lys Ala Ile Leu Lys Ser Ile Gly Val Ser Thr Glu Lys Leu Arg
```

-continued

```
        1080            1085            1090            1095
TTT GTT CTT GGA TCG TCT TAT CAA CTA AGT TCT AAG TAT TGT ATG GAC      499
Phe Val Leu Gly Ser Ser Tyr Gln Leu Ser Ser Lys Tyr Cys Met Asp
                1100            1105            1110

AAT TTT CGT CTT TGT ACT ATT GTT ACA GAA CAT GAT GCA AAA AAA GCA      547
Asn Phe Arg Leu Cys Thr Ile Val Thr Glu His Asp Ala Lys Lys Ala
                    1115            1120            1125

GGA GCA GAA GTT GTA AAA CAA GTA GAA AAC AGT CTA CTT TCA GGA CTT      595
Gly Ala Glu Val Val Lys Gln Val Glu Asn Ser Leu Leu Ser Gly Leu
            1130            1135            1140

CTA TAT CCA GGA ATG CAA GCT TTA GAT GAA GAA TAT TTA GAT AGT GAT      643
Leu Tyr Pro Gly Met Gln Ala Leu Asp Glu Glu Tyr Leu Asp Ser Asp
        1145            1150            1155

GCT CAA TTT GGG GGA GTT GAT CAA AGG AAA ATT TTT ACA TTT GCT GAA      691
Ala Gln Phe Gly Gly Val Asp Gln Arg Lys Ile Phe Thr Phe Ala Glu
1160            1165            1170            1175

AAA TAT CTT CCA ATG CTT GGA TTA AAA AAA AGA ATA CAT CTT ATG AGT      739
Lys Tyr Leu Pro Met Leu Gly Leu Lys Lys Arg Ile His Leu Met Ser
                    1180            1185            1190

CCA ATG ATA CCC GGT CTT GCA GGA GGA AAA ATG TCT GCT TCA GGA AAC      787
Pro Met Ile Pro Gly Leu Ala Gly Gly Lys Met Ser Ala Ser Gly Asn
                1195            1200            1205

GAA AAT AAC AAA ATT GAT ATT TTG GAT GAT GCA GAA ACT GTT AAA AAA      835
Glu Asn Asn Lys Ile Asp Ile Leu Asp Asp Ala Glu Thr Val Lys Lys
            1210            1215            1220

AAA ATA AAT AAA GCA TTA TGC GTA GAA GCA GCT GTA GAA AAT AAT GGT      883
Lys Ile Asn Lys Ala Leu Cys Val Glu Ala Ala Val Glu Asn Asn Gly
        1225            1230            1235

CTT TTA GAA TTA GCA AAA CAT GTA ATT TTT CCT GTT CTG GCA CTT AAA      931
Leu Leu Glu Leu Ala Lys His Val Ile Phe Pro Val Leu Ala Leu Lys
1240            1245            1250            1255

GGA ATT CCA GCA CTA ACA ATC AAT CGA GAA GAA AAA TGG GGA GGC CCA      979
Gly Ile Pro Ala Leu Thr Ile Asn Arg Glu Glu Lys Trp Gly Gly Pro
                    1260            1265            1270

GTT TCA TAC AAT TCT TAT GAG CTT TTA GAA TTG GAA TAT GTA AAC AGA     1027
Val Ser Tyr Asn Ser Tyr Glu Leu Leu Glu Leu Glu Tyr Val Asn Arg
                1275            1280            1285

AAG TTA TCT CCT CAA GAT CTC AAA ATT GGA ATT AGC GAT TCA CTT AAT     1075
Lys Leu Ser Pro Gln Asp Leu Lys Ile Gly Ile Ser Asp Ser Leu Asn
            1290            1295            1300

TTT CTT TTA GAG TCT ATT CGA TTA GAA TTT GCA GAA AAT AAA GAA TTT     1123
Phe Leu Leu Glu Ser Ile Arg Leu Glu Phe Ala Glu Asn Lys Glu Phe
        1305            1310            1315

CAA GAA ATA CTT CAT CTT GCT TAT CCA AAT GAA GGA AAA CAA GAA TCC     1171
Gln Glu Ile Leu His Leu Ala Tyr Pro Asn Glu Gly Lys Gln Glu Ser
1320            1325            1330            1335

CAA AAA AAA TCC AAC AAA AAT ATT AAA GTT AAT TCA AAC TAAAAATCTG      1220
Gln Lys Lys Ser Asn Lys Asn Ile Lys Val Asn Ser Asn
                    1340            1345

GACATCCAAA ACTTTCATCT TCACTAAACT CATGATTTTC CTATCTAAAA ATATATTTTT    1280

ATAATGTATA TAATTTTAAA ATTGTTTATT CTTATAATTA CAATTATAAA AAAAAAAAA     1340

AAAAAACTCG AG                                                      1352
```

(2) INFORMATION FOR SEQ ID NO:45:

(i) SEQUENCE CHARACTERISTICS:
        (A) LENGTH: 370 amino acids
        (B) TYPE: amino acid
        (D) TOPOLOGY: linear (ii) MOLECULE TYPE: protein (xi) SEQUENCE DESCRIPTION: SEQ ID NO:45:

```
Met Gly Phe Thr Ser Glu Ile Val Asn Lys Lys Tyr Glu Leu Ile Thr
 1               5                  10                  15

Arg Gly Leu Gln Glu Val Leu Gly Ala Glu Arg Leu Arg Lys Ile Leu
                20                  25                  30

Glu Glu Arg Asp Leu Lys Leu Tyr Trp Gly Thr Ser Pro Thr Gly Lys
            35                  40                  45

Pro His Cys Gly Tyr Phe Val Pro Met Ile Lys Ile Ala Asp Phe Leu
        50                  55                  60

Lys Ala Glu Val Glu Val Thr Ile Leu Phe Ala Asp Ile His Ala Phe
 65                  70                  75                  80

Leu Asp Asn Leu Lys Ala Pro Ile Asp Ile Val Lys Tyr Arg Ala Lys
                85                  90                  95

Tyr Tyr Glu Phe Ile Ile Lys Ala Ile Leu Lys Ser Ile Gly Val Ser
            100                 105                 110

Thr Glu Lys Leu Arg Phe Val Leu Gly Ser Ser Tyr Gln Leu Ser Ser
        115                 120                 125

Lys Tyr Cys Met Asp Asn Phe Arg Leu Cys Thr Ile Val Thr Glu His
130                 135                 140

Asp Ala Lys Lys Ala Gly Ala Glu Val Val Lys Gln Val Glu Asn Ser
145                 150                 155                 160

Leu Leu Ser Gly Leu Leu Tyr Pro Gly Met Gln Ala Leu Asp Glu Glu
                165                 170                 175

Tyr Leu Asp Ser Asp Ala Gln Phe Gly Gly Val Asp Gln Arg Lys Ile
            180                 185                 190

Phe Thr Phe Ala Glu Lys Tyr Leu Pro Met Leu Gly Leu Lys Lys Arg
        195                 200                 205

Ile His Leu Met Ser Pro Met Ile Pro Gly Leu Ala Gly Gly Lys Met
    210                 215                 220

Ser Ala Ser Gly Asn Glu Asn Asn Lys Ile Asp Ile Leu Asp Asp Ala
225                 230                 235                 240

Glu Thr Val Lys Lys Lys Ile Asn Lys Ala Leu Cys Val Glu Ala Ala
                245                 250                 255

Val Glu Asn Asn Gly Leu Leu Glu Leu Ala Lys His Val Ile Phe Pro
            260                 265                 270

Val Leu Ala Leu Lys Gly Ile Pro Ala Leu Thr Ile Asn Arg Glu Glu
        275                 280                 285

Lys Trp Gly Gly Pro Val Ser Tyr Asn Ser Tyr Glu Leu Leu Glu Leu
    290                 295                 300

Glu Tyr Val Asn Arg Lys Leu Ser Pro Gln Asp Leu Lys Ile Gly Ile
305                 310                 315                 320

Ser Asp Ser Leu Asn Phe Leu Leu Glu Ser Ile Arg Leu Glu Phe Ala
                325                 330                 335

Glu Asn Lys Glu Phe Gln Glu Ile Leu His Leu Ala Tyr Pro Asn Glu
            340                 345                 350

Gly Lys Gln Glu Ser Gln Lys Lys Ser Asn Lys Asn Ile Lys Val Asn
        355                 360                 365

Ser Asn
    370
```

(2) INFORMATION FOR SEQ ID NO:46:

(i) SEQUENCE CHARACTERISTICS:

(A) LENGTH: 40 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:46:

GGTACCGGTA CCTTTTTTTT TTTTTTTTTT AAATACATAC                40